US011040990B2

(12) United States Patent
Dobelmann-Mara et al.

(10) Patent No.: US 11,040,990 B2
(45) Date of Patent: Jun. 22, 2021

(54) COMPOUNDS CONTAINING SI ATOMS FOR OPTICALLY ACTIVE DEVICES

(71) Applicant: Merck Patent GmbH, Darmstadt (DE)

(72) Inventors: Lars Dobelmann-Mara, Darmstadt (DE); Stefan Riedmueller, Frankfurt am Main (DE); Martin Schraub, Alsbach-Haehnlein (DE)

(73) Assignee: Merck Patent GmbH, Darmstadt (DE)

( * ) Notice: Subject to any disclaimer, the term of this patent is extended or adjusted under 35 U.S.C. 154(b) by 42 days.

(21) Appl. No.: 16/485,886

(22) PCT Filed: Feb. 14, 2018

(86) PCT No.: PCT/EP2018/053632
§ 371 (c)(1),
(2) Date: Aug. 14, 2019

(87) PCT Pub. No.: WO2018/149857
PCT Pub. Date: Aug. 23, 2018

(65) Prior Publication Data

US 2020/0002363 A1 Jan. 2, 2020

(30) Foreign Application Priority Data

Feb. 15, 2017 (EP) .................................... 17156331

(51) Int. Cl.

| | |
|---|---|
| ***C07D 311/12*** | (2006.01) |
| ***C07D 405/04*** | (2006.01) |
| ***C07D 407/04*** | (2006.01) |
| ***C07D 409/04*** | (2006.01) |
| ***C07F 7/18*** | (2006.01) |
| ***C08G 77/24*** | (2006.01) |
| ***C08G 77/00*** | (2006.01) |
| ***G02B 1/04*** | (2006.01) |

(52) U.S. Cl.
CPC .......... *C07F 7/1804* (2013.01); *C07D 311/12* (2013.01); *C07D 405/04* (2013.01); *C07D 407/04* (2013.01); *C07D 409/04* (2013.01); *C08G 77/24* (2013.01); *C08G 77/80* (2013.01); *G02B 1/043* (2013.01)

(58) Field of Classification Search
CPC .. C07D 311/12; C07D 405/04; C07D 407/04; C07D 409/04; C08G 77/24
See application file for complete search history.

(56) References Cited

U.S. PATENT DOCUMENTS

| | | | |
|---|---|---|---|
| 5,290,892 A | 3/1994 | Namdaran et al. | |
| 5,331,073 A | 7/1994 | Weinschenk et al. | |
| 5,693,095 A | 12/1997 | Freeman et al. | |
| 7,399,767 B2 | 7/2008 | Zhang et al. | |
| 8,109,999 B2 | 2/2012 | Hampp | |
| 2010/0324165 A1 | 12/2010 | Ritter et al. | |
| 2019/0389829 A1* | 12/2019 | Dobelmann-Mara | A61L 27/50 |
| 2020/0002304 A1* | 1/2020 | Dobelmann-Mara | A61L 27/16 |
| 2020/0262805 A1* | 8/2020 | Dobelmann-Mara | C07D 215/227 |
| 2020/0332041 A1* | 10/2020 | Dobelmann-Mara | C08F 2/02 |

FOREIGN PATENT DOCUMENTS

| | | |
|---|---|---|
| WO | 06078834 A1 | 7/2006 |
| WO | 07033831 A1 | 3/2007 |
| WO | 09074520 A2 | 6/2009 |
| WO | 09074521 A1 | 6/2009 |

OTHER PUBLICATIONS

M. Schraub et al.: "Photoinduced refractive index changes of 3-phenyl-coumarin containing polymers for ophthalmic applications", European Polymer Journal, vol. 51, Dec. 1, 2013 (Dec. 1, 2013), pp. 21-27.
M Schraub et al., European Polymer Journal, vol. 49, 2013, pp. 1714-1721.
Siegel et al., J. Am. Chem. Soc., vol. 120, 1998, pp. 9680-9681.
Qin et al., Polymer International, vol. 48, 1999, pp. 491-494.
Shashidhar et al., J. Mater. Chem., vol. 11, 2001, pp. 2992-2995.
Jean-Marc Legeais, J Cataract Refract Surg, vol. 24, 1998, pp. 371-379.
Suratwala et al., Journal of Sol-Gel Science and Technology, vol. 8, 1997, pp. 973-978.

* cited by examiner

*Primary Examiner* — D Margaret M Seaman
(74) *Attorney, Agent, or Firm* — Millen White Zelano & Branigan, PC; Brion P. Heaney

(57) ABSTRACT

The present invention relates to novel compounds, particularly to compounds comprising a photoactive unit, said novel compounds being particularly suitable for compositions and ophthalmic devices as well as to compositions and ophthalmic devices comprising such compounds.

38 Claims, No Drawings

COMPOUNDS CONTAINING SI ATOMS FOR OPTICALLY ACTIVE DEVICES

FIELD OF THE INVENTION

The present invention relates to novel compounds, particularly to compounds comprising a photoactive unit, said novel compounds being particularly suitable for compositions and ophthalmic devices as well as to compositions and ophthalmic devices comprising such compounds.

BACKGROUND OF THE INVENTION

Cataract is a general term for an affection of the eye that leads to a loss of vision and in the extreme to blindness by clouding of the normally clear lens of the eye. It is the major cause of blindness in the world, affecting more than 100 million people. Due to the fact that its major cause is age and the population's average age is increasing, it is expected that the number of cataracts will continue to increase substantially in the future.

Effective treatment of cataract is only possible by surgical intervention, whereby the natural lens of the eye is removed through an incision in the cornea and replaced with an artificial lens, often also referred to as "intraocular lens". In preparation of surgery current state-of-the-art surgical methods employ eye mapping so as to approximate the refractive power best suited to the respective patient.

Even though cataract surgery is one of the most widely used and safest surgical procedures it is not without specific post-surgery problems. It frequently happens that the refractive power of the implanted intraocular lens (IOL) is insufficient for restoring good vision. Such problems may, for example, be caused by changes in eye geometry as consequence of the surgery as well as irregular wound healing and positioning errors that result in the artificial lens not having the optimal optical properties. As a result the patient will still require corrective vision aids, e.g. glasses, to be able to see correctly. In some cases the resulting refractive power of the implanted artificial lens is so far removed from the required refractive power that further surgery will be required. Particularly for aged persons this is not desirable because the body's capability for healing is reduced with increasing age. Furthermore, there is the risk of attracting endophthalmitis, an inflammation of the eye, which can even lead to a complete loss of vision or worse, loss of the eye.

There is therefore a need in the health sector for optically active devices, and particularly artificial intraocular lenses, that would allow for non-invasive adjustment of refractive power after implantation of the lens, thereby preferably further reducing the need for post-surgery vision aids.

Some developments in this sense have already been made, as for example evidenced by WO 2007/033831 A1, WO 2009/074520 A2 or US 20100324165 A1 corresponding to WO 2009/074521 A1.

WO 2009/074521 A1 describes ophthalmological compositions comprising coumarin acrylates or methacrylates.

Suratwala et al, Journal of Sol-Gel Science and Technology 1997, 8, 973-978 describe silylated coumarin dyes in polyceram hosts forming crack free, polishable monoliths.

WO 2006/078834 A1 describes heterocyclic benzo[c] chromene derivatives useful as modulators of the estrogen receptors.

J. Träger et al, describes polymers for in vivo tuning of refractive properties in intraocular lenses such as homopolymers comprising polymerized 7-(3-methacryloyloxypropoxy)coumarin (MAOC-$C_3$) being slightly opaque and having a $T_g$ of 76° C., homopolymers comprising polymerized 7-(5-methacryloyloxypentoxy)coumarin (MAOC-$C_5$) being transparent and having a $T_g$ of 52° C. and homopolymers comprising polymerized 7-(7-methacryloyloxyheptoxy)coumarin (MAOC-$C_7$) being transparent and having a $T_g$ of 45° C.

M. Schraub et al, European Polymer Journal 49 (2013), 1714-1721 describes high refractive index coumarin-based photorefractive polysiloxanes.

M. Schraub et al, European Polymer Journal 51 (2014) 21-27 describes the photochemistry of 3-phenyl-coumarin containing polymethacrylates.

Siegel et al., J. Am. Chem. Soc., (1998), 120, 9680-9681 describes the synthesis of bifunctional photorefractive polymers with net gain.

Qin et al., Polymer International 48, (1999), 491-494 describes the synthesis and structural characterization of novel multifunctional polysiloxanes having photo-refractive properties.

Shashidhar et al, J. Mater. Chem. (2001), 11, 2992-2995 describes the synthesis and photodimerization in self-assembled monolayers of 7-(8-trimethoxysilyloctyloxy)coumarin.

Poly(methyl methacrylate) (PMMA) intraocular lenses (IOLs) that were coated with Teflon AF®, an amorphous, transparent, and highly hydrophobic fluorocarbon polymer is known from Jean-Marc Legeais, J Cataract Refract Surg. 1998, 24, 371-379. Teflon AF® (Dupont de Nemours) is a poly(tetra-fluoroethylene co-hexafluoro-propyl-2 cyclodethoxydifluoroethylene). Constituted entirely of high-energy bonds, it is stable at temperatures up to 260° C. and chemically very resistant. The refractive index is 1.32. It transmits light from 200 to 2000 nm with a constant light absorption below 5%. The contact angle with water is 129 degrees. The surface modification is described using a PMMA IOL (model 808A, Kabi Pharmacia Production B.V.) having an overall diameter of 12.0 mm and optic diameter of 6.5 mm which is coated by immersing the lense in a 5% solution of Teflon AF in a fluorocarbon solvent ($C_8F_{18}$) for 3 seconds and then placing it at a temperature of 37° C. to evaporate the solvent. As a result, the surface of the PMMA IOL was completely coated with Teflon AF.

Eun-Ho Sohn et al describe surface properties of poly (methyl methacrylate) (PMMA) films using poly(perfluoromethyl methacrylate)s (PFMMAs) with short perfluorinated side chains. 2,2,2-Trifluoroethyl methacrylate, 1,1,1,3,3,3-hexafluoroisopropyl methacrylate, 2,2,3,3,3-pentafluoropropyl methacrylate, 2,2,3,3,4,4,4-heptafluorobutyl methacrylate were prepared by radical polymerization of the corresponding monomers. Film preparation is reported with PMMA, PFMMA and their blends.

However, the compounds disclosed therein suffer from being too stiff and too brittle so that they can't be rolled or folded and are thus not fit to be implanted by state of the art cataract surgical methods, particularly by state of the art micro-incision cataract surgical methods.

Consequently, it is an objective of the present application to provide for novel compounds suitable for ophthalmic devices.

It is also an objective of the present application to provide for compounds, the optical properties of which may be changed, preferably by non-invasive techniques.

It is a further objective of the present application to provide for novel compounds having advantages over currently known compounds, preferably in combination with being suitable for ophthalmic devices.

Advantages such as better flexibility and objectives of the compounds of the present application will be evident to the skilled person from the following detailed description as well as from the examples.

SUMMARY OF THE INVENTION

The present inventors have found that the above objects may be attained either individually or in any combination by the compounds and ophthalmic devices of the present application.

The invention relates to compounds of formula (I)

(I)

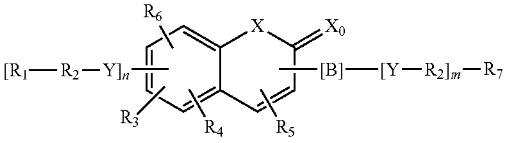

wherein

X is O, S or $NR_0$, $X_0$ is O or S,

Y is O, S or a bond, n is 0 or 1, m is 0 or 1, n+m is 1 or 2,

—[B]— is selected from the group consisting of formula (1) to formula (4), (1)

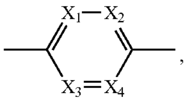

(2)

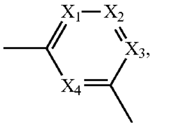

(3)

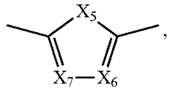

(4)

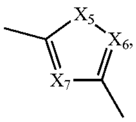

$X_1$, $X_2$, $X_3$, $X_4$ are each independently of each other CR' or N, $X_5$ is each independently O, S, C═O or $NR_0$, $X_6$, $X_7$ are each independently CR' or N, R is at each occurrence independently selected from the group consisting of H, F, a linear or branched alkyl group having 1 to 4 C atoms or a linear or branched partially or fully fluorinated alkyl group having 1 to 4 C atoms, R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms, $R_0$ is at each occurrence independently selected from the group consisting of a linear or branched alkyl group having 1 to 10 C atoms or a cycloalkyl group having 3 to 6 C atoms, $R_1$ is a polymerizable group containing at least one Si atom, $—R_2—$ is $—(C(R)_2)_o—$, $—(C(R)_2)_p—X_8—(C(R)_2)_q—(X_9)_s—(C(R)_2)_r—(X_{10})_t—(C(R)_2)_u—$ or a cycloalkylene group having 5 or 6 C atoms which can be substituted with at least one R which is different from H, o is selected from the group consisting of 1 to 20, $X_8$, $X_9$, $X_{10}$ are at each occurrence independently O, S or $NR_0$, s, t is 0 or 1, p, q are at each occurrence independently selected from the group consisting of 1 to 10, r, u are at each occurrence independently selected from the group consisting of 0 to 10, wherein the overall number of atoms for $—(C(R)_2)_p—X_8—(C(R)_2)_q—(X_9)_s—(C(R)_2)_r—(X_{10})_t—(C(R)_2)_u—$ is up to 20 atoms, $R_3$, $R_4$, $R_5$, $R_6$ are at each occurrence independently R', $R_7$ is R' in case m is 0 and $R_7$ is $R_1$ in case m is 1.

Preferably, the substituent $[R_1—R_2—Y]_n$ is bonded in position 7 or 6 of the heterocyclus. Particularly preferably, the substituent $[R_1—R_2—Y]_n$ is bonded in position 7 of the heterocyclus. Such compounds are represented by formula (I-1) and (I-2)

(I-1)

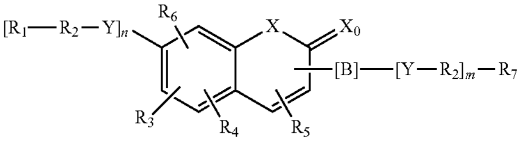

(I-2)

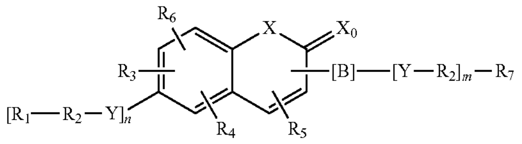

wherein $R_1$, $—R_2—$, Y, n, $R_3$, $R_4$, $R_5$, $R_6$, $R_7$, X, $X_0$, m and [B] have a meaning as described before.

The invention relates further to compositions comprising at least one of said compounds of formula (I) and/or their polymerized forms as well as to articles comprising at least one polymerized compound of formula (I).

In addition, the invention relates to a process for forming such article, said process comprising the steps of providing a composition comprising at least one compound of formula (I) and/or an oligomer or polymer as described before;

subsequently forming the article of said composition.

Furthermore, the invention relates to a process for changing the optical properties of an article according to the invention, said process comprising the steps of providing an article comprising at least one polymerized compound of formula (I), and subsequently exposing said article to irradiation having a wavelength of at least 200 nm and at most 1500 nm.

DETAILED DESCRIPTION OF THE INVENTION

The compounds of formula (I) and all preferred embodiments of compounds of formula (I) according to the present invention include all stereoisomers or racemic mixtures.

The compounds of formula I provide several advantages over prior art materials

- by choosing a Si containing polymer backbone they show comparably lower glass transition points than polymers based on acrylate or methacrylate thus becoming better foldable or bendable;
- by adding a linker —[B]— to the 1-benzopyran-2-one, 1-benzopyran-2-thione, thiochromene-2-one, thiochromene-2-thione, quinolin-2-one or quinolin-2-thione ring system their refrective index will increase and UV stability is further enhanced;
- by incorporating at least one F atom or at least one partially or fully fluorinated alkyl group they develop a non-sticky behavior with characteristic surfactant properties; through their non-stickiness the compounds also show a smoother behavior in a physiological environment.

Homopolymers comprising polymerized 7-(3-methacryloyloxypropoxy)coumarin are slightly opaque and have a $T_g$ of 76° C.; homopolymers comprising polymerized 7-(5-methacryloyloxypentoxy)coumarin are transparent and have a $T_g$ of 52° C. and homopolymers comprising polymerized 7-(7-methacryloyloxyheptoxy)coumarin are transparent and have a $T_g$ of 45° C.

In comparison to known acrylate and methacrylate polymer backbones, compounds according to the invention are more stable toward UV-irradiation due to higher stability of the Si—O or Si—N bond.

Polymers that are foldable at room temperature generally exhibit glass transition temperatures ($T_g$) lower than room temperature (ca. 21° C.). They are easily deformable at this temperature without causing physical damage to the polymer, for example by inducing creep, stress or fissures. For polymers in intraocular lenses, $T_g$s of less than or equal to 15° C. are preferred.

Polymers used in intraocular lens manufacturing have preferably relative high refractive indices, which enable the fabrication of thinner intraocular lenses. Preferably, the polymer used in an intraocular lens will have a refractive index greater than about 1.5 and presently most preferably greater than about 1.55.

In case an asterisk ("*") is used within the description of the present invention, it denotes a linkage to an adjacent unit or group or, in case of a polymer, to an adjacent repeating unit or any other group.

A linear or branched alkyl group having 1 to 10 C atoms denotes an alkyl group having 1, 2, 3, 4, 5, 6, 7, 8, 9 or 10 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl or n-decyl. A linear or branched alkyl group having 1 to 20 C atoms include all examples for a linear or branched alkyl group having 1 to 10 C atoms including any alkyl group having 11, 12, 13, 14, 15, 16, 17, 18, 19 and 20 C atoms such as n-undecyl, n-dodecyl, n-tridecyl, n-tetradecyl, n-pentadecyl, n-hexadecyl, n-heptadecyl, n-octadecyl, n-nonadecyl and n-eicosyl.

The term partially halogenated alkyl group denotes that at least one H atom of the alkyl group is replaced by F, Cl, Br or I. Preferably, the alkyl group is partially fluorinated meaning that at least one H atom of the alkyl group is replaced by F.

The term completely halogenated alkyl group denotes that all H atoms of the alkyl group are replaced by F, Cl, Br and/or I. Preferably, the alkyl group is completely fluorinated meaning that all H atoms of the alkyl group are replaced by F. A preferred completely fluorinated alkyl group is trifluoromethyl.

The term halogenated or preferably fluorinated corresponds additionally to other groups such as a halogenated cycloalkyl group, a halogenated alkoxy group or a halogenated thioalkyl group.

A linear or branched hydroxyalkyl group having 1 to 20 C atoms denotes an alkyl group having 1, 2, 3, 4, 5, 6, 7, 8, 9, 10, 11, 12, 13, 14, 15, 16, 17, 18, 19 or 20 C atoms wherein at least one H atom is replaced by a hydroxyl group (—OH). The hydroxyl group is preferably replaced on the last C atom of the alkyl group, for example hydroxymethyl, 2-hydroxyethyl, 3-hydroxy-propyl, 4-hydroxy-butyl, 5-hydroxy-pentyl, 4-hydroxy-1-, -2- or -3-methylbutyl, 3-hydroxy-1,1-, -1,2- or -2,2-dimethylpropyl, 3-hydroxy-1-ethylpropyl, 6-hydroxy-hexyl, 7-hydroxy-heptyl, 8-hydroxy-octyl, 6-hydroxy-1-ethylhexyl, 9-hydroxy-nonyl, 10-hydroxy-decyl, 11-hydroxy-undecyl, 12-hydroxy-dodecyl, 13-hydroxy-tridecyl, 14-hydroxy-tetradecyl, 15-hydroxy-pentadecyl, 16-hydroxy-hexadecyl, 17-hydroxy-heptadecyl, 18-hydroxy-octadecyl, 19-hydroxy-nonadecyl and 20-hydroxy-eicosyl. Preferred hydroxyalkyl groups are hydroxymethyl and 3-hydroxy-propyl.

A cycloalkyl group having 3 to 6 C atoms includes cyclopropyl, cyclobutyl, cyclopentyl and cyclohexyl which may be partially or completely halogenated or fluorinated as explained before.

A linear or branched alkoxy group having 1 to 20 C atoms denotes an O-alkyl group having 1, 2, 3, 4, 5, 6, 7, 8, 9, 10, 11, 12, 13, 14, 15, 16, 17, 18, 19 or 20 C atoms, for example methoxy, ethoxy, iso-propoxy, n-propoxy, iso-butoxy, n-butoxy, tert-butoxy, n-pentyloxy, 1-, 2- or 3-methylbutyloxy, 1,1-, 1,2- or 2,2-dimethylpropoxy, 1-ethylpropoxy, n-hexyloxy, n-heptyloxy, n-octyloxy, ethylhexyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy and n-eicosyloxy which may be partially or completely halogenated or preferably may be partially or completely fluorinated. A preferred completely fluorinated alkoxy group is trifluoromethoxy.

A linear or branched thioalkyl group having 1 to 20 C atoms denotes a S-alkyl group having 1, 2, 3, 4, 5, 6, 7, 8, 9, 10, 11, 12, 13, 14, 15, 16, 17, 18, 19 or 20 C atoms, for example thiomethyl, 1-thioethyl, 1-thio-iso-propyl, 1-thio-n-propoyl, 1-thio-iso-butyl, 1-thio-n-butyl, 1-thio-tert-butyl, 1-thio-n-pentyl, 1-thio-1-, -2- or -3-methylbutyl, 1-thio-1,1-, -1,2- or -2,2-dimethylpropyl, 1-thio-1-ethylpropyl, 1-thio-n-hexyl, 1-thio-n-heptyl, 1-thio-n-octyl, 1-thio-ethylhexyl, 1-thio-n-nonyl, 1-thio-n-decyl, 1-thio-n-undecyl, 1-thio-n-dodecyl, 1-thio-n-tridecyl, 1-thio-n-tetradecyl, 1-thio-n-pentadecyl, 1-thio-n-hexadecyl, 1-thio-n-heptadecyl, 1-thio-n-octadecyl, 1-thio-n-nonadecyl and 1-thio-n-eicosyl which may be partially or completely halogenated or preferably may be partially or completely fluorinated. A preferred completely fluorinated thioether group is trifluoromethyl thioether.

Preferred alkyl and alkoxy radicals have 1, 2, 3, 4, 5, 6, 7, 8, 9 or 10 C atoms.

A polymerisable group is a group which can be subject to or can undergo polymerization thus forming an oligomer or a polymer. The polymerizable group is generally not restricted within the invention but contains at least one Si atom.

Polymerization is the process of taking individual monomers and chaining them together to make longer units. These longer units are called polymers. The compounds of formula (I), (I-1) and/or (I-2) as described before and preferably described below are suitable monomers.

Within the gist of the invention, the polymerizable group $R_1$ once oligomerized or polymerized thus forms or is part of the backbone of the oligomer or polymer comprising polymerized compounds of formula (I), (I-1) and/or (I-2). The polymerizable groups $R_1$ contain silicon thus forming polysiloxanes or polysilazanes and will be described further below.

The linker —[B]— is selected from the group of formulae (1) to (4), wherein $X_1$, $X_2$, $X_3$, $X_4$ are each independently of each other CR' or N, $X_5$ is each independently O, S, C═O or $NR_0$ and $X_6$ and $X_7$ are each independently CR' or N, wherein R' and $R_0$ have a meaning as described before or preferably described below.

Preferred examples for the linker —[B]— are therefore selected from the group of formulae (B-1) to (B-34), (B-1)

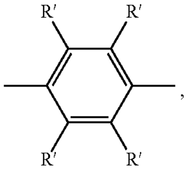

(B-2)

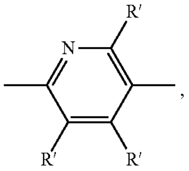

(B-3)

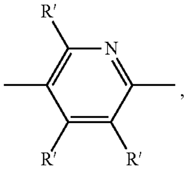

(B-4)

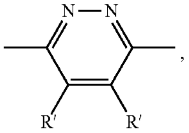

(B-5)

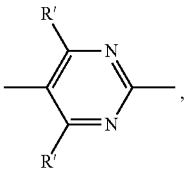

-continued (B-6)

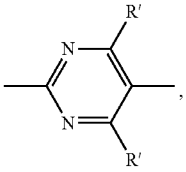

(B-7)

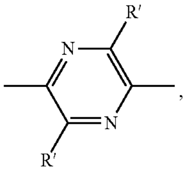

(B-8)

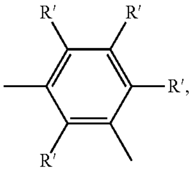

(B-9)

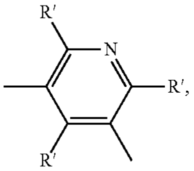

(B-10)

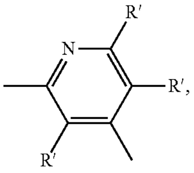

(B-11)

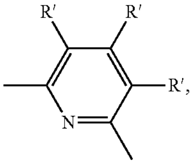

(B-12)

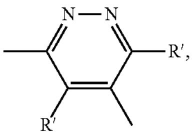

(B-13)

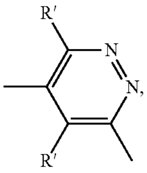

(B-14)

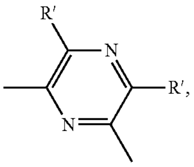

-continued
(B-15)
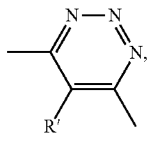
(B-16)
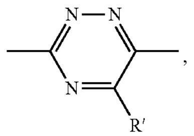
(B-17)
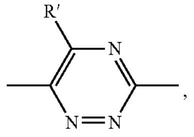
(B-18)
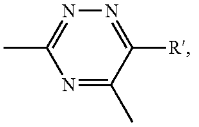
(B-19)
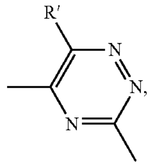
(B-20)
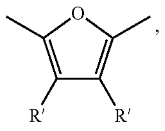
(B-21)
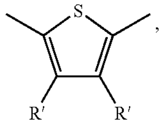
(B-22)
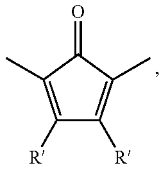
(B-23)
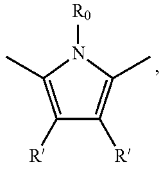
(B-24)
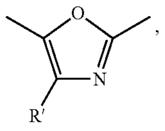
-continued
(B-25)
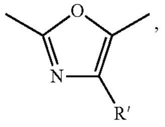
(B-26)
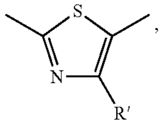
(B-27)
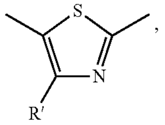
(B-28)
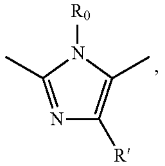
(B-29)
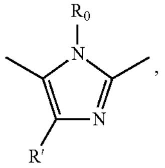
(B-30)
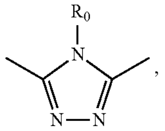
(B-31)
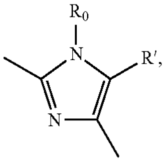
(B-32)
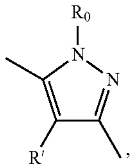
(B-33)
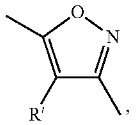
(B-34)
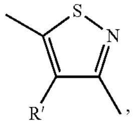
wherein R' and $R_0$ have a meaning as described before or preferably described below.

Compounds of formula (I), (I-1) and/or (I-2) as described before are preferred where the linker —[B]— corresponds to formula (1) or (2) and $X_1$, $X_2$, $X_3$ and $X_4$ have a meaning as described before. Therefore, compounds of formula (I), (I-1) and/or (I-2) are preferred where the linker —[B]— corresponds to formulae (B-1) to (B-19).

The invention therefore relates additionally to compounds of formula (I), (I-1) and/or (I-2) as described before wherein —[B]— corresponds to formula (1) and (2) and $X_1$, $X_2$, $X_3$ and $X_4$ have a meaning as described before.

Compounds of formula (I), (I-1) and/or (I-2) as described before are particularly preferred where the linker —[B]— corresponds to formula (1) or (2) and $X_1$, $X_3$ and $X_4$ are CR' and R' has at each occurrence independently a meaning as described before or preferably described below. Therefore, compounds of formula (I), (I-1) and/or (I-2) are particularly preferred where the linker —[B]— corresponds to formulae (B-1), (B-3), (B-8) or (B-9).

The invention therefore relates additionally to compounds of formula (I), (I-1) and/or (I-2) as described before wherein —[B]— corresponds to formula (1) and (2) and $X_1$, $X_3$ and $X_4$ are CR' and R' has at each occurrence independently a meaning as described before or preferably described below.

Compounds of formula (I), (I-1) and/or (I-2) as described or preferably described before are especially preferred where the linker —[B]— corresponds to formula (1) or (2) and $X_2$ is CR' and R' has at each occurrence independently a meaning as described before or preferably described below. Therefore, compounds of formula (I), (I-1) and/or (I-2) are especially preferred where the linker —[B]— corresponds to formulae (B-1), (B-2), (B-6), (B-7), (B-8), (B-10) or (B-11). Additionally, compounds of formula (I), (I-1) and/or (I-2) having a linker —[B]— which corresponds to formula (B-1) or (B-8) are very particularly preferred and R' has at each occurrence independently a meaning as described before or preferably described below. Within this very particular preferred compounds of formula (I), (I-1) and/or (I-2), it is preferred to select the linker of formula (B-1) and R' has at each occurrence independently a meaning as described before or preferably described below.

The invention therefore relates additionally to compounds of formula (I), (I-1) and/or (I-2) as described or preferably described before wherein —[B]— corresponds to formula (1) and (2) and $X_2$ is CR' and R' has at each occurrence independently a meaning as described before or preferably described below.

R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. It is preferred that at least one R' in —[B] as described before or preferably described before is different from H and is selected from the group consisting of F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. It is particularly preferred that at least two substituents R' are different from H and are independently selected from the group consisting of F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms.

With regard to said substituent R', R' is at each occurrence independently preferably selected from the group consisting of H, F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

It is preferred that at least one R' in —[B]— as described before or preferably described before is different from H and is selected from the group consisting of F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

It is particularly preferred that at least two substituents R' are different from H and are independently selected from the group consisting of F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

R' is at each occurrence independently particularly preferably selected from the group consisting of H, F, methyl, ethyl, n-propyl, n-butyl, n-pentyl, n-hexyl, n-heptyl, n-octyl, trifluormethyl, pentafluorethyl, heptafluorpropyl, methoxy, ethoxy, propoxy, trifluormethoxy, pentafluorethoxy, 2-hydroxyethyl, 3-hydroxy-propyl, 4-hydroxy-butyl and 5-hydroxy-pentyl.

R' is at each occurrence independently very particularly preferably selected from the group consisting of H, F, ethyl, n-pentyl, trifluoromethyl, methoxy and trifluoromethoxy.

Therefore, the invention is further directed to compounds of formula (I), (I-1) and/or (I-2) as described before where —[B]— corresponds to formulae (1) to (4) and wherein at least one R' within $X_1$, $X_2$, $X_3$. $X_4$, $X_6$ or $X_7$ is not H.

Therefore, the invention is further directed to compounds of formula (I), (I-1) and/or (I-2) as described before where —[B]— corresponds to formulae (B-1) to (B-29) or (B-31) to (B-34) or to preferred linkers as described before, wherein at least one R' is not H and $R_0$ have a meaning as described before or preferably described below.

The substituent R' within $X_1$ or $X_3$ in formula (1) is particularly preferred not H and has a meaning as described before.

The substituent R' within $X_7$ in formula (3) is particularly preferred not H and has a meaning as described before.

As described before, the substituents $R_3$, $R_4$, $R_5$ and $R_6$ are at each occurrence independently R' where R' has at each occurrence independently a meaning or a preferred or particularly preferred meaning as described before.

$R_5$ is preferably H or F. $R_5$ is particularly preferably H.

As described before, the substituent $R_7$ corresponds to R' in case m is 0 wherein R' has a meaning or a preferred or particularly preferred meaning as described before. Preferably in case m is 0, $R_7$ corresponds to R' which is not H and has a meaning as described before.

In all cases when R' is preferably not H, it is selected from the preferred group consisting of F, methyl, ethyl, n-propyl, n-butyl, n-pentyl, n-hexyl, n-heptyl, n-octyl, trifluoromethyl, pentafluoroethyl, heptafluoropropyl, methoxy, ethoxy, propoxy, trifluoromethoxy, pentafluoroethoxy, 2-hydroxy-ethyl, 3-hydroxy-propyl, 4-hydroxy-butyl and 5-hydroxy-pentyl or from the particular preferred group consisting of F, ethyl, n-pentyl, trifluoromethyl, methoxy and trifluoromethoxy.

Therefore, the invention is further directed to compounds of formula (I), (I-1) and/or (I-2) as described before where —[B]— corresponds to formulae (1) to (4) and wherein at least one R' within $X_1$, $X_2$, $X_3$, $X_4$, $X_6$ or $X_7$ is not H and $R_7$ is not H in case m is 0.

Therefore, the invention is further directed to compounds of formula (I), (I-1) and/or (I-2) as described before where —[B]— corresponds to formulae (B-1) to (B-29) or (B-31) to (B-34) or to preferred linkers as described before, wherein at least one R' is not H and $R_7$ is not H in case m is 0 and $R_0$ has a meaning as described before or as preferably described below.

As described before, the substituent $R_7$ corresponds to $R_1$ in case m is 1 wherein $R_1$ has a meaning or a preferred meaning as described before or further below. Compounds of formula (I), (I-1) and/or (I-2) in which m is 1 are preferred having a linker —[B]— selected from the group consisting of formula (1) to (4) wherein at least one substituent R' within $X_1$, $X_2$, $X_3$, $X_4$, $X_6$ or $X_7$ is not H and in which at least one substituent $R_3$, $R_4$ or $R_6$ is not H.

Therefore, the invention is further directed to compounds of formula (I), (I-1) and/or (I-2) as described before where —[B]— corresponds to formulae (1) to (4) and wherein at least one R' within $X_1$, $X_2$, $X_3$. $X_4$, $X_6$ or $X_7$ is not H, in which at least one substituent $R_3$, $R_4$ or $R_6$ is not H and $R_7$ corresponds to $R_1$ in case m is 1.

Therefore, the invention is further directed to compounds of formula (I), (I-1) and/or (I-2) as described before where —[B]— corresponds to formulae (B-1) to (B-29) or (B-31) to (B-34) or to preferred linkers as described before, wherein at least one R' is not H, in which at least one substituent $R_3$, $R_4$ or $R_6$ is not H and $R_7$ corresponds to $R_1$ in case m is 1 wherein $R_0$ and $R_1$ has a meaning as described before or further below.

Compounds of formula (I), (I-1) and/or (I-2) with linkers —[B]— as defined before or preferably defined before with the described or preferred substitution pattern on the linker —[B]— and its substituents $R_3$, $R_4$, $R_5$ and $R_6$ as described before or preferably described before are based on a 1-benzopyran-2-one ring system (coumarin or chromene-2-one) in case both X and $X_0$ are O.

Compounds of formula (I), (I-1) and/or (I-2) with linkers —[B]— as defined before or preferably defined before with the described or preferred substitution pattern on the linker —[B]— and its substituents $R_3$, $R_4$, $R_5$ and $R_6$ as described before or preferably described before are based on a 1-benzopyran-2-thione ring system (thiocoumarin or chromene-2-thione) in case X is O and $X_0$ is S.

Compounds of formula (I), (I-1) and/or (I-2) with linkers —[B]— as defined before or preferably defined before with the described or preferred substitution pattern on the linker —[B]— and its substituents $R_3$, $R_4$, $R_5$ and $R_6$ as described before or preferably described before are based on a thiochromene-2-one ring system in case X is S and $X_0$ is O.

Compounds of formula (I), (I-1) and/or (I-2) with linkers —[B]— as defined before or preferably defined before with the described or preferred substitution pattern on the linker —[B]— and its substituents $R_3$, $R_4$, $R_5$ and $R_6$ as described before or preferably described before are based on a thiochromene-2-thione ring in case both X and $X_0$ are S.

Compounds of formula (I), (I-1) and/or (I-2) with linkers —[B]— as defined before or preferably defined before with the described or preferred substitution pattern on the linker —[B]— and its substituents $R_3$, $R_4$, $R_5$ and $R_6$ as described before or preferably described before are based on a quinolin-2-one ring system in case X is $NR_0$ and $X_0$ is O and $R_0$ is independently selected from the group consisting of a linear or branched alkyl group having 1 to 10 C atoms or a cycloalkyl group having 3 to 6 C atoms.

Compounds of formula (I), (I-1) and/or (I-2) with linkers —[B]— as defined before or preferably defined before with the described or preferred substitution pattern on the linker —[B]— and its substituents $R_3$, $R_4$, $R_5$ and $R_6$ as described before or preferably described before are based on a quinolin-2-thione ring system in case X is $NR_0$ and $X_0$ is S and $R_0$ is independently selected from the group consisting of a linear or branched alkyl group having 1 to 10 C atoms or a cycloalkyl group having 3 to 6 C atoms.

$R_0$ is at each occurrence independently preferably methyl, ethyl, iso-propyl, 2-methyl-propyl, n-butyl, n-pentyl, 4-methyl-pentyl or cyclopropyl.

In case X is $NR_0$, $R_0$ is particularly preferably ethyl, iso-propyl, 2-methyl-propyl, n-pentyl or 4-methyl-pentyl.

In case $X_5$ is $NR_0$, $R_0$ is particularly preferably methyl or n-butyl.

In case $X_8$, $X_9$ or $X_{10}$ is $NR_0$, $R_0$ is particularly preferably methyl.

Compounds of formula (I), (I-1) and/or (I-2) with linkers and substituents as described before or preferably described before or below are preferred when X is O or S.

Compounds of formula (I), (I-1) and/or (I-2) with linkers and substituents as described before or preferably described before or below are particularly preferred when $X_0$ is O and X is O or S.

Compounds of formula (I), (I-1) and/or (I-2) with linkers and substituents as described before or preferably described before or below are very particularly preferred when X is O and $X_0$ is O.

In one preferred embodiment of the invention, the compounds of formula (I), (I-1) and/or (I-2) as described before or preferably described before contain one polymerizable group $R_1$. This is the case for compounds of formula (I), (I-1) and/or (I-2) in which n is 1 or m is 1 and the sum of n and m is 1. Such compounds can be preferably used as monomers for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 0 which can preferably be described according to formula (I'), (I')

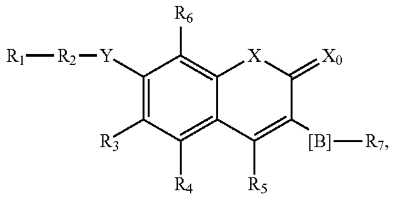

wherein $R_1$, —$R_2$—, Y, $R_3$, $R_4$, $R_5$, $R_6$, X, $X_0$, —[B]— and $R_7$ have a meaning as described before or preferably described before or below.

The invention is therefore additionally directed to compounds of formula (I) wherein n is 0 and m is 1 which can preferably be described according to formula (I"), (I")

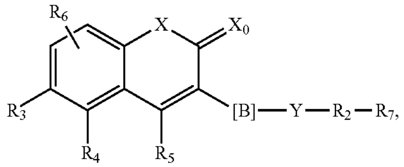

wherein $R_1$, —$R_2$—, Y, $R_3$, $R_4$, $R_5$, $R_6$, X, $X_0$, —[B]— and $R_7$ have a meaning as described before or preferably described before or below.

In another preferred embodiment of the invention, the compounds of formula (I) as described before or preferably described before contain two polymerizable groups $R_1$. This is the case for compounds of formula (I) in which n is 1 and m is 1 and the sum of n and m is 2. Such compounds can be preferably used as cross-linking agent for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 1 which can preferably be described according to formula (I'''), (I''')

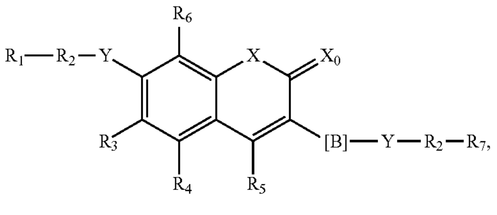

wherein $R_1$, —$R_2$—, Y, $R_3$, $R_4$, $R_5$, $R_6$, X, $X_0$, —[B]— and $R_7$ have a meaning as described before or preferably described before or below.

Compounds of formula (I), (I-1), (I-2) (I'), (I") and (I''') with linkers —[B]— and substituents as described before or preferably described before have a polymerizable group as described before or preferably described before or below and have at least one linking element Y—$R_2$—.

Y is at each occurrence independently O, S or a bond. Y is preferably O. The linking element —$R_2$— is selected from the group consisting of —$(C(R)_2)_o$—, —$(C(R)_2)_p$—$X_8$—$(C(R)_2)_q$—$(X_9)_s$—$(C(R)_2)_r$—$(X_{10})_t$—$(C(R)_2)_u$— and a cycloalkylene group having 5 or 6 C atoms which is substituted with at least one R which is different from H and o is selected from the group consisting of 1 to 20, $X_8$, $X_9$ and $X_{10}$ are at each occurrence O, S or $NR_0$, s and t are at each occurrence independently 0 or 1, p and q are at each occurrence independently selected from the group consisting of 1 to 10, r and u are at each occurrence independently selected from the group consisting of 0 to 10, wherein the overall number of atoms for —$(C(R)_2)_p$—$X_8$—$(C(R)_2)_q$—$(X_9)_s$—$(C(R)_2)_r$—$(X_{10})_t$—$(C(R)_2)_u$—, is up to 20 C atoms.

R is at each occurrence independently selected from the group consisting of H, F, a linear or branched alkyl group having 1 to 8 C atoms or a linear or branched partially or fully fluorinated alkyl group having 1 to 4 C atoms.

R is preferably at each occurrence independently selected from the group consisting of H, F, methyl, ethyl, n-propyl, isopropyl, n-butyl, n-pentyl, isobutyl, ethylhexyl, 2,2,2-trifluoroethyl, 3,3,3-trifluoropropyl, 2,2,3,3,3-pentafluoropropyl, trifluoromethyl, pentafluoroethyl, heptafluoropropyl and nonafluorobutyl. R is particularly preferably at each occurrence independently H, F, methyl, 2,2,2-trifluoroethyl or trifluoromethyl. R is very particularly preferably at each occurrence independently H or F.

Preferably, o is selected from the group consisting of 6 to 12.

Preferably, s is 1.

Preferably t is 0 or 1.

Preferably, $X_8$, $X_9$ and $X_{10}$ are O.

Preferably, p and u are each independently 1, 3, 3, 4, 5 or 6, particularly preferably 1 or 2.

Preferably, q and r are each independently 1, 2 or 3, particularly preferably 1.

Suitable examples for —$R_2$— are —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, —$(CH_2)_{20}$—, —$(CHCH_3)_3$—, —$(CHCH_3)_4$—, —$(CHCH_3)_5$—, —$(CHCH_3)_6$—, —$(CHCH_3)_7$—, —$(CHCH_3)_8$—, —$(CHCH_3)_9$—, —$(CHCH_3)_{10}$—, —$(CHCH_3)_{11}$—, —$(CHCH_3)_{12}$—, —$(CHCH_3)_{13}$—, —$(CHCH_3)_{14}$—, —$(CHCH_3)_{15}$—, —$(CHCH_3)_{16}$—, —$(CHCH_3)_{17}$—, —$(CHCH_3)_{18}$—, —$(CHCH_3)_{19}$—, —$(CHCH_3)_{20}$—, —$(C(CH_3)_2)_2$—, —$(C(CH_3)_2)_3$—, —$(C(CH_3)_2)_4$—, —$(C(CH_3)_2)_5$—, —$(C(CH_3)_2)_6$—, —$(C(CH_3)_2)_7$—, —$(C(CH_3)_2)_8$—, —$(C(CH_3)_2)_9$—, —$(C(CH_3)_2)_{10}$—, —$(C(CH_3)_2)_{11}$—, —$(C(CH_3)_2)_{12}$—, —$(C(CH_3)_2)_{13}$—, —$(C(CH_3)_2)_{14}$—, —$(C(CH_3)_2)_{15}$—, —$(C(CH_3)_2)_{16}$—, —$(C(CH_3)_2)_{17}$—, —$(C(CH_3)_2)_{18}$—, —$(C(CH_3)_2)_{19}$—, —$(C(CH_3)_2)_{20}$—, —$(CHC_2H_5)_2$—, —$(CHC_2H_5)_3$—, —$(CHC_2H_5)_4$—, —$(CHC_2H_5)_5$—, —$(CHC_2H_5)_6$—, —$(CHC_2H_5)_7$—, —$(CHC_2H_5)_8$—, —$(CHC_2H_5)_9$—, —$(CHC_2H_5)_{10}$—, —$(CHC_2H_5)_{11}$—, —$(CHC_2H_5)_{12}$—, —$(CHC_2H_5)_{13}$—, —$(CHC_2H_5)_{14}$—, —$(CHC_2H_5)_{15}$—, —$(CHC_2H_5)_{16}$—, —$(CHC_2H_5)_{17}$—, —$(CHC_2H_5)_{18}$—, —$(CHC_2H_5)_{19}$—, —$(CHC_2H_5)_{20}$—, —$(CH_2)$—$(CHCH_3)$—$(CH_2)$—, —$(CH_2)$—$(CHCH_3)$—$(CH_2)_2$—, —$(CH_2)$—$(CHCH_3)$—$(CH_2)_3$—, —$(CH_2)$—$(CHCH_3)$—$(CH_2)_{11}$—, —$(CH_2)_2$—$(CHCH_3)$—$(CH_2)$—, —$(CH_2)_3$—$(CHCH_3)$—$(CH_2)$—, —$(CH_2)_{11}$—$(CHCH_3)$—$(CH_2)$—, —$(CH_2)_2$—O—$(CH_2)_2$—, —$(CH_2)_3$—O—$(CH_2)_3$—, —$(CH_2)_2$—O—$(CH_2)_2$—O—$(CH_2)_2$—, —$(CH_2)_3$—O—$(CH_2)_3$—O—$(CH_2)_3$—, —$(CH_2)_2$—O—$(CH_2)_2$—O—$(CH_2)_6$—, —$(CH_2)_6$—O—$(CH_2)_2$—O—$(CH_2)_2$—, —$(CH_2)_2$—O—$(CH_2)_2$—O—$(CH_2)_8$—, —$(CH_2)_8$—O—$(CH_2)_2$—O—$(CH_2)_2$—, —$(CH_2)_2$—S—$(CH_2)_2$—, —$(CH_2)_3$—S—$(CH_2)_3$—, —$(CH_2)_2$—S—$(CH_2)_2$—S—$(CH_2)_2$—, —$(CH_2)_3$—S—

$(CH_2)_3$—S—$(CH_2)_3$—, —$(CH_2)_2$—S—$(CH_2)_2$—S—$(CH_2)_6$—, —$(CH_2)_6$—S—$(CH_2)_2$—S—$(CH_2)_2$—, —$(CH_2)_2$—S—$(CH_2)_2$—S—$(CH_2)_8$—, —$(CH_2)_8$—S—$(CH_2)_2$—S—$(CH_2)_2$—, —$(CH_2)_2$—$(NCH_3)$—$(CH_2)_2$—, —$(CH_2)_3$—$(NCH_3)$—$(CH_2)_3$—, —$(CH_2)_2$—$(NCH_3)$—$(CH_2)_2$—$(NCH_3)$—$(CH_2)_2$—, —$(CH_2)_3$—$(NCH_3)$—$(CH_2)_3$—$(NCH_3)$—$(CH_2)_3$—, —$(CH_2)_2$—$(NCH_3)$—$(CH_2)_2$—$(NCH_3)$—$(CH_2)_6$—, —$(CH_2)_6$—$(NCH_3)$—$(CH_2)_2$—$(NCH_3)$—$(CH_2)_2$—, —$(CH_2)_2$—$(NCH_3)$—$(CH_2)_2$—$(NCH_3)$—$(CH_2)_8$— and —$(CH_2)_8$—$(NCH_3)$—$(CH_2)_2$—$(NCH_3)$—$(CH_2)_2$—, —$(CH_2)$—$(CF_2)$—, —$(CH_2)$—$(CF_2)$—$(CH_2)$—, —$(CH_2)$—$(CF_2)$—$(CH_2)_2$—, —$(CH_2)$—$(CF_2)$—$(CH_2)_3$—, —$(CH_2)$—$(CF_2)$—$(CH_2)_4$—, —$(CH_2)$—$(CF_2)$—$(CH_2)_5$—, —$(CH_2)$—$(CF_2)$—$(CH_2)_6$—, —$(CH_2)$—$(CF_2)$—$(CH_2)_7$—, —$(CH_2)$—$(CF_2)$—$(CH_2)_8$—, —$(CH_2)$—$(CF_2)$—$(CH_2)_9$—, —$(CH_2)$—$(CF_2)$—$(CH_2)_{10}$—, —$(CH_2)_2$—$(CF_2)$—$(CH_2)$—, —$(CH_2)_3$—$(CF_2)$—$(CH_2)$—, —$(CH_2)_4$—$(CF_2)$—$(CH_2)$—, —$(CH_2)_5$—$(CF_2)$—$(CH_2)$—, —$(CH_2)_6$—$(CF_2)$—$(CH_2)$—, —$(CH_2)_7$—$(CF_2)$—$(CH_2)$—, —$(CH_2)_8$—$(CF_2)$—$(CH_2)$—, —$(CH_2)_9$—$(CF_2)$—$(CH_2)$—, —$(CH_2)_{10}$—$(CF_2)$—$(CH_2)$—, —$(CH_2)_2$—$(CF_2)$—$(CH_2)_2$—, —$(CH_2)_3$—$(CF_2)$—$(CH_2)_3$—, —$(CH_2)_4$—$(CF_2)$—$(CH_2)_4$—, —$(CH_2)_5$—$(CF_2)$—$(CH_2)_5$—, —$(CH_2)_2$—$(CF_2)$—$(CH_2)$—, —$(CH_2)_2$—$(CF_2)$—$(CH_2)_3$—, —$(CH_2)_2$—$(CF_2)$—$(CH_2)_4$—, —$(CH_2)_2$—$(CF_2)$—$(CH_2)_5$—, —$(CH_2)_2$—$(CF_2)$—$(CH_2)_6$—, —$(CH_2)_2$—$(CF_2)$—$(CH_2)_7$—, —$(CH_2)_2$—$(CF_2)$—$(CH_2)_8$—, —$(CH_2)_2$—$(CF_2)$—$(CH_2)_9$—, —$(CH_2)_3$—$(CF_2)$—$(CH_2)$—, —$(CH_2)_3$—$(CF_2)$—$(CH_2)_2$—, —$(CH_2)_3$—$(CF_2)$—$(CH_2)_4$—, —$(CH_2)_3$—$(CF_2)$—$(CH_2)_5$—, —$(CH_2)_3$—$(CF_2)$—$(CH_2)_6$—, —$(CH_2)_3$—$(CF_2)$—$(CH_2)_7$—, —$(CH_2)_3$—$(CF_2)$—$(CH_2)_8$—, —$(CH_2)_4$—$(CF_2)$—$(CH_2)$—, —$(CH_2)_4$—$(CF_2)$—$(CH_2)_2$—, —$(CH_2)_4$—$(CF_2)$—$(CH_2)_3$—, —$(CH_2)_4$—$(CF_2)$—$(CH_2)_5$—, —$(CH_2)_4$—$(CF_2)$—$(CH_2)_6$—, —$(CH_2)_4$—$(CF_2)$—$(CH_2)_7$—, —$(CH_2)_5$—$(CF_2)$—$(CH_2)$—, —$(CH_2)_5$—$(CF_2)$—$(CH_2)_2$—, —$(CH_2)_5$—$(CF_2)$—$(CH_2)_3$—, —$(CH_2)_5$—$(CF_2)$—$(CH_2)_4$—, —$(CH_2)_5$—$(CF_2)$—$(CH_2)_6$—, —$(CH_2)_6$—$(CF_2)$—$(CH_2)$—, —$(CH_2)_6$—$(CF_2)$—$(CH_2)_2$—, —$(CH_2)_6$—$(CF_2)$—$(CH_2)_3$—, —$(CH_2)_6$—$(CF_2)$—$(CH_2)_4$—, —$(CH_2)_6$—$(CF_2)$—$(CH_2)_5$—, —$(CH_2)$—(CFH)—, —$(CH_2)$—(CFH)—$(CH_2)$—, —$(CH_2)$—(CFH)—$(CH_2)_2$—, —$(CH_2)$—(CFH)—$(CH_2)_3$—, —$(CH_2)$—(CFH)—$(CH_2)_4$—, —$(CH_2)$—(CFH)—$(CH_2)_5$—, —$(CH_2)$—(CFH)—$(CH_2)_6$—, —$(CH_2)$—(CFH)—$(CH_2)_7$—, —$(CH_2)$—(CFH)—$(CH_2)_8$—, —$(CH_2)$—(CFH)—$(CH_2)_9$—, —$(CH_2)$—(CFH)—$(CH_2)_{10}$—, —$(CH_2)_2$—(CFH)—$(CH_2)$—, —$(CH_2)_3$—(CFH)—$(CH_2)$—, —$(CH_2)_4$—(CFH)—$(CH_2)$—, —$(CH_2)_5$—(CFH)—$(CH_2)$—, —$(CH_2)_6$—(CFH)—$(CH_2)$—, —$(CH_2)_7$—(CFH)—$(CH_2)$—, —$(CH_2)_8$—(CFH)—$(CH_2)$—, —$(CH_2)_9$—(CFH)—$(CH_2)$—, —$(CH_2)_{10}$—(CFH)—$(CH_2)$—, —$(CH_2)_2$—(CFH)—$(CH_2)_2$—, —$(CH_2)_3$—(CFH)—$(CH_2)_3$—, —$(CH_2)_4$—(CFH)—$(CH_2)_4$—, —$(CH_2)_5$—(CFH)—$(CH_2)_5$—, —$(CH_2)_2$—(CFH)—$(CH_2)$—, —$(CH_2)_2$—(CFH)—$(CH_2)_3$—, —$(CH_2)_2$—(CFH)—$(CH_2)_4$—, —$(CH_2)_2$—(CFH)—$(CH_2)_5$—, —$(CH_2)_2$—(CFH)—$(CH_2)_6$—, —$(CH_2)_2$—(CFH)—$(CH_2)_7$—, —$(CH_2)_2$—(CFH)—$(CH_2)_8$—, —$(CH_2)_2$—(CFH)—$(CH_2)_9$—, —$(CH_2)_3$—(CFH)—$(CH_2)$—, —$(CH_2)_3$—(CFH)—$(CH_2)_2$—, —$(CH_2)_3$—(CFH)—$(CH_2)_4$—, —$(CH_2)_3$—(CFH)—$(CH_2)_5$—, —$(CH_2)_3$—(CFH)—$(CH_2)_6$—, —$(CH_2)_3$—(CFH)—$(CH_2)_7$—, —$(CH_2)_3$—(CFH)—$(CH_2)_8$—, —$(CH_2)_4$—(CFH)—$(CH_2)$—, —$(CH_2)_4$—(CFH)—$(CH_2)_2$—, —$(CH_2)_4$—(CFH)—$(CH_2)_3$—, —$(CH_2)_4$—(CFH)—$(CH_2)_5$—, —$(CH_2)_4$—(CFH)—$(CH_2)_6$—, —$(CH_2)_4$—(CFH)—$(CH_2)_7$—, —$(CH_2)_5$—(CFH)—$(CH_2)$—, —$(CH_2)_5$—(CFH)—$(CH_2)_2$—, —$(CH_2)_5$—(CFH)—$(CH_2)_3$—, —$(CH_2)_5$—(CFH)—$(CH_2)_4$—, —$(CH_2)_5$—(CFH)—$(CH_2)_6$—, —$(CH_2)_6$—(CFH)—$(CH_2)$—, —$(CH_2)_6$—(CFH)—$(CH_2)_2$—, —$(CH_2)_6$—(CFH)—$(CH_2)_3$—, —$(CH_2)_6$—(CFH)—$(CH_2)_4$—, —$(CH_2)_6$—(CFH)—$(CH_2)_5$—, —$(CH_2)$—$(CF_2)_2$—, —$(CH_2)$—$(CF_2)_2$—$(CH_2)$—, —$(CH_2)$—$(CF_2)_2$—$(CH_2)_2$—, —$(CH_2)$—$(CF_2)_2$—$(CH_2)_3$—, —$(CH_2)$—$(CF_2)_2$—$(CH_2)_4$—, —$(CH_2)$—$(CF_2)_2$—$(CH_2)_5$—, —$(CH_2)$—$(CF_2)_2$—$(CH_2)_6$—, —$(CH_2)$—$(CF_2)_2$—$(CH_2)_7$—, —$(CH_2)$—$(CF_2)_2$—$(CH_2)_8$—, —$(CH_2)$—$(CF_2)_2$—$(CH_2)_9$—, —$(CH_2)_2$—$(CF_2)_2$—$(CH_2)$—, —$(CH_2)_3$—$(CF_2)_2$—$(CH_2)$—, —$(CH_2)_4$—$(CF_2)_2$—$(CH_2)$—, —$(CH_2)_5$—$(CF_2)_2$—$(CH_2)$—, —$(CH_2)_6$—$(CF_2)_2$—$(CH_2)$—, —$(CH_2)_7$—$(CF_2)_2$—$(CH_2)$—, —$(CH_2)_8$—$(CF_2)_2$—$(CH_2)$—, —$(CH_2)_9$—$(CF_2)_2$—$(CH_2)$—, —$(CH_2)_2$—$(CF_2)_2$—$(CH_2)_2$—, —$(CH_2)_3$—$(CF_2)_2$—$(CH_2)_3$—, —$(CH_2)_4$—$(CF_2)_2$—$(CH_2)_4$—, —$(CH_2)_5$—$(CF_2)_2$—$(CH_2)_5$—, —$(CH_2)_2$—$(CF_2)_2$—$(CH_2)$—, —$(CH_2)_2$—$(CF_2)_2$—$(CH_2)_3$—, —$(CH_2)_2$—$(CF_2)_2$—$(CH_2)_4$—, —$(CH_2)_2$—$(CF_2)_2$—$(CH_2)_5$—, —$(CH_2)_2$—$(CF_2)_2$—$(CH_2)_6$—, —$(CH_2)_2$—$(CF_2)_2$—$(CH_2)_7$—, —$(CH_2)_2$—$(CF_2)_2$—$(CH_2)_8$—, —$(CH_2)_3$—$(CF_2)_2$—$(CH_2)$—, —$(CH_2)_3$—$(CF_2)_2$—$(CH_2)_2$—, —$(CH_2)_3$—$(CF_2)_2$—$(CH_2)_4$—, —$(CH_2)_3$—$(CF_2)_2$—$(CH_2)_5$—, —$(CH_2)_3$—$(CF_2)_2$—$(CH_2)_6$—, —$(CH_2)_3$—$(CF_2)_2$—$(CH_2)_7$—, —$(CH_2)_4$—$(CF_2)_2$—$(CH_2)$—, —$(CH_2)_4$—$(CF_2)_2$—$(CH_2)_2$—, —$(CH_2)_4$—$(CF_2)_2$—$(CH_2)_3$—, —$(CH_2)_4$—$(CF_2)_2$—$(CH_2)_5$—, —$(CH_2)_4$—$(CF_2)_2$—$(CH_2)_6$—, —$(CH_2)_5$—$(CF_2)_2$—$(CH_2)$—, —$(CH_2)_5$—$(CF_2)_2$—$(CH_2)_2$—, —$(CH_2)_5$—$(CF_2)_2$—$(CH_2)_3$—, —$(CH_2)_5$—$(CF_2)_2$—$(CH_2)_4$—, —$(CH_2)_6$—$(CF_2)_2$—$(CH_2)$—, —$(CH_2)_6$—$(CF_2)_2$—$(CH_2)_2$—, —$(CH_2)_6$—$(CF_2)_2$—$(CH_2)_3$—, —$(CH_2)_6$—$(CF_2)_2$—$(CH_2)_4$—, —$(CH_2)$—$(CFH)_2$—, —$(CH_2)$—$(CFH)_2$—$(CH_2)$—, —$(CH_2)$—$(CFH)_2$—$(CH_2)_2$—, —$(CH_2)$—$(CFH)_2$—$(CH_2)_3$—, —$(CH_2)$—$(CFH)_2$—$(CH_2)_4$—, —$(CH_2)$—$(CFH)_2$—$(CH_2)_5$—, —$(CH_2)$—$(CFH)_2$—$(CH_2)_6$—, —$(CH_2)$—$(CFH)_2$—$(CH_2)_7$—, —$(CH_2)$—$(CFH)_2$—$(CH_2)_8$—, —$(CH_2)$—$(CFH)_2$—$(CH_2)_9$—, —$(CH_2)_2$—$(CFH)_2$—$(CH_2)$—, —$(CH_2)_3$—$(CFH)_2$—$(CH_2)$—, —$(CH_2)_4$—$(CFH)_2$—$(CH_2)$—, —$(CH_2)_5$—$(CFH)_2$—$(CH_2)$—, —$(CH_2)_6$—$(CFH)_2$—$(CH_2)$—, —$(CH_2)_7$—$(CFH)_2$—$(CH_2)$—, —$(CH_2)_8$—$(CFH)_2$—$(CH_2)$—, —$(CH_2)_9$—$(CFH)_2$—$(CH_2)$—, —$(CH_2)_2$—$(CFH)_2$—$(CH_2)_2$—, —$(CH_2)_3$—$(CFH)_2$—$(CH_2)_3$—, —$(CH_2)_4$—$(CFH)_2$—$(CH_2)_4$—, —$(CH_2)_5$—$(CFH)_2$—$(CH_2)_5$—, —$(CH_2)_2$—$(CFH)_2$—$(CH_2)$—, —$(CH_2)_2$—$(CFH)_2$—$(CH_2)_3$—, —$(CH_2)_2$—$(CFH)_2$—$(CH_2)_4$—, —$(CH_2)_2$—$(CFH)_2$—$(CH_2)_5$—, —$(CH_2)_2$—$(CFH)_2$—$(CH_2)_6$—, —$(CH_2)_2$—$(CFH)_2$—$(CH_2)_7$—, —$(CH_2)_2$—$(CFH)_2$—$(CH_2)_8$—, —$(CH_2)_3$—$(CFH)_2$—$(CH_2)$—, —$(CH_2)_3$—$(CFH)_2$—$(CH_2)_2$—, —$(CH_2)_3$—$(CFH)_2$—$(CH_2)_4$—, —$(CH_2)_3$—$(CFH)_2$—$(CH_2)_5$—, —$(CH_2)_3$—$(CFH)_2$—$(CH_2)_6$—, —$(CH_2)_3$—$(CFH)_2$—$(CH_2)_7$—, —$(CH_2)_4$—$(CFH)_2$—$(CH_2)$—, —$(CH_2)_4$—$(CFH)_2$—$(CH_2)_2$—, —$(CH_2)_4$—$(CFH)_2$—$(CH_2)_3$—, —$(CH_2)_4$—$(CFH)_2$—$(CH_2)_5$—, —$(CH_2)_4$—$(CFH)_2$—$(CH_2)_6$—, —$(CH_2)_5$—$(CFH)_2$—$(CH_2)$—, —$(CH_2)_5$—$(CFH)_2$—$(CH_2)_2$—, —$(CH_2)_5$—$(CFH)_2$—$(CH_2)_3$—, —$(CH_2)_5$—$(CFH)_2$—$(CH_2)_4$—, —$(CH_2)_6$—$(CFH)_2$—$(CH_2)$—, —$(CH_2)_6$—$(CFH)_2$—$(CH_2)_2$—, —$(CH_2)_6$—$(CFH)_2$—$(CH_2)_3$—, —$(CH_2)_6$—$(CFH)_2$—$(CH_2)_4$—, —$(CH_2)$—$(CF_2)_3$—, —$(CH_2)$—$(CF_2)_3$—$(CH_2)$—, —$(CH_2)$—$(CF_2)_3$—$(CH_2)_2$—, —$(CH_2)$—$(CF_2)_3$—$(CH_2)_3$—, —$(CH_2)$—$(CF_2)_3$—$(CH_2)_4$—, —$(CH_2)$—$(CF_2)_3$—$(CH_2)_5$—, —$(CH_2)$—$(CF_2)_3$—$(CH_2)_6$ —, $—(CH_2)—(CF_2)_3—(CH_2)_7—$, $—(CH_2)—(CF_2)_3—(CH_2)_8—$, $—(CH_2)_2—(CF_2)_3—(CH_2)—$, $—(CH_2)_3—(CF_2)_3—(CH_2)—$, $—(CH_2)_4—(CF_2)_3—(CH_2)—$, $—(CH_2)_5—(CF_2)_3—(CH_2)—$, $—(CH_2)_6—(CF_2)_3—(CH_2)—$, $—(CH_2)_7—(CF_2)_3—(CH_2)—$, $—(CH_2)_8—(CF_2)_3—(CH_2)—$, $—(CH_2)_2—(CF_2)_3—(CH_2)_2—$, $—(CH_2)_3—(CF_2)_3—(CH_2)_3—$, $—(CH_2)_4—(CF_2)_3—(CH_2)_4—$, $—(CH_2)_2—(CF_2)_3—(CH_2)—$, $—(CH_2)_2—(CF_2)_3—(CH_2)_3—$, $—(CH_2)_2—(CF_2)_3—(CH_2)_4—$, $—(CH_2)_2—(CF_2)_3—(CH_2)_5—$, $—(CH_2)_2—(CF_2)_3—(CH_2)_6—$, $—(CH_2)_2—(CF_2)_3—(CH_2)_7—$, $—(CH_2)_3—(CF_2)_3—(CH_2)—$, $—(CH_2)_3—(CF_2)_3—(CH_2)_2—$, $—(CH_2)_3—(CF_2)_3—(CH_2)_4—$, $—(CH_2)_3—(CF_2)_3—(CH_2)_5—$, $—(CH_2)_3—(CF_2)_3—(CH_2)_6—$, $—(CH_2)_4—(CF_2)_3—(CH_2)—$, $—(CH_2)_4—(CF_2)_3—(CH_2)_2—$, $—(CH_2)_4—(CF_2)_3—(CH_2)_3—$, $—(CH_2)_4—(CF_2)_3—(CH_2)_5—$, $—(CH_2)_5—(CF_2)_3—(CH_2)—$, $—(CH_2)_5—(CF_2)_3—(CH_2)_2—$, $—(CH_2)_5—(CF_2)_3—(CH_2)_3—$, $—(CH_2)_5—(CF_2)_3—(CH_2)_4—$, $(CH_2)_6—(CF_2)_3—(CH_2)—$, $—(CH_2)_6—(CF_2)_3—(CH_2)_2—$, $—(CH_2)_6—(CF_2)_3—(CH_2)_3—$, $—(CH_2)—(CF_2)_4—$, $—(CH_2)—(CF_2)_4—(CH_2)—$, $—(CH_2)—(CF_2)_4—(CH_2)_2—$, $—(CH_2)—(CF_2)_4—(CH_2)_3—$, $—(CH_2)—(CF_2)_4—(CH_2)_4—$, $—(CH_2)—(CF_2)_4—(CH_2)_5—$, $—(CH_2)—(CF_2)_4—(CH_2)_6—$, $—(CH_2)—(CF_2)_4—(CH_2)_7—$, $—(CH_2)—(CF_2)_4—(CH_2)_8—$, $—(CH_2)—(CF_2)_4—(CH_2)_9—$, $—(CH_2)—(CF_2)_4—(CH_2)_{10}—$, $—(CH_2)_2—(CF_2)_4—(CH_2)—$, $—(CH_2)_3—(CF_2)_4—(CH_2)—$, $—(CH_2)_4—(CF_2)_4—(CH_2)—$, $—(CH_2)_5—(CF_2)_4—(CH_2)—$, $—(CH_2)_6—(CF_2)_4—(CH_2)—$, $—(CH_2)_7—(CF_2)_4—(CH_2)—$, $—(CH_2)_2—(CF_2)_4—(CH_2)_2—$, $—(CH_2)_3—(CF_2)_4—(CH_2)_3—$, $—(CH_2)_4—(CF_2)_4—(CH_2)_4—$, $—(CH_2)_5—(CF_2)_4—(CH_2)_5—$, $—(CH_2)_2—(CF_2)_4—(CH_2)_3—$, $—(CH_2)_2—(CF_2)_4—(CH_2)_4—$, $—(CH_2)_2—(CF_2)_4—(CH_2)_5—$, $—(CH_2)_2—(CF_2)_4—(CH_2)_6—$, $—(CH_2)_3—(CF_2)_4—(CH_2)_2—$, $—(CH_2)_3—(CF_2)_4—(CH_2)_4—$, $—(CH_2)_4—(CF_2)_4—(CH_2)_2—$, $—(CH_2)_4—(CF_2)_4—(CH_2)_3—$, $—(CH_2)_5—(CF_2)_4—(CH_2)_2—$, $—(CH_2)_5—(CF_2)_4—(CH_2)_3—$, $—(CH_2)_6—(CF_2)_4—(CH_2)_2—$, $—(CH_2)—(CF_2)_5—$, $—(CH_2)—(CF_2)_5—(CH_2)—$, $—(CH_2)—(CF_2)_5—(CH_2)_2—$, $—(CH_2)—(CF_2)_5—(CH_2)_3—$, $—(CH_2)—(CF_2)_5—(CH_2)_4—$, $—(CH_2)—(CF_2)_5—(CH_2)_5—$, $—(CH_2)—(CF_2)_5—(CH_2)_6—$, $—(CH_2)_2—(CF_2)_5—(CH_2)—$, $—(CH_2)_3—(CF_2)_5—(CH_2)—$, $—(CH_2)_4—(CF_2)_5—(CH_2)—$, $—(CH_2)_5—(CF_2)_5—(CH_2)—$, $—(CH_2)_6—(CF_2)_5—(CH_2)—$, $—(CH_2)_2—(CF_2)_5—(CH_2)_2—$, $—(CH_2)_3—(CF_2)_5—(CH_2)_3—$, $—(CH_2)_4—(CF_2)_5—(CH_2)_4—$, $—(CH_2)_2—(CF_2)_5—(CH_2)_3—$, $—(CH_2)_2—(CF_2)_5—(CH_2)_4—$, $—(CH_2)_2—(CF_2)_5—(CH_2)_5—$, $—(CH_2)_2—(CF_2)_5—(CH_2)_6—$, $—(CH_2)_3—(CF_2)_5—(CH_2)_2—$, $—(CH_2)_3—(CF_2)_5—(CH_2)_4—$, $—(CH_2)_4—(CF_2)_5—(CH_2)_2—$, $—(CH_2)_4—(CF_2)_5—(CH_2)_3—$, $—(CH_2)_5—(CF_2)_5—(CH_2)_2—$, $—(CH_2)—(CHCF_3)—$, $—(CH_2)—(CHCF_3)—(CH_2)—$, $—(CH_2)—(CHCF_3)—(CH_2)_2—$, $—(CH_2)—(CHCF_3)—(CH_2)_3—$, $—(CH_2)—(CHCF_3)—(CH_2)_4—$, $—(CH_2)—(CHCF_3)—(CH_2)_5—$, $—(CH_2)—(CHCF_3)—(CH_2)_6—$, $—(CH_2)—(CHCF_3)—(CH_2)_7—$, $—(CH_2)—(CHCF_3)—(CH_2)_8—$, $—(CH_2)—(CHCF_3)—(CH_2)_9—$, $—(CH_2)—(CHCF_3)—(CH_2)_{10}—$, $—(CH_2)_2—(CHCF_3)—(CH_2)—$, $—(CH_2)_3—(CHCF_3)—(CH_2)—$, $—(CH_2)_4—(CHCF_3)—(CH_2)—$, $—(CH_2)_5—(CHCF_3)—(CH_2)—$, $—(CH_2)_6—(CHCF_3)—(CH_2)—$, $—(CH_2)_7—(CHCF_3)—(CH_2)—$, $—(CH_2)_8—(CHCF_3)—(CH_2)—$, $—(CH_2)_9—(CHCF_3)—(CH_2)—$, $—(CH_2)_{10}—(CHCF_3)—(CH_2)—$, $—(CH_2)_2—(CHCF_3)—(CH_2)_2—$, $—(CH_2)_3—(CHCF_3)—(CH_2)_3—$, $—(CH_2)_4—(CHCF_3)—(CH_2)_4—$, $—(CH_2)_5—(CHCF_3)—(CH_2)_5—$, $—(CH_2)_2—(CHCF_3)—(CH_2)_3—$, $—(CH_2)_2—(CHCF_3)—(CH_2)_4—$, $—(CH_2)_2—(CHCF_3)—(CH_2)_5—$, $—(CH_2)_2—(CHCF_3)—(CH_2)_6—$, $—(CH_2)_2—(CHCF_3)—(CH_2)_7—$, $—(CH_2)_2—(CHCF_3)—(CH_2)_8—$, $—(CH_2)_2—(CHCF_3)—(CH_2)_9—$, $—(CH_2)_3—(CHCF_3)—(CH_2)_2—$, $—(CH_2)_3—(CHCF_3)—(CH_2)_4—$, $—(CH_2)_3—(CHCF_3)—(CH_2)_5—$, $—(CH_2)_3—(CHCF_3)—(CH_2)_6—$, $—(CH_2)_3—(CHCF_3)—(CH_2)_7—$, $—(CH_2)_3—(CHCF_3)—(CH_2)_8—$, $—(CH_2)_4—(CHCF_3)—(CH_2)_2—$, $—(CH_2)_4—(CHCF_3)—(CH_2)_3—$, $—(CH_2)_4—(CHCF_3)—(CH_2)_5—$, $—(CH_2)_4—(CHCF_3)—(CH_2)_6—$, $—(CH_2)_4—(CHCF_3)—(CH_2)_7—$, $—(CH_2)_5—(CHCF_3)—(CH_2)_2—$, $—(CH_2)_5—(CHCF_3)—(CH_2)_3—$, $—(CH_2)_5—(CHCF_3)—(CH_2)_4—$, $—(CH_2)_5—(CHCF_3)—(CH_2)_6—$, $—(CH_2)_6—(CHCF_3)—(CH_2)_2—$, $—(CH_2)_6—(CHCF_3)—(CH_2)_3—$, $—(CH_2)_6—(CHCF_3)—(CH_2)_4—$, $—(CH_2)_6—(CHCF_3)—(CH_2)_5—$, $—(CH_2)—(CHCF_3)_2—$, $—(CH_2)—(CHCF_3)_2—(CH_2)—$, $—(CH_2)—(CHCF_3)_2—(CH_2)_2—$, $—(CH_2)—(CHCF_3)_2—(CH_2)_3—$, $—(CH_2)—(CHCF_3)_2—(CH_2)_4—$, $—(CH_2)—(CHCF_3)_2—(CH_2)_5—$, $—(CH_2)—(CHCF_3)_2—(CH_2)_6—$, $—(CH_2)—(CHCF_3)_2—(CH_2)_7—$, $—(CH_2)—(CHCF_3)_2—(CH_2)_8—$, $—(CH_2)—(CHCF_3)_2—(CH_2)_9—$, $—(CH_2)_2—(CHCF_3)_2—(CH_2)—$, $—(CH_2)_3—(CHCF_3)_2—(CH_2)—$, $—(CH_2)_4—(CHCF_3)_2—(CH_2)—$, $—(CH_2)_5—(CHCF_3)_2—(CH_2)—$, $—(CH_2)_6—(CHCF_3)_2—(CH_2)—$, $—(CH_2)_7—(CHCF_3)_2—(CH_2)—$, $—(CH_2)_8—(CHCF_3)_2—(CH_2)—$, $—(CH_2)_9—(CHCF_3)_2—(CH_2)—$, $—(CH_2)_2—(CHCF_3)_2—(CH_2)_2—$, $—(CH_2)_3—(CHCF_3)_2—(CH_2)_3—$, $—(CH_2)_4—(CHCF_3)_2—(CH_2)_4—$, $—(CH_2)_5—(CHCF_3)_2—(CH_2)_5—$, $—(CH_2)_2—(CHCF_3)_2—(CH_2)_3—$, $—(CH_2)_2—(CHCF_3)_2—(CH_2)_4—$, $—(CH_2)_2—(CHCF_3)_2—(CH_2)_5—$, $—(CH_2)_2—(CHCF_3)_2—(CH_2)_6—$, $—(CH_2)_2—(CHCF_3)_2—(CH_2)_7—$, $—(CH_2)_2—(CHCF_3)_2—(CH_2)_8—$, $—(CH_2)_3—(CHCF_3)_2—(CH_2)_2—$, $—(CH_2)_3—(CHCF_3)_2—(CH_2)_4—$, $—(CH_2)_3—(CHCF_3)_2—(CH_2)_5—$, $—(CH_2)_3—(CHCF_3)_2—(CH_2)_6—$, $—(CH_2)_3—(CHCF_3)_2—(CH_2)_7—$, $—(CH_2)_4—(CHCF_3)_2—(CH_2)_2—$, $—(CH_2)_4—(CHCF_3)_2—(CH_2)_3—$, $—(CH_2)_4—(CHCF_3)_2—(CH_2)_5—$, $—(CH_2)_4—(CHCF_3)_2—(CH_2)_6—$, $—(CH_2)_5—(CHCF_3)_2—(CH_2)_2—$, $—(CH_2)_5—(CHCF_3)_2—(CH_2)_3—$, $—(CH_2)_5—(CHCF_3)_2—(CH_2)_4—$, $—(CH_2)_6—(CHCF_3)_2—(CH_2)_2—$, $—(CH_2)_6—(CHCF_3)_2—(CH_2)_3—$, $—(CH_2)_6—(CHCF_3)_2—(CH_2)_4—$, $—(CH_2)—(CHCF_3)_3—$, $—(CH_2)—(CHCF_3)_3—(CH_2)—$, $—(CH_2)—(CHCF_3)_3—(CH_2)_2—$, $—(CH_2)—(CHCF_3)_3—(CH_2)_3—$, $—(CH_2)—(CHCF_3)_3—(CH_2)_4—$, $—(CH_2)—(CHCF_3)_3—(CH_2)_5—$, $—(CH_2)—(CHCF_3)_3—(CH_2)_6—$, $—(CH_2)—(CHCF_3)_3—(CH_2)_7—$, $—(CH_2)—(CHCF_3)_3—(CH_2)_8—$, $—(CH_2)_2—(CHCF_3)_3—(CH_2)—$, $—(CH_2)_3—(CHCF_3)_3—(CH_2)—$, $—(CH_2)_4—(CHCF_3)_3—(CH_2)—$, $—(CH_2)_5—(CHCF_3)_3—(CH_2)—$, $—(CH_2)_6—(CHCF_3)_3—(CH_2)—$, $—(CH_2)_7—(CHCF_3)_3—(CH_2)—$, $—(CH_2)_8—(CHCF_3)_3—(CH_2)—$, $—(CH_2)_2—(CHCF_3)_3—(CH_2)_2—$, $—(CH_2)_3—(CHCF_3)_3—(CH_2)_3—$, $—(CH_2)_4—(CHCF_3)_3—(CH_2)_4—$, $—(CH_2)_2—(CHCF_3)_3—(CH_2)_3—$, $—(CH_2)_2—(CHCF_3)_3—(CH_2)_4—$, $—(CH_2)_2—(CHCF_3)_3—(CH_2)_5—$, $—(CH_2)_2—(CHCF_3)_3—(CH_2)_6—$, $—(CH_2)_2—(CHCF_3)_3—(CH_2)_7—$, $—(CH_2)_3—(CHCF_3)_3—(CH_2)_2—$, $—(CH_2)_3—(CHCF_3)_3—(CH_2)_4—$, $—(CH_2)_3—(CHCF_3)_3—(CH_2)_5—$, $—(CH_2)_3—(CHCF_3)_3—(CH_2)_6—$, $—(CH_2)_4—(CHCF_3)_3—(CH_2)_2—$, $—(CH_2)_4—(CHCF_3)_3—(CH_2)_3—$, $—(CH_2)_4—(CHCF_3)_3—(CH_2)_5—$, $—(CH_2)_5—(CHCF_3)_3—(CH_2)_2—$, $—(CH_2)_5—(CHCF_3)_3—(CH_2)_3—$, $—(CH_2)_5—(CHCF_3)_3—(CH_2)_4—$, $—(CH_2)_6—(CHCF_3)_3—(CH_2)_2—$, $—(CH_2)_6—(CHCF_3)_3—(CH_2)_3—$, $—(CH_2)—(CHCF_3)_4—$, $—(CH_2)—(CHCF_3)_4—(CH_2)—$, $—(CH_2)—(CHCF_3)_4—(CH_2)_2—$, $—(CH_2)—(CHCF_3)_4—(CH_2)_3—$, $—(CH_2)—(CHCF_3)_4—(CH_2)_4—$, $—(CH_2)—(CHCF_3)_4—(CH_2)_5—$, $—(CH_2)—(CHCF_3)_4—(CH_2)_6—$, $-(CH_2)-(CHCF_3)_4-(CH_2)_7-$, $-(CH_2)-(CHCF_3)_4-(CH_2)_8-$, $-(CH_2)-(CHCF_3)_4-(CH_2)_9-$, $-(CH_2)-(CHCF_3)_4-(CH_2)_{10}-$, $-(CH_2)_2-(CHCF_3)_4-(CH_2)-$, $-(CH_2)_3-(CHCF_3)_4-(CH_2)-$, $-(CH_2)_4-(CHCF_3)_4-(CH_2)-$, $-(CH_2)_5-(CHCF_3)_4-(CH_2)-$, $-(CH_2)_6-(CHCF_3)_4-(CH_2)-$, $-(CH_2)_7-(CHCF_3)_4-(CH_2)-$, $-(CH_2)_2-(CHCF_3)_4-(CH_2)_2-$, $-(CH_2)_3-(CHCF_3)_4-(CH_2)_3-$, $-(CH_2)_4-(CHCF_3)_4-(CH_2)_4-$, $-(CH_2)_5-(CHCF_3)_4-(CH_2)_5-$, $-(CH_2)_2-(CHCF_3)_4-(CH_2)_3-$, $-(CH_2)_2-(CHCF_3)_4-(CH_2)_4-$, $-(CH_2)_2-(CHCF_3)_4-(CH_2)_5-$, $-(CH_2)_2-(CHCF_3)_4-(CH_2)_6-$, $-(CH_2)_3-(CHCF_3)_4-(CH_2)_2-$, $-(CH_2)_3-(CHCF_3)_4-(CH_2)_4-$, $-(CH_2)_4-(CHCF_3)_4-(CH_2)_2-$, $-(CH_2)_4-(CHCF_3)_4-(CH_2)_3-$, $-(CH_2)_5-(CHCF_3)_4-(CH_2)_2-$, $-(CH_2)_5-(CHCF_3)_4-(CH_2)_3-$, $-(CH_2)_6-(CHCF_3)_4-(CH_2)_2-$, $-(CH_2)-(CHCF_3)_5-$, $-(CH_2)-(CHCF_3)_5-(CH_2)-$, $-(CH_2)-(CHCF_3)_5-(CH_2)_2-$, $-(CH_2)-(CHCF_3)_5-(CH_2)_3-$, $-(CH_2)-(CHCF_3)_5-(CH_2)_4-$, $-(CH_2)-(CHCF_3)_5-(CH_2)_5-$, $-(CH_2)-(CHCF_3)_5-(CH_2)_6-$, $-(CH_2)_2-(CHCF_3)_5-(CH_2)-$, $-(CH_2)_3-(CHCF_3)_5-(CH_2)-$, $-(CH_2)_4-(CHCF_3)_5-(CH_2)-$, $-(CH_2)_5-(CHCF_3)_5-(CH_2)-$, $-(CH_2)_6-(CHCF_3)_5-(CH_2)-$, $-(CH_2)_2-(CHCF_3)_5-(CH_2)_2-$, $-(CH_2)_3-(CHCF_3)_5-(CH_2)_3-$, $-(CH_2)_4-(CHCF_3)_5-(CH_2)_4-$, $-(CH_2)_2-(CHCF_3)_5-(CH_2)_3-$, $-(CH_2)_2-(CHCF_3)_5-(CH_2)_4-$, $-(CH_2)_2-(CHCF_3)_5-(CH_2)_5-$, $-(CH_2)_2-(CHCF_3)_5-(CH_2)_6-$, $-(CH_2)_3-(CHCF_3)_5-(CH_2)_2-$, $-(CH_2)_3-(CHCF_3)_5-(CH_2)_4-$, $-(CH_2)_4-(CHCF_3)_5-(CH_2)_2-$, $-(CH_2)_4-(CHCF_3)_5-(CH_2)_3-$, $-(CH_2)_5-(CHCF_3)_5-(CH_2)_2-$, $-(CH_2)-[C(CH_3)CF_3]-$, $-(CH_2)-[C(CH_3)CF_3]-(CH_2)-$, $-(CH_2)-[C(CH_3)CF_3]-(CH_2)_2-$, $-(CH_2)-[C(CH_3)CF_3]-(CH_2)_3-$, $-(CH_2)-[C(CH_3)CF_3]-(CH_2)_4-$, $-(CH_2)-[C(CH_3)CF_3]-(CH_2)_5-$, $-(CH_2)-[C(CH_3)CF_3]-(CH_2)_6-$, $-(CH_2)-[C(CH_3)CF_3]-(CH_2)_7-$, $-(CH_2)-[C(CH_3)CF_3]-(CH_2)_8-$, $-(CH_2)-[C(CH_3)CF_3]-(CH_2)_9-$, $-(CH_2)-[C(CH_3)CF_3]-(CH_2)_{10}-$, $-(CH_2)_2-[C(CH_3)CF_3]-(CH_2)-$, $-(CH_2)_3-[C(CH_3)CF_3]-(CH_2)-$, $-(CH_2)_4-[C(CH_3)CF_3]-(CH_2)-$, $-(CH_2)_5-[C(CH_3)CF_3]-(CH_2)-$, $-(CH_2)_6-[C(CH_3)CF_3]-(CH_2)-$, $-(CH_2)_7-[C(CH_3)CF_3]-(CH_2)-$, $-(CH_2)_8-[C(CH_3)CF_3]-(CH_2)-$, $-(CH_2)_9-[C(CH_3)CF_3]-(CH_2)-$, $-(CH_2)_{10}-[C(CH_3)CF_3]-(CH_2)-$, $-(CH_2)_2-[C(CH_3)CF_3]-(CH_2)_2-$, $-(CH_2)_3-[C(CH_3)CF_3]-(CH_2)_3-$, $-(CH_2)_4-[C(CH_3)CF_3]-(CH_2)_4-$, $-(CH_2)_5-[C(CH_3)CF_3]-(CH_2)_5-$, $-(CH_2)_2-[C(CH_3)CF_3]-(CH_2)_3-$, $-(CH_2)_2-[C(CH_3)CF_3]-(CH_2)_4-$, $-(CH_2)_2-[C(CH_3)CF_3]-(CH_2)_5-$, $-(CH_2)_2-[C(CH_3)CF_3]-(CH_2)_6-$, $-(CH_2)_2-[C(CH_3)CF_3]-(CH_2)_7-$, $-(CH_2)_2-[C(CH_3)CF_3]-(CH_2)_8-$, $-(CH_2)_2-[C(CH_3)CF_3]-(CH_2)_9-$, $-(CH_2)_3-[C(CH_3)CF_3]-(CH_2)_2-$, $-(CH_2)_3-[C(CH_3)CF_3]-(CH_2)_4-$, $-(CH_2)_3-[C(CH_3)CF_3]-(CH_2)_5-$, $-(CH_2)_3-[C(CH_3)CF_3]-(CH_2)_6-$, $-(CH_2)_3-[C(CH_3)CF_3]-(CH_2)_7-$, $-(CH_2)_3-[C(CH_3)CF_3]-(CH_2)_8-$, $-(CH_2)_4-[C(CH_3)CF_3]-(CH_2)_2-$, $-(CH_2)_4-[C(CH_3)CF_3]-(CH_2)_3-$, $-(CH_2)_4-[C(CH_3)CF_3]-(CH_2)_5-$, $-(CH_2)_4-[C(CH_3)CF_3]-(CH_2)_6-$, $-(CH_2)_4-[C(CH_3)CF_3]-(CH_2)_7-$, $-(CH_2)_5-[C(CH_3)CF_3]-(CH_2)_2-$, $-(CH_2)_5-[C(CH_3)CF_3]-(CH_2)_3-$, $-(CH_2)_5-[C(CH_3)CF_3]-(CH_2)_4-$, $-(CH_2)_5-[C(CH_3)CF_3]-(CH_2)_6-$, $-(CH_2)_6-[C(CH_3)CF_3]-(CH_2)_2-$, $-(CH_2)_6-[C(CH_3)CF_3]-(CH_2)_3-$, $-(CH_2)_6-[C(CH_3)CF_3]-(CH_2)_4-$, $-(CH_2)_6-[C(CH_3)CF_3]-(CH_2)_5-$, $-(CH_2)-[C(CH_3)CF_3]_2-$, $-(CH_2)-[C(CH_3)CF_3]_2-(CH_2)-$, $-(CH_2)-[C(CH_3)CF_3]_2-(CH_2)_2-$, $-(CH_2)-[C(CH_3)CF_3]_2-(CH_2)_3-$, $-(CH_2)-[C(CH_3)CF_3]_2-(CH_2)_4-$, $-(CH_2)-[C(CH_3)CF_3]_2-(CH_2)_5-$, $-(CH_2)-[C(CH_3)CF_3]_2-(CH_2)_6-$, $-(CH_2)-[C(CH_3)CF_3]_2-(CH_2)_7-$, $-(CH_2)-[C(CH_3)CF_3]_2-(CH_2)_8-$, $-(CH_2)-[C(CH_3)CF_3]_2-(CH_2)_9-$, $-(CH_2)_2-[C(CH_3)CF_3]_2-(CH_2)-$, $-(CH_2)_3-[C(CH_3)CF_3]_2-(CH_2)-$, $-(CH_2)_4-[C(CH_3)CF_3]_2-(CH_2)-$, $-(CH_2)_5-[C(CH_3)CF_3]_2-(CH_2)-$, $-(CH_2)_6-[C(CH_3)CF_3]_2-(CH_2)-$, $-(CH_2)_7-[C(CH_3)CF_3]_2-(CH_2)-$, $-(CH_2)_8-[C(CH_3)CF_3]_2-(CH_2)-$, $-(CH_2)_3-[C(CH_3)CF_3]_2-(CH_2)-$, $-(CH_2)_2-[C(CH_3)CF_3]_2-(CH_2)_2-$, $-(CH_2)_3-[C(CH_3)CF_3]_2-(CH_2)_3-$, $-(CH_2)_4-[C(CH_3)CF_3]_2-(CH_2)_4-$, $-(CH_2)_5-[C(CH_3)CF_3]_2-(CH_2)_5-$, $-(CH_2)_2-[C(CH_3)CF_3]_2-(CH_2)_3-$, $-(CH_2)_2-[C(CH_3)CF_3]_2-(CH_2)_4-$, $-(CH_2)_2-[C(CH_3)CF_3]_2-(CH_2)_5-$, $-(CH_2)_2-[C(CH_3)CF_3]_2-(CH_2)_6-$, $-(CH_2)_2-[C(CH_3)CF_3]_2-(CH_2)_7-$, $-(CH_2)_2-[C(CH_3)CF_3]_2-(CH_2)_8-$, $-(CH_2)_3-[C(CH_3)CF_3]_2-(CH_2)_2-$, $-(CH_2)_3-[C(CH_3)CF_3]_2-(CH_2)_4-$, $-(CH_2)_3-[C(CH_3)CF_3]_2-(CH_2)_5-$, $-(CH_2)_3-[C(CH_3)CF_3]_2-(CH_2)_6-$, $-(CH_2)_3-[C(CH_3)CF_3]_2-(CH_2)_7-$, $-(CH_2)_4-[C(CH_3)CF_3]_2-(CH_2)_2-$, $-(CH_2)_4-[C(CH_3)CF_3]_2-(CH_2)_3-$, $-(CH_2)_4-[C(CH_3)CF_3]_2-(CH_2)_5-$, $-(CH_2)_4-[C(CH_3)CF_3]_2-(CH_2)_6-$, $-(CH_2)_5-[C(CH_3)CF_3]_2-(CH_2)_2-$, $-(CH_2)_5-[C(CH_3)CF_3]_2-(CH_2)_3-$, $-(CH_2)_5-[C(CH_3)CF_3]_2-(CH_2)_4-$, $-(CH_2)_6-[C(CH_3)CF_3]_2-(CH_2)_2-$, $-(CH_2)_6-[C(CH_3)CF_3]_2-(CH_2)_3-$, $-(CH_2)_6-[C(CH_3)CF_3]_2-(CH_2)_4-$, $-(CH_2)-[C(CH_3)CF_3]_3-$, $-(CH_2)-[C(CH_3)CF_3]_3-(CH_2)-$, $-(CH_2)-[C(CH_3)CF_3]_3-(CH_2)_2-$, $-(CH_2)-[C(CH_3)CF_3]_3-(CH_2)_3-$, $-(CH_2)-[C(CH_3)CF_3]_3-(CH_2)_4-$, $-(CH_2)-[C(CH_3)CF_3]_3-(CH_2)_5-$, $-(CH_2)-[C(CH_3)CF_3]_3-(CH_2)_6-$, $-(CH_2)-[C(CH_3)CF_3]_3-(CH_2)_7-$, $-(CH_2)-[C(CH_3)CF_3]_3-(CH_2)_8-$, $-(CH_2)_2-[C(CH_3)CF_3]_3-(CH_2)-$, $-(CH_2)_3-[C(CH_3)CF_3]_3-(CH_2)-$, $-(CH_2)_4-[C(CH_3)CF_3]_3-(CH_2)-$, $-(CH_2)_5-[C(CH_3)CF_3]_3-(CH_2)-$, $-(CH_2)_6-[C(CH_3)CF_3]_3-(CH_2)-$, $-(CH_2)_7-[C(CH_3)CF_3]_3-(CH_2)-$, $-(CH_2)_8-[C(CH_3)CF_3]_3-(CH_2)-$, $-(CH_2)_2-[C(CH_3)CF_3]_3-(CH_2)_2-$, $-(CH_2)_3-[C(CH_3)CF_3]_3-(CH_2)_3-$, $-(CH_2)_4-[C(CH_3)CF_3]_3-(CH_2)_4-$, $-(CH_2)_2-[C(CH_3)CF_3]_3-(CH_2)_3-$, $-(CH_2)_2-[C(CH_3)CF_3]_3-(CH_2)_4-$, $-(CH_2)_2-[C(CH_3)CF_3]_3-(CH_2)_5-$, $-(CH_2)_2-[C(CH_3)CF_3]_3-(CH_2)_6-$, $-(CH_2)_2-[C(CH_3)CF_3]_3-(CH_2)_7-$, $-(CH_2)_3-[C(CH_3)CF_3]_3-(CH_2)_2-$, $-(CH_2)_3-[C(CH_3)CF_3]_3-(CH_2)_4-$, $-(CH_2)_3-[C(CH_3)CF_3]_3-(CH_2)_5-$, $-(CH_2)_3-[C(CH_3)CF_3]_3-(CH_2)_6-$, $-(CH_2)_4-[C(CH_3)CF_3]_3-(CH_2)_2-$, $-(CH_2)_4-[C(CH_3)CF_3]_3-(CH_2)_3-$, $-(CH_2)_4-[C(CH_3)CF_3]_3-(CH_2)_5-$, $-(CH_2)_5-[C(CH_3)CF_3]_3-(CH_2)_2-$, $-(CH_2)_5-[C(CH_3)CF_3]_3-(CH_2)_3-$, $-(CH_2)_5-[C(CH_3)CF_3]_3-(CH_2)_4-$, $-(CH_2)_6-[C(CH_3)CF_3]_3-(CH_2)_2-$, $-(CH_2)_6-[C(CH_3)CF_3]_3-(CH_2)_3-$, $-(CH_2)-[C(CH_3)CF_3]_4-$, $-(CH_2)-[C(CH_3)CF_3]_4-(CH_2)-$, $-(CH_2)-[C(CH_3)CF_3]_4-(CH_2)_2-$, $-(CH_2)-[C(CH_3)CF_3]_4-(CH_2)_3-$, $-(CH_2)-[C(CH_3)CF_3]_4-(CH_2)_4-$, $-(CH_2)-[C(CH_3)CF_3]_4-(CH_2)_5-$, $-(CH_2)-[C(CH_3)CF_3]_4-(CH_2)_6-$, $-(CH_2)-[C(CH_3)CF_3]_4-(CH_2)_7-$, $-(CH_2)-[C(CH_3)CF_3]_4-(CH_2)_8-$, $-(CH_2)-[C(CH_3)CF_3]_4-(CH_2)_9-$, $-(CH_2)-[C(CH_3)CF_3]_4-(CH_2)_{10}-$, $-(CH_2)_2-[C(CH_3)CF_3]_4-(CH_2)-$, $-(CH_2)_3-[C(CH_3)CF_3]_4-(CH_2)-$, $-(CH_2)_4-[C(CH_3)CF_3]_4-(CH_2)-$, $-(CH_2)_5-[C(CH_3)CF_3]_4-(CH_2)-$, $-(CH_2)_6-[C(CH_3)CF_3]_4-(CH_2)-$, $-(CH_2)_7-[C(CH_3)CF_3]_4-(CH_2)-$, $-(CH_2)_2-[C(CH_3)CF_3]_4-(CH_2)_2-$, $-(CH_2)_3-[C(CH_3)CF_3]_4-(CH_2)_3-$, $-(CH_2)_4-[C$ (CH$_3$)CF$_3$]$_4$—(CH$_2$)$_4$—, —(CH$_2$)$_5$—[C(CH$_3$)CF$_3$]$_4$—(CH$_2$)$_5$—, —(CH$_2$)$_2$—[C(CH$_3$)CF$_3$]$_4$—(CH$_2$)$_3$—, —(CH$_2$)$_2$—[C(CH$_3$)CF$_3$]$_4$—(CH$_2$)$_4$—, —(CH$_2$)$_2$—[C(CH$_3$)CF$_3$]$_4$—(CH$_2$)$_5$—, —(CH$_2$)$_2$—[C(CH$_3$)CF$_3$]$_4$—(CH$_2$)$_6$—, —(CH$_2$)$_3$—[C(CH$_3$)CF$_3$]$_4$—(CH$_2$)$_2$—, —(CH$_2$)$_3$ —[C(CH$_3$)CF$_3$]$_4$—(CH$_2$)$_4$—, —(CH$_2$)$_4$—[C(CH$_3$)CF$_3$]$_4$—(CH$_2$)$_2$—, —(CH$_2$)$_4$—[C(CH$_3$)CF$_3$]$_4$—(CH$_2$)$_3$—, —(CH$_2$)$_5$—[C(CH$_3$)CF$_3$]$_4$—(CH$_2$)$_2$—, —(CH$_2$)$_5$ —[C(CH$_3$)CF$_3$]$_4$—(CH$_2$)$_3$—, —(CH$_2$)$_6$—[C(CH$_3$)CF$_3$]$_4$—(CH$_2$)$_2$—, —(CH$_2$)—[C(CH$_3$)CF$_3$]$_5$—, —(CH$_2$)—[C(CH$_3$)CF$_3$]$_5$—(CH$_2$)—, —(CH$_2$)—[C(CH$_3$)CF$_3$]$_5$—(CH$_2$)$_2$—, —(CH$_2$)—[C(CH$_3$)CF$_3$]$_5$—(CH$_2$)$_3$—, —(CH$_2$)—[C(CH$_3$)CF$_3$]$_5$—(CH$_2$)$_4$—, —(CH$_2$)—[C(CH$_3$)CF$_3$]$_5$—(CH$_2$)$_5$—, —(CH$_2$)—[C(CH$_3$)CF$_3$]$_5$—(CH$_2$)$_6$—, —(CH$_2$)$_2$—[C(CH$_3$)CF$_3$]$_5$—(CH$_2$)—, —(CH$_2$)$_3$—[C(CH$_3$)CF$_3$]$_5$—(CH$_2$)—, —(CH$_2$)$_4$—[C(CH$_3$)CF$_3$]$_5$—(CH$_2$)—, —(CH$_2$)$_5$—[C(CH$_3$)CF$_3$]$_5$—(CH$_2$)—, —(CH$_2$)$_6$—[C(CH$_3$)CF$_3$]$_5$—(CH$_2$)—, —(CH$_2$)$_2$—[C(CH$_3$)CF$_3$]$_5$—(CH$_2$)$_2$—, —(CH$_2$)$_3$—[C(CH$_3$)CF$_3$]$_5$—(CH$_2$)$_3$—, —(CH$_2$)$_4$—[C(CH$_3$)CF$_3$]$_5$—(CH$_2$)$_4$—, —(CH$_2$)$_2$—[C(CH$_3$)CF$_3$]$_5$—(CH$_2$)$_3$—, —(CH$_2$)$_2$ —[C(CH$_3$)CF$_3$]$_5$—(CH$_2$)$_4$—, —(CH$_2$)$_2$—[C(CH$_3$)CF$_3$]$_5$—(CH$_2$)$_5$—, —(CH$_2$)$_2$—[C(CH$_3$)CF$_3$]$_5$—(CH$_2$)$_6$—, —(CH$_2$)$_3$—[C(CH$_3$)CF$_3$]$_5$—(CH$_2$)$_2$—, —(CH$_2$)$_3$ —[C(CH$_3$)CF$_3$]$_5$—(CH$_2$)$_4$—, —(CH$_2$)$_4$—[C(CH$_3$)CF$_3$]$_5$—(CH$_2$)$_2$—, —(CH$_2$)$_4$—[C(CH$_3$)CF$_3$]$_5$—(CH$_2$)$_3$—, —(CH$_2$)$_5$—[C(CH$_3$)CF$_3$]$_5$—(CH$_2$)$_2$—, —(CH$_2$)—[CH(CH$_2$CF$_3$)]—, —(CH$_2$)—[CH(CH$_2$CF$_3$)]—(CH$_2$)—, —(CH$_2$)—[CH(CH$_2$CF$_3$)]—(CH$_2$)$_2$—, —(CH$_2$)—[CH(CH$_2$CF$_3$)]—(CH$_2$)$_3$—, —(CH$_2$)—[CH(CH$_2$CF$_3$)]—(CH$_2$)$_4$—, —(CH$_2$)—[CH(CH$_2$CF$_3$)]—(CH$_2$)$_5$ —, —(CH$_2$)—[CH(CH$_2$CF$_3$)]—(CH$_2$)$_6$—, —(CH$_2$)—[CH(CH$_2$CF$_3$)]—(CH$_2$)$_7$—, —(CH$_2$)—[CH(CH$_2$CF$_3$)]—(CH$_2$)$_8$—, —(CH$_2$)—[CH(CH$_2$CF$_3$)]—(CH$_2$)$_9$ —, —(CH$_2$)—[CH(CH$_2$CF$_3$)]—(CH$_2$)$_{10}$—, —(CH$_2$)$_2$—[CH(CH$_2$CF$_3$)]—(CH$_2$)—, —(CH$_2$)$_3$—[CH(CH$_2$CF$_3$)]—(CH$_2$)—, —(CH$_2$)$_4$—[CH(CH$_2$CF$_3$)]—(CH$_2$)—, —(CH$_2$)$_5$—[CH(CH$_2$CF$_3$)]—(CH$_2$)—, —(CH$_2$)$_6$—[CH(CH$_2$CF$_3$)]—(CH$_2$)—, —(CH$_2$)$_7$—[CH(CH$_2$CF$_3$)]—(CH$_2$)—, —(CH$_2$)$_8$—[CH(CH$_2$CF$_3$)]—(CH$_2$)—, —(CH$_2$)$_9$—[CH(CH$_2$CF$_3$)]—(CH$_2$)—, —(CH$_2$)$_{10}$—[CH(CH$_2$CF$_3$)]—(CH$_2$)—, —(CH$_2$)$_2$—[CH(CH$_2$CF$_3$)]—(CH$_2$)$_2$ —, —(CH$_2$)$_3$—[CH(CH$_2$CF$_3$)]—(CH$_2$)$_3$—, —(CH$_2$)$_4$—[CH(CH$_2$CF$_3$)]—(CH$_2$)$_4$—, —(CH$_2$)$_5$—[CH(CH$_2$CF$_3$)]—(CH$_2$)$_5$—, —(CH$_2$)$_2$—[CH(CH$_2$CF$_3$)]—(CH$_2$)$_3$—, —(CH$_2$)$_2$—[CH(CH$_2$CF$_3$)]—(CH$_2$)$_4$—, —(CH$_2$)$_2$ —[CH(CH$_2$CF$_3$)]—(CH$_2$)$_5$—, —(CH$_2$)$_2$—[CH(CH$_2$CF$_3$)]—(CH$_2$)$_6$—, —(CH$_2$)$_2$—[CH(CH$_2$CF$_3$)]—(CH$_2$)$_7$—, —(CH$_2$)$_2$—[CH(CH$_2$CF$_3$)]—(CH$_2$)$_8$—, —(CH$_2$)$_2$ —[CH(CH$_2$CF$_3$)]—(CH$_2$)$_9$—, —(CH$_2$)$_3$—[CH(CH$_2$CF$_3$)]—(CH$_2$)$_2$—, —(CH$_2$)$_3$—[CH(CH$_2$CF$_3$)]—(CH$_2$)$_4$—, —(CH$_2$)$_3$—[CH(CH$_2$CF$_3$)]—(CH$_2$)$_5$—, —(CH$_2$)$_3$ —[CH(CH$_2$CF$_3$)]—(CH$_2$)$_6$—, —(CH$_2$)$_3$—[CH(CH$_2$CF$_3$)]—(CH$_2$)$_7$—, —(CH$_2$)$_3$—[CH(CH$_2$CF$_3$)]—(CH$_2$)$_8$—, —(CH$_2$)$_4$—[CH(CH$_2$CF$_3$)]—(CH$_2$)$_2$—, —(CH$_2$)$_4$ —[CH(CH$_2$CF$_3$)]—(CH$_2$)$_3$—, —(CH$_2$)$_4$—[CH(CH$_2$CF$_3$)]—(CH$_2$)$_5$—, —(CH$_2$)$_4$—[CH(CH$_2$CF$_3$)]—(CH$_2$)$_6$—, —(CH$_2$)$_4$—[CH(CH$_2$CF$_3$)]—(CH$_2$)$_7$—, —(CH$_2$)$_5$ —[CH(CH$_2$CF$_3$)]—(CH$_2$)$_2$—, —(CH$_2$)$_5$—[CH(CH$_2$CF$_3$)]—(CH$_2$)$_3$—, —(CH$_2$)$_5$—[CH(CH$_2$CF$_3$)]—(CH$_2$)$_4$—, —(CH$_2$)$_5$—[CH(CH$_2$CF$_3$)]—(CH$_2$)$_6$—, —(CH$_2$)$_6$ —[CH(CH$_2$CF$_3$)]—(CH$_2$)$_2$—, —(CH$_2$)$_6$—[CH(CH$_2$CF$_3$)]—(CH$_2$)$_3$—, —(CH$_2$)$_6$—[CH(CH$_2$CF$_3$)]—(CH$_2$)$_4$—, —(CH$_2$)$_6$—[CH(CH$_2$CF$_3$)]—(CH$_2$)$_5$—, —(CH$_2$)—[CH(CH$_2$CF$_3$)]$_2$—, —(CH$_2$)—[CH(CH$_2$CF$_3$)]$_2$—(CH$_2$)—, —(CH$_2$)—[CH(CH$_2$CF$_3$)]$_2$—(CH$_2$)$_2$—, —(CH$_2$)—[CH(CH$_2$CF$_3$)]$_2$—(CH$_2$)$_3$—, —(CH$_2$)—[CH(CH$_2$CF$_3$)]$_2$—(CH$_2$)$_4$—, —(CH$_2$)—[CH(CH$_2$CF$_3$)]$_2$—(CH$_2$)$_5$—, —(CH$_2$)—[CH(CH$_2$CF$_3$)]$_2$—(CH$_2$)$_6$—, —(CH$_2$)—[CH(CH$_2$CF$_3$)]$_2$—(CH$_2$)$_7$—, —(CH$_2$)—[CH(CH$_2$CF$_3$)]$_2$—(CH$_2$)$_8$—, —(CH$_2$)—[CH(CH$_2$CF$_3$)]$_2$—(CH$_2$)$_9$—, —(CH$_2$)$_2$—[CH(CH$_2$CF$_3$)]$_2$—(CH$_2$)—, —(CH$_2$)$_3$ —[CH(CH$_2$CF$_3$)]$_2$—(CH$_2$)—, —(CH$_2$)$_4$—[CH(CH$_2$CF$_3$)]$_2$—(CH$_2$)—, —(CH$_2$)$_5$—[CH(CH$_2$CF$_3$)]$_2$—(CH$_2$)—, —(CH$_2$)$_6$—[CH(CH$_2$CF$_3$)]$_2$—(CH$_2$)—, —(CH$_2$)$_7$—[CH(CH$_2$CF$_3$)]$_2$—(CH$_2$)—, —(CH$_2$)$_8$—[CH(CH$_2$CF$_3$)]$_2$—(CH$_2$)—, —(CH$_2$)$_9$—[CH(CH$_2$CF$_3$)]$_2$—(CH$_2$)—, —(CH$_2$)$_2$—[CH(CH$_2$CF$_3$)]$_2$—(CH$_2$)$_2$—, —(CH$_2$)$_3$—[CH(CH$_2$CF$_3$)]$_2$—(CH$_2$)$_3$—, —(CH$_2$)$_4$—[CH(CH$_2$CF$_3$)]$_2$—(CH$_2$)$_4$—, —(CH$_2$)$_5$—[CH(CH$_2$CF$_3$)]$_2$—(CH$_2$)$_5$—, —(CH$_2$)$_2$—[CH(CH$_2$CF$_3$)]$_2$—(CH$_2$)$_3$—, —(CH$_2$)$_2$—[CH(CH$_2$CF$_3$)]$_2$—(CH$_2$)$_4$—, —(CH$_2$)$_2$—[CH(CH$_2$CF$_3$)]$_2$—(CH$_2$)$_5$—, —(CH$_2$)$_2$—[CH(CH$_2$CF$_3$)]$_2$—(CH$_2$)$_6$—, —(CH$_2$)$_2$—[CH(CH$_2$CF$_3$)]$_2$—(CH$_2$)$_7$—, —(CH$_2$)$_2$—[CH(CH$_2$CF$_3$)]$_2$—(CH$_2$)$_8$—, —(CH$_2$)$_3$—[CH(CH$_2$CF$_3$)]$_2$—(CH$_2$)$_2$—, —(CH$_2$)$_3$—[CH(CH$_2$CF$_3$)]$_2$—(CH$_2$)$_4$—, —(CH$_2$)$_3$—[CH(CH$_2$CF$_3$)]$_2$—(CH$_2$)$_5$—, —(CH$_2$)$_3$—[CH(CH$_2$CF$_3$)]$_2$—(CH$_2$)$_6$—, —(CH$_2$)$_3$—[CH(CH$_2$CF$_3$)]$_2$—(CH$_2$)$_7$—, —(CH$_2$)$_4$—[CH(CH$_2$CF$_3$)]$_2$—(CH$_2$)$_2$—, —(CH$_2$)$_4$—[CH(CH$_2$CF$_3$)]$_2$—(CH$_2$)$_3$—, —(CH$_2$)$_4$—[CH(CH$_2$CF$_3$)]$_2$—(CH$_2$)$_5$—, —(CH$_2$)$_4$—[CH(CH$_2$CF$_3$)]$_2$—(CH$_2$)$_6$—, —(CH$_2$)$_5$—[CH(CH$_2$CF$_3$)]$_2$—(CH$_2$)$_2$—, —(CH$_2$)$_5$—[CH(CH$_2$CF$_3$)]$_2$—(CH$_2$)$_3$—, —(CH$_2$)$_5$—[CH(CH$_2$CF$_3$)]$_2$—(CH$_2$)$_4$—, —(CH$_2$)$_6$—[CH(CH$_2$CF$_3$)]$_2$—(CH$_2$)$_2$—, —(CH$_2$)$_6$—[CH(CH$_2$CF$_3$)]$_2$—(CH$_2$)$_3$—, —(CH$_2$)$_6$—[CH(CH$_2$CF$_3$)]$_2$—(CH$_2$)$_4$—, —(CH$_2$)—[CH(CH$_2$CF$_3$)]$_3$—, —(CH$_2$)—[CH(CH$_2$CF$_3$)]$_3$—(CH$_2$)—, —(CH$_2$)—[CH(CH$_2$CF$_3$)]$_3$—(CH$_2$)$_2$—, —(CH$_2$)—[CH(CH$_2$CF$_3$)]$_3$—(CH$_2$)$_3$—, —(CH$_2$)—[CH(CH$_2$CF$_3$)]$_3$—(CH$_2$)$_4$—, —(CH$_2$)—[CH(CH$_2$CF$_3$)]$_3$—(CH$_2$)$_5$—, —(CH$_2$)—[CH(CH$_2$CF$_3$)]$_3$—(CH$_2$)$_6$—, —(CH$_2$)—[CH(CH$_2$CF$_3$)]$_3$—(CH$_2$)$_7$—, —(CH$_2$)—[CH(CH$_2$CF$_3$)]$_3$—(CH$_2$)$_8$—, —(CH$_2$)$_2$—[CH(CH$_2$CF$_3$)]$_3$—(CH$_2$)—, —(CH$_2$)$_3$—[CH(CH$_2$CF$_3$)]$_3$—(CH$_2$)—, —(CH$_2$)$_4$—[CH(CH$_2$CF$_3$)]$_3$—(CH$_2$)—, —(CH$_2$)$_5$—[CH(CH$_2$CF$_3$)]$_3$—(CH$_2$)—, —(CH$_2$)$_6$—[CH(CH$_2$CF$_3$)]$_3$—(CH$_2$)—, —(CH$_2$)$_7$—[CH(CH$_2$CF$_3$)]$_3$—(CH$_2$)—, —(CH$_2$)$_8$—[CH(CH$_2$CF$_3$)]$_3$—(CH$_2$)—, —(CH$_2$)$_2$—[CH(CH$_2$CF$_3$)]$_3$—(CH$_2$)$_2$—, —(CH$_2$)$_3$—[CH(CH$_2$CF$_3$)]$_3$—(CH$_2$)$_3$—, —(CH$_2$)$_4$—[CH(CH$_2$CF$_3$)]$_3$—(CH$_2$)$_4$—, —(CH$_2$)$_2$—[CH(CH$_2$CF$_3$)]$_3$—(CH$_2$)$_3$—, —(CH$_2$)$_2$—[CH(CH$_2$CF$_3$)]$_3$—(CH$_2$)$_4$—, —(CH$_2$)$_2$—[CH(CH$_2$CF$_3$)]$_3$—(CH$_2$)$_5$—, —(CH$_2$)$_2$—[CH(CH$_2$CF$_3$)]$_3$—(CH$_2$)$_6$—, —(CH$_2$)$_2$—[CH(CH$_2$CF$_3$)]$_3$—(CH$_2$)$_7$—, —(CH$_2$)$_3$—[CH(CH$_2$CF$_3$)]$_3$—(CH$_2$)$_2$—, —(CH$_2$)$_3$—[CH(CH$_2$CF$_3$)]$_3$—(CH$_2$)$_4$—, —(CH$_2$)$_3$—[CH(CH$_2$CF$_3$)]$_3$—(CH$_2$)$_5$—, —(CH$_2$)$_3$—[CH(CH$_2$CF$_3$)]$_3$—(CH$_2$)$_6$—, —(CH$_2$)$_4$—[CH(CH$_2$CF$_3$)]$_3$—(CH$_2$)$_2$—, —(CH$_2$)$_4$—[CH(CH$_2$CF$_3$)]$_3$—(CH$_2$)$_3$—, —(CH$_2$)$_4$—[CH(CH$_2$CF$_3$)]$_3$—(CH$_2$)$_5$—, —(CH$_2$)$_5$—[CH(CH$_2$CF$_3$)]$_3$—(CH$_2$)$_2$—, —(CH$_2$)$_5$—[CH(CH$_2$CF$_3$)]$_3$—(CH$_2$)$_3$—, —(CH$_2$)$_5$—[CH(CH$_2$CF$_3$)]$_3$—(CH$_2$)$_4$—, —(CH$_2$)$_6$—[CH(CH$_2$CF$_3$)]$_3$—(CH$_2$)$_2$—, —(CH$_2$)$_6$—[CH(CH$_2$CF$_3$)]$_3$—(CH$_2$)$_3$—, —(CH$_2$)—[CH(CH$_2$CF$_3$)]$_4$—, —(CH$_2$)—[CH(CH$_2$CF$_3$)]$_4$—(CH$_2$)—, —(CH$_2$)—[CH(CH$_2$CF$_3$)]$_4$—(CH$_2$)$_2$—, —(CH$_2$)—[CH(CH$_2$CF$_3$)]$_4$—(CH$_2$)$_3$—, —(CH$_2$)—[CH(CH$_2$CF$_3$)]$_4$—(CH$_2$)$_4$—, —(CH$_2$)—[CH(CH$_2$CF$_3$)]$_4$—(CH$_2$)$_5$—, —(CH$_2$)—[CH(CH$_2$CF$_3$)]$_4$—(CH$_2$)$_6$—, —(CH$_2$)—[CH(CH$_2$CF$_3$)]$_4$—(CH$_2$)$_7$—, —(CH$_2$)—[CH(CH$_2$CF$_3$)]$_4$—(CH$_2$)$_8$—, —(CH$_2$)—[CH(CH$_2$CF$_3$)]$_4$—(CH$_2$)$_3$—, —(CH$_2$)—[CH(CH$_2$CF$_3$)]$_4$—(CH$_2$)$_{13}$—, —(CH$_2$)$_2$—[CH(CH$_2$CF$_3$)]$_4$—(CH$_2$)—, —(CH$_2$)$_3$—[CH(CH$_2$CF$_3$)]$_4$—(CH$_2$)—, —(CH$_2$)$_4$—[CH(CH$_2$CF$_3$)]$_4$—(CH$_2$)—, —(CH$_2$)$_5$—[CH(CH$_2$CF$_3$)]$_4$—(CH$_2$)—, —(CH$_2$)$_6$—[CH(CH$_2$CF$_3$)]$_4$—(CH$_2$)—, $-(CH_2)_7-[CH(CH_2CF_3)]_4-(CH_2)-$, $-(CH_2)_2-[CH(CH_2CF_3)]_4-(CH_2)_2-$, $-(CH_2)_3-[CH(CH_2CF_3)]_4-(CH_2)_3-$, $-(CH_2)_4-[CH(CH_2CF_3)]_4-(CH_2)_4-$, $-(CH_2)_5-[CH(CH_2CF_3)]_4-(CH_2)_5-$, $-(CH_2)_2-[CH(CH_2CF_3)]_4-(CH_2)_3-$, $-(CH_2)_2-[CH(CH_2CF_3)]_4-(CH_2)_4-$, $-(CH_2)_2-[CH(CH_2CF_3)]_4-(CH_2)_5-$, $-(CH_2)_2-[CH(CH_2CF_3)]_4-(CH_2)_6-$, $-(CH_2)_3-[CH(CH_2CF_3)]_4-(CH_2)_2-$, $-(CH_2)_3-[CH(CH_2CF_3)]_4-(CH_2)_4-$, $-(CH_2)_4-[CH(CH_2CF_3)]_4-(CH_2)_2-$, $-(CH_2)_4-[CH(CH_2CF_3)]_4-(CH_2)_3-$, $-(CH_2)_5-[CH(CH_2CF_3)]_4-(CH_2)_2-$, $-(CH_2)_5-[CH(CH_2CF_3)]_4-(CH_2)_3-$, $-(CH_2)_6-[CH(CH_2CF_3)]_4-(CH_2)_2-$, $-(CH_2)-[CH(CH_2CF_3)]_5-$, $-(CH_2)-[CH(CH_2CF_3)]_5-(CH_2)-$, $-(CH_2)-[CH(CH_2CF_3)]_5-(CH_2)_2-$, $-(CH_2)-[CH(CH_2CF_3)]_5-(CH_2)_3-$, $-(CH_2)-[CH(CH_2CF_3)]_5-(CH_2)_4-$, $-(CH_2)-[CH(CH_2CF_3)]_5-(CH_2)_5-$, $-(CH_2)-[CH(CH_2CF_3)]_5-(CH_2)_6-$, $-(CH_2)_2-[CH(CH_2CF_3)]_5-(CH_2)-$, $-(CH_2)_3-[CH(CH_2CF_3)]_5-(CH_2)-$, $-(CH_2)_4-[CH(CH_2CF_3)]_5-(CH_2)-$, $-(CH_2)_5-[CH(CH_2CF_3)]_5-(CH_2)-$, $-(CH_2)_6-[CH(CH_2CF_3)]_5-(CH_2)-$, $-(CH_2)_2-[CH(CH_2CF_3)]_5-(CH_2)_2-$, $-(CH_2)_3-[CH(CH_2CF_3)]_5-(CH_2)_3-$, $-(CH_2)_4-[CH(CH_2CF_3)]_5-(CH_2)_4-$, $-(CH_2)_2-[CH(CH_2CF_3)]_5-(CH_2)_3-$, $-(CH_2)_2-[CH(CH_2CF_3)]_5-(CH_2)_4-$, $-(CH_2)_2-[CH(CH_2CF_3)]_5-(CH_2)_5-$, $-(CH_2)_2-[CH(CH_2CF_3)]_5-(CH_2)_6-$, $-(CH_2)_3-[CH(CH_2CF_3)]_5-(CH_2)_2-$, $-(CH_2)_3-[CH(CH_2CF_3)]_5-(CH_2)_4-$, $-(CH_2)_4-[CH(CH_2CF_3)]_5-(CH_2)_2-$, $-(CH_2)_4-[CH(CH_2CF_3)]_5-(CH_2)_3-$, $-(CH_2)_5-[CH(CH_2CF_3)]_5-(CH_2)_2-$, $-(CH_2)-[C(CH_3)(CH_2CF_3)]-$, $-(CH_2)-[C(CH_3)(CH_2CF_3)]-(CH_2)-$, $-(CH_2)-[C(CH_3)(CH_2CF_3)]-(CH_2)_2-$, $-(CH_2)-[C(CH_3)(CH_2CF_3)]-(CH_2)_3-$, $-(CH_2)-[C(CH_3)(CH_2CF_3)]-(CH_2)_4-$, $-(CH_2)-[C(CH_3)(CH_2CF_3)]-(CH_2)_5-$, $-(CH_2)-[C(CH_3)(CH_2CF_3)]-(CH_2)_6-$, $-(CH_2)-[C(CH_3)(CH_2CF_3)]-(CH_2)_7-$, $-(CH_2)-[C(CH_3)(CH_2CF_3)]-(CH_2)_8-$, $-(CH_2)-[C(CH_3)(CH_2CF_3)]-(CH_2)_9-$, $-(CH_2)-[C(CH_3)(CH_2CF_3)]-(CH_2)_{10}-$, $-(CH_2)_2-[C(CH_3)(CH_2CF_3)]-(CH_2)-$, $-(CH_2)_3-[C(CH_3)(CH_2CF_3)]-(CH_2)-$, $-(CH_2)_4-[C(CH_3)(CH_2CF_3)]-(CH_2)-$, $-(CH_2)_5-[C(CH_3)(CH_2CF_3)]-(CH_2)-$, $-(CH_2)_6-[C(CH_3)(CH_2CF_3)]-(CH_2)-$, $-(CH_2)_7-[C(CH_3)(CH_2CF_3)]-(CH_2)-$, $-(CH_2)_8-[C(CH_3)(CH_2CF_3)]-(CH_2)-$, $-(CH_2)_9-[C(CH_3)(CH_2CF_3)]-(CH_2)-$, $-(CH_2)_{10}-[C(CH_3)(CH_2CF_3)]-(CH_2)-$, $-(CH_2)_2-[C(CH_3)(CH_2CF_3)]-(CH_2)_2-$, $-(CH_2)_3-[C(CH_3)(CH_2CF_3)]-(CH_2)_3-$, $-(CH_2)_4-[C(CH_3)(CH_2CF_3)]-(CH_2)_4-$, $-(CH_2)_5-[C(CH_3)(CH_2CF_3)]-(CH_2)_5-$, $-(CH_2)_2-[C(CH_3)(CH_2CF_3)]-(CH_2)_3-$, $-(CH_2)_2-[C(CH_3)(CH_2CF_3)]-(CH_2)_4-$, $-(CH_2)_2-[C(CH_3)(CH_2CF_3)]-(CH_2)_5-$, $-(CH_2)_2-[C(CH_3)(CH_2CF_3)]-(CH_2)_6-$, $-(CH_2)_2-[C(CH_3)(CH_2CF_3)]-(CH_2)_7-$, $-(CH_2)_2-[C(CH_3)(CH_2CF_3)]-(CH_2)_8-$, $-(CH_2)_2-[C(CH_3)(CH_2CF_3)]-(CH_2)_9-$, $-(CH_2)_3-[C(CH_3)(CH_2CF_3)]-(CH_2)_2-$, $-(CH_2)_3-[C(CH_3)(CH_2CF_3)]-(CH_2)_4-$, $-(CH_2)_3-[C(CH_3)(CH_2CF_3)]-(CH_2)_5-$, $-(CH_2)_3-[C(CH_3)(CH_2CF_3)]-(CH_2)_6-$, $-(CH_2)_3-[C(CH_3)(CH_2CF_3)]-(CH_2)_7-$, $-(CH_2)_3-[C(CH_3)(CH_2CF_3)]-(CH_2)_8-$, $-(CH_2)_4-[C(CH_3)(CH_2CF_3)]-(CH_2)_2-$, $-(CH_2)_4-[C(CH_3)(CH_2CF_3)]-(CH_2)_3-$, $-(CH_2)_4-[C(CH_3)(CH_2CF_3)]-(CH_2)_5-$, $-(CH_2)_4-[C(CH_3)(CH_2CF_3)]-(CH_2)_6-$, $-(CH_2)_4-[C(CH_3)(CH_2CF_3)]-(CH_2)_7-$, $-(CH_2)_5-[C(CH_3)(CH_2CF_3)]-(CH_2)_2-$, $-(CH_2)_5-[C(CH_3)(CH_2CF_3)]-(CH_2)_3-$, $-(CH_2)_5-[C(CH_3)(CH_2CF_3)]-(CH_2)_4-$, $-(CH_2)_5-[C(CH_3)(CH_2CF_3)]-(CH_2)_6-$, $-(CH_2)_6-[C(CH_3)(CH_2CF_3)]-(CH_2)_2-$, $-(CH_2)_6-[C(CH_3)(CH_2CF_3)]-(CH_2)_3-$, $-(CH_2)_6-[C(CH_3)(CH_2CF_3)]-(CH_2)_4-$, $-(CH_2)_6-[C(CH_3)(CH_2CF_3)]-(CH_2)_5-$, $-(CH_2)-[C(CH_3)(CH_2CF_3)]_2-$, $-(CH_2)-[C(CH_3)(CH_2CF_3)]_2-(CH_2)-$, $-(CH_2)-[C(CH_3)(CH_2CF_3)]_2-(CH_2)_2-$, $-(CH_2)-[C(CH_3)(CH_2CF_3)]_2-(CH_2)_3-$, $-(CH_2)-[C(CH_3)(CH_2CF_3)]_2-(CH_2)_4-$, $-(CH_2)-[C(CH_3)(CH_2CF_3)]_2-(CH_2)_5-$, $-(CH_2)-[C(CH_3)(CH_2CF_3)]_2-(CH_2)_6-$, $-(CH_2)-[C(CH_3)(CH_2CF_3)]_2-(CH_2)_7-$, $-(CH_2)-[C(CH_3)(CH_2CF_3)]_2-(CH_2)_8-$, $-(CH_2)-[C(CH_3)(CH_2CF_3)]_2-(CH_2)_9-$, $-(CH_2)_2-[C(CH_3)(CH_2CF_3)]_2-(CH_2)-$, $-(CH_2)_3-[C(CH_3)(CH_2CF_3)]_2-(CH_2)-$, $-(CH_2)_4-[C(CH_3)(CH_2CF_3)]_2-(CH_2)-$, $-(CH_2)_5-[C(CH_3)(CH_2CF_3)]_2-(CH_2)-$, $-(CH_2)_6-[C(CH_3)(CH_2CF_3)]_2-(CH_2)-$, $-(CH_2)_7-[C(CH_3)(CH_2CF_3)]_2-(CH_2)-$, $-(CH_2)_8-[C(CH_3)(CH_2CF_3)]_2-(CH_2)-$, $-(CH_2)_9-[C(CH_3)(CH_2CF_3)]_2-(CH_2)-$, $-(CH_2)_2-[C(CH_3)(CH_2CF_3)]_2-(CH_2)_2-$, $-(CH_2)_3-[C(CH_3)(CH_2CF_3)]_2-(CH_2)_3-$, $-(CH_2)_4-[C(CH_3)(CH_2CF_3)]_2-(CH_2)_4-$, $-(CH_2)_5-[C(CH_3)(CH_2CF_3)]_2-(CH_2)_5-$, $-(CH_2)_2-[C(CH_3)(CH_2CF_3)]_2-(CH_2)_3-$, $-(CH_2)_2-[C(CH_3)(CH_2CF_3)]_2-(CH_2)_4-$, $-(CH_2)_2-[C(CH_3)(CH_2CF_3)]_2-(CH_2)_5-$, $-(CH_2)_2-[C(CH_3)(CH_2CF_3)]_2-(CH_2)_6-$, $-(CH_2)_2-[C(CH_3)(CH_2CF_3)]_2-(CH_2)_7-$, $-(CH_2)_2-[C(CH_3)(CH_2CF_3)]_2-(CH_2)_8-$, $-(CH_2)_3-[C(CH_3)(CH_2CF_3)]_2-(CH_2)_2-$, $-(CH_2)_3-[C(CH_3)(CH_2CF_3)]_2-(CH_2)_4-$, $-(CH_2)_3-[C(CH_3)(CH_2CF_3)]_2-(CH_2)_5-$, $-(CH_2)_3-[C(CH_3)(CH_2CF_3)]_2-(CH_2)_6-$, $-(CH_2)_3-[C(CH_3)(CH_2CF_3)]_2-(CH_2)_7-$, $-(CH_2)_4-[C(CH_3)(CH_2CF_3)]_2-(CH_2)_2-$, $-(CH_2)_4-[C(CH_3)(CH_2CF_3)]_2-(CH_2)_3-$, $-(CH_2)_4-[C(CH_3)(CH_2CF_3)]_2-(CH_2)_5-$, $-(CH_2)_4-[C(CH_3)(CH_2CF_3)]_2-(CH_2)_6-$, $-(CH_2)_5-[C(CH_3)(CH_2CF_3)]_2-(CH_2)_2-$, $-(CH_2)_6-[C(CH_3)(CH_2CF_3)]_2-(CH_2)_3-$, $-(CH_2)_5-[C(CH_3)(CH_2CF_3)]_2-(CH_2)_4-$, $-(CH_2)_6-[C(CH_3)(CH_2CF_3)]_2-(CH_2)_2-$, $-(CH_2)_6-[C(CH_3)(CH_2CF_3)]_2-(CH_2)_3-$, $-(CH_2)_6-[C(CH_3)(CH_2CF_3)]_2-(CH_2)_4-$, $-(CH_2)-[C(CH_3)(CH_2CF_3)]_3-$, $-(CH_2)-[C(CH_3)(CH_2CF_3)]_3-(CH_2)-$, $-(CH_2)-[C(CH_3)(CH_2CF_3)]_3-(CH_2)_2-$, $-(CH_2)-[C(CH_3)(CH_2CF_3)]_3-(CH_2)_3-$, $-(CH_2)-[C(CH_3)(CH_2CF_3)]_3-(CH_2)_4-$, $-(CH_2)-[C(CH_3)(CH_2CF_3)]_3-(CH_2)_5-$, $-(CH_2)-[C(CH_3)(CH_2CF_3)]_3-(CH_2)_6-$, $-(CH_2)-[C(CH_3)(CH_2CF_3)]_3-(CH_2)_7-$, $-(CH_2)-[C(CH_3)(CH_2CF_3)]_3-(CH_2)_8-$, $-(CH_2)_2-[C(CH_3)(CH_2CF_3)]_3-(CH_2)-$, $-(CH_2)_3-[C(CH_3)(CH_2CF_3)]_3-(CH_2)-$, $-(CH_2)_4-[C(CH_3)(CH_2CF_3)]_3-(CH_2)-$, $-(CH_2)_5-[C(CH_3)(CH_2CF_3)]_3-(CH_2)-$, $-(CH_2)_6-[C(CH_3)(CH_2CF_3)]_3-(CH_2)-$, $-(CH_2)_7-[C(CH_3)(CH_2CF_3)]_3-(CH_2)-$, $-(CH_2)_8-[C(CH_3)(CH_2CF_3)]_3-(CH_2)-$, $-(CH_2)_2-[C(CH_3)(CH_2CF_3)]_3-(CH_2)_2-$, $-(CH_2)_3-[C(CH_3)(CH_2CF_3)]_3-(CH_2)_3-$, $-(CH_2)_4-[C(CH_3)(CH_2CF_3)]_3-(CH_2)_4-$, $-(CH_2)_2-[C(CH_3)(CH_2CF_3)]_3-(CH_2)_3-$, $-(CH_2)_2-[C(CH_3)(CH_2CF_3)]_3-(CH_2)_4-$, $-(CH_2)_2-[C(CH_3)(CH_2CF_3)]_3-(CH_2)_5-$, $-(CH_2)_2-[C(CH_3)(CH_2CF_3)]_3-(CH_2)_6-$, $-(CH_2)_2-[C(CH_3)(CH_2CF_3)]_3-(CH_2)_7-$, $-(CH_2)_3-[C(CH_3)(CH_2CF_3)]_3-(CH_2)_2-$, $-(CH_2)_3-[C(CH_3)(CH_2CF_3)]_3-(CH_2)_4-$, $-(CH_2)_3-[C(CH_3)(CH_2CF_3)]_3-(CH_2)_5-$, $-(CH_2)_3-[C(CH_3)(CH_2CF_3)]_3-(CH_2)_6-$, $-(CH_2)_4-[C(CH_3)(CH_2CF_3)]_3-(CH_2)_2-$, $-(CH_2)_4-[C(CH_3)(CH_2CF_3)]_3-(CH_2)_3-$, $-(CH_2)_4-[C(CH_3)(CH_2CF_3)]_3-(CH_2)_5-$, $-(CH_2)_5-[C(CH_3)(CH_2CF_3)]_3-(CH_2)_2-$, $-(CH_2)_6-[C(CH_3)(CH_2CF_3)]_3-(CH_2)_3-$, $-(CH_2)_5-[C(CH_3)(CH_2CF_3)]_3-(CH_2)_4-$, $-(CH_2)_6-[C(CH_3)(CH_2CF_3)]_3-(CH_2)_2-$, $-(CH_2)_6-[C(CH_3)(CH_2CF_3)]_3-(CH_2)_3-$, $-(CH_2)-[C(CH_3)(CH_2CF_3)]_4-$, $-(CH_2)-[C(CH_3)(CH_2CF_3)]_4-(CH_2)-$, $-(CH_2)-[C(CH_3)(CH_2CF_3)]_4-(CH_2)_2-$, $-(CH_2)-[C(CH_3)(CH_2CF_3)]_4-(CH_2)_3-$, $-(CH_2)-[C(CH_3)(CH_2CF_3)]_4-(CH_2)_4-$, $-(CH_2)-[C(CH_3)(CH_2CF_3)]_4-(CH_2)_5-$, $-(CH_2)-[C(CH_3)(CH_2CF_3)]_4-(CH_2)_6-$, $-(CH_2)-[C(CH_3)(CH_2CF_3)]_4-(CH_2)_7-$, $-(CH_2)-[C(CH_3)(CH_2CF_3)]_4-(CH_2)_8-$, $-(CH_2)-[C(CH_3)(CH_2CF_3)]_4-(CH_2)_9-$, $-(CH_2)-[C(CH_3)(CH_2CF_3)]_4-(CH_2)_{10}-$, $-(CH_2)_2-[C(CH_3)(CH_2CF_3)]_4-(CH_2)-$, $-(CH_3)-[C(CH_3)(CH_2CF_3)]_4-(CH_2)-$, $-(CH_2)_4-[C(CH_3)(CH_2CF_3)]_4-(CH_2)-$, $-(CH_2)_6-[C(CH_3)(CH_2CF_3)]_4-(CH_2)-$, $-(CH_2)_6-[C(CH_3)(CH_2CF_3)]_4-(CH_2)-$, $-(CH_2)_7-[C(CH_3)(CH_2CF_3)]_4-(CH_2)-$, $-(CH_2)_2-[C(CH_3)(CH_2CF_3)]_4-(CH_2)_2-$, $-(CH_2)_3-[C(CH_3)(CH_2CF_3)]_4-(CH_2)_3-$, $-(CH_2)_4-[C(CH_3)(CH_2CF_3)]_4-(CH_2)_4-$, $-(CH_2)_6-[C(CH_3)(CH_2CF_3)]_4-(CH_2)_6-$, $-(CH_2)_2-[C(CH_3)(CH_2CF_3)]_4-(CH_2)_3-$, $-(CH_2)_2-[C(CH_3)(CH_2CF_3)]_4-(CH_2)_4-$, $-(CH_2)_2-[C(CH_3)(CH_2CF_3)]_4-(CH_2)_5-$, $-(CH_2)_2-[C(CH_3)(CH_2CF_3)]_4-(CH_2)_6-$, $-(CH_2)_3-[C(CH_3)(CH_2CF_3)]_4-(CH_2)_2-$, $-(CH_2)_3-[C(CH_3)(CH_2CF_3)]_4-(CH_2)_4-$, $-(CH_2)_4-[C(CH_3)(CH_2CF_3)]_4-(CH_2)_2-$, $-(CH_2)_4-[C(CH_3)(CH_2CF_3)]_4-(CH_2)_3-$, $-(CH_2)_5-[C(CH_3)(CH_2CF_3)]_4-(CH_2)_2-$, $-(CH_2)_5-[C(CH_3)(CH_2CF_3)]_4-(CH_2)_3-$, $-(CH_2)_6-[C(CH_3)(CH_2CF_3)]_4-(CH_2)_2-$, $-(CH_2)-[C(CH_3)(CH_2CF_3)]_5-$, $-(CH_2)-[C(CH_3)(CH_2CF_3)]_5-(CH_2)-$, $-(CH_2)-[C(CH_3)(CH_2CF_3)]_5-(CH_2)_2-$, $-(CH_2)-[C(CH_3)(CH_2CF_3)]_5-(CH_2)_3-$, $-(CH_2)-[C(CH_3)(CH_2CF_3)]_5-(CH_2)_4-$, $-(CH_2)-[C(CH_3)(CH_2CF_3)]_5-(CH_2)_5-$, $-(CH_2)-[C(CH_3)(CH_2CF_3)]_5-(CH_2)_6-$, $-(CH_2)_2-[C(CH_3)(CH_2CF_3)]_5-(CH_2)-$, $-(CH_2)_3-[C(CH_3)(CH_2CF_3)]_5-(CH_2)-$, $-(CH_2)_4-[C(CH_3)(CH_2CF_3)]_5-(CH_2)-$, $-(CH_2)_5-[C(CH_3)(CH_2CF_3)]_5-(CH_2)-$, $-(CH_2)_6-[C(CH_3)(CH_2CF_3)]_5-(CH_2)-$, $-(CH_2)_2-[C(CH_3)(CH_2CF_3)]_5-(CH_2)_2-$, $-(CH_2)_3-[C(CH_3)(CH_2CF_3)]_5-(CH_2)_3-$, $-(CH_2)_4-[C(CH_3)(CH_2CF_3)]_5-(CH_2)_4-$, $-(CH_2)_2-[C(CH_3)(CH_2CF_3)]_5-(CH_2)_3-$, $-(CH_2)_2-[C(CH_3)(CH_2CF_3)]_5-(CH_2)_4-$, $-(CH_2)_2-[C(CH_3)(CH_2CF_3)]_5-(CH_2)_5-$, $-(CH_2)_2-[C(CH_3)(CH_2CF_3)]_5-(CH_2)_6-$, $-(CH_2)_3-[C(CH_3)(CH_2CF_3)]_5-(CH_2)_2-$, $-(CH_2)_3-[C(CH_3)(CH_2CF_3)]_5-(CH_2)_4-$, $-(CH_2)_4-[C(CH_3)(CH_2CF_3)]_5-(CH_2)_2-$, $-(CH_2)_4-[C(CH_3)(CH_2CF_3)]_5-(CH_2)_3-$, $-(CH_2)_5-[C(CH_3)(CH_2CF_3)]_5-(CH_2)_2-$,
$-(CH_2)-(CF_2)-O-(CF_2)-O-(CF_2)-(CH_2)-$,
$-(CH_2)_2-(CF_2)-O-(CF_2)-O-(CF_2)-(CH_2)_2-$,
$-(CH_2)_3-(CF_2)-O-(CF_2)-O-(CF_2)-(CH_2)_3-$,
$-(CH_2)_4-(CF_2)-O-(CF_2)-O-(CF_2)-(CH_2)_4-$,
$-(CH_2)-(CF_2)-O-(CF_2)-O-(CF_2)-(CH_2)_2-$,
$-(CH_2)-(CF_2)-O-(CF_2)-O-(CF_2)-(CH_2)_3-$,
$-(CH_2)-(CF_2)-O-(CF_2)-O-(CF_2)-(CH_2)_4-$,
$-(CH_2)-(CF_2)-O-(CF_2)-O-(CF_2)-(CH_2)_5-$,
$-(CH_2)-(CF_2)-O-(CF_2)-O-(CF_2)-(CH_2)_6-$,
$-(CH_2)-(CF_2)-O-(CF_2)-O-(CF_2)-(CH_2)_7-$,
$-(CH_2)_2-(CF_2)-O-(CF_2)-O-(CF_2)-(CH_2)-$,
$-(CH_2)_3-(CF_2)-O-(CF_2)-O-(CF_2)-(CH_2)-$,
$-(CH_2)_4-(CF_2)-O-(CF_2)-O-(CF_2)-(CH_2)-$,
$-(CH_2)_5-(CF_2)-O-(CF_2)-O-(CF_2)-(CH_2)-$,
$-(CH_2)_6-(CF_2)-O-(CF_2)-O-(CF_2)-(CH_2)-$,
$-(CH_2)_7-(CF_2)-O-(CF_2)-O-(CF_2)-(CH_2)-$,
$-(CH_2)_2-(CF_2)-O-(CF_2)-O-(CF_2)-(CH_2)_3-$,
$-(CH_2)_2-(CF_2)-O-(CF_2)-O-(CF_2)-(CH_2)_4-$,
$-(CH_2)_2-(CF_2)-O-(CF_2)-O-(CF_2)-(CH_2)_5-$,
$-(CH_2)_2-(CF_2)-O-(CF_2)-O-(CF_2)-(CH_2)_6-$,
$-(CH_2)_3-(CF_2)-O-(CF_2)-O-(CF_2)-(CH_2)_2-$,
$-(CH_2)_4-(CF_2)-O-(CF_2)-O-(CF_2)-(CH_2)_2-$,
$-(CH_2)_5-(CF_2)-O-(CF_2)-O-(CF_2)-(CH_2)_2-$,
$-(CH_2)_6-(CF_2)-O-(CF_2)-O-(CF_2)-(CH_2)_2-$,
$-(CH_2)_3-(CF_2)-O-(CF_2)-O-(CF_2)-(CH_2)_4-$,
$-(CH_2)_4-(CF_2)-O-(CF_2)-O-(CF_2)-(CH_2)_3-$,
$-(CH_2)_3-(CF_2)-O-(CF_2)-O-(CF_2)-(CH_2)_5-$,
$-(CH_2)_5-(CF_2)-O-(CF_2)-O-(CF_2)-(CH_2)_3-$,
$-(CH_2)-(CF_2)-O-(CF_2)-O-(CF_2)-(CH_2)-$,
$-(CH_2)_2-(CF_2)-O-(CF_2)_2-O-(CF_2)-(CH_2)_2-$,
$-(CH_2)_3-(CF_2)-O-(CF_2)_2-O-(CF_2)-(CH_2)_3-$,
$-(CH_2)_4-(CF_2)-O-(CF_2)_2-O-(CF_2)-(CH_2)_4-$,
$-(CH_2)-(CF_2)-O-(CF_2)_2-O-(CF_2)-(CH_2)_2-$,
$-(CH_2)-(CF_2)-O-(CF_2)_2-O-(CF_2)-(CH_2)_3-$,
$-(CH_2)-(CF_2)-O-(CF_2)_2-O-(CF_2)-(CH_2)_4-$,
$-(CH_2)-(CF_2)-O-(CF_2)_2-O-(CF_2)-(CH_2)_5-$,
$-(CH_2)-(CF_2)-O-(CF_2)_2-O-(CF_2)-(CH_2)_6-$,
$-(CH_2)-(CF_2)-O-(CF_2)_2-O-(CF_2)-(CH_2)_7-$,
$-(CH_2)_2-(CF_2)-O-(CF_2)_2-O-(CF_2)-(CH_2)-$,
$-(CH_2)_3-(CF_2)-O-(CF_2)_2-O-(CF_2)-(CH_2)-$,
$-(CH_2)_4-(CF_2)-O-(CF_2)_2-O-(CF_2)-(CH_2)-$,
$-(CH_2)_5-(CF_2)-O-(CF_2)_2-O-(CF_2)-(CH_2)-$,
$-(CH_2)_6-(CF_2)-O-(CF_2)_2-O-(CF_2)-(CH_2)-$,
$-(CH_2)_7-(CF_2)-O-(CF_2)_2-O-(CF_2)-(CH_2)-$,
$-(CH_2)_2-(CF_2)-O-(CF_2)_2-O-(CF_2)-(CH_2)_3-$,
$-(CH_2)_2-(CF_2)-O-(CF_2)_2-O-(CF_2)-(CH_2)_4-$,
$-(CH_2)_2-(CF_2)-O-(CF_2)_2-O-(CF_2)-(CH_2)_5-$,
$-(CH_2)_2-(CF_2)-O-(CF_2)_2-O-(CF_2)-(CH_2)_6-$,
$-(CH_2)_3-(CF_2)-O-(CF_2)_2-O-(CF_2)-(CH_2)_2-$,
$-(CH_2)_4-(CF_2)-O-(CF_2)_2-O-(CF_2)-(CH_2)_2-$,
$-(CH_2)_5-(CF_2)-O-(CF_2)_2-O-(CF_2)-(CH_2)_2-$,
$-(CH_2)_6-(CF_2)-O-(CF_2)_2-O-(CF_2)-(CH_2)_2-$,
$-(CH_2)_3-(CF_2)-O-(CF_2)_2-O-(CF_2)-(CH_2)_4-$,
$-(CH_2)_4-(CF_2)-O-(CF_2)_2-O-(CF_2)-(CH_2)_3-$,
$-(CH_2)_3-(CF_2)-O-(CF_2)_2-O-(CF_2)-(CH_2)_5-$,
$-(CH_2)_5-(CF_2)-O-(CF_2)_2-O-(CF_2)-(CH_2)_3-$,
$-(CH_2)-(CF_2)_2-O-(CF_2)_2-O-(CF_2)_2-(CH_2)-$,
$-(CH_2)_2-(CF_2)_2-O-(CF_2)_2-O-(CF_2)_2-(CH_2)_2-$,
$-(CH_2)_3-(CF_2)_2-O-(CF_2)_2-O-(CF_2)_2-(CH_2)_3-$,
$-(CH_2)_4-(CF_2)_2-O-(CF_2)_2-O-(CF_2)_2-(CH_2)_4-$,
$-(CH_2)-(CF_2)_2-O-(CF_2)_2-O-(CF_2)_2-(CH_2)_2-$,
$-(CH_2)-(CF_2)_2-O-(CF_2)_2-O-(CF_2)_2-(CH_2)_3-$,
$-(CH_2)-(CF_2)_2-O-(CF_2)_2-O-(CF_2)_2-(CH_2)_3-$,
$-(CH_2)-(CF_2)_2-O-(CF_2)_2-O-(CF_2)_2-(CH_2)_4-$,
$-(CH_2)-(CF_2)_2-O-(CF_2)_2-O-(CF_2)_2-(CH_2)_5-$,
$-(CH_2)-(CF_2)_2-O-(CF_2)_2-O-(CF_2)_2-(CH_2)_6-$,
$-(CH_2)-(CF_2)_2-O-(CF_2)_2-O-(CF_2)_2-(CH_2)_7-$,
$-(CH_2)_2-(CF_2)_2-O-(CF_2)_2-O-(CF_2)_2-(CH_2)-$,
$-(CH_2)_3-(CF_2)_2-O-(CF_2)_2-O-(CF_2)_2-(CH_2)-$,
$-(CH_2)_4-(CF_2)_2-O-(CF_2)_2-O-(CF_2)_2-(CH_2)-$,
$-(CH_2)_5-(CF_2)_2-O-(CF_2)_2-O-(CF_2)_2-(CH_2)-$,
$-(CH_2)_6-(CF_2)_2-O-(CF_2)_2-O-(CF_2)_2-(CH_2)-$,
$-(CH_2)_7-(CF_2)_2-O-(CF_2)_2-O-(CF_2)_2-(CH_2)-$,
$-(CH_2)_2-(CF_2)_2-O-(CF_2)_2-O-(CF_2)_2-(CH_2)_3-$,
$-(CH_2)_2-(CF_2)_2-O-(CF_2)_2-O-(CF_2)_2-(CH_2)_4-$,
$-(CH_2)_2-(CF_2)_2-O-(CF_2)_2-O-(CF_2)_2-(CH_2)_5-$,
$-(CH_2)_2-(CF_2)_2-O-(CF_2)_2-O-(CF_2)_2-(CH_2)_6-$,
$-(CH_2)_3-(CF_2)_2-O-(CF_2)_2-O-(CF_2)_2-(CH_2)_2-$,
$-(CH_2)_4-(CF_2)_2-O-(CF_2)_2-O-(CF_2)_2-(CH_2)_2-$,
$-(CH_2)_5-(CF_2)_2-O-(CF_2)_2-O-(CF_2)_2-(CH_2)_2-$,
$-(CH_2)_6-(CF_2)_2-O-(CF_2)_2-O-(CF_2)_2-(CH_2)_2-$,
$-(CH_2)_3-(CF_2)_2-O-(CF_2)_2-O-(CF_2)_2-(CH_2)_4-$,
$-(CH_2)_4-(CF_2)_2-O-(CF_2)_2-O-(CF_2)_2-(CH_2)_3-$,
$-(CH_2)_3-(CF_2)_2-O-(CF_2)_2-O-(CF_2)_2-(CH_2)_5-$,
$-(CH_2)_5-(CF_2)_2-O-(CF_2)_2-O-(CF_2)_2-(CH_2)_3-$,
$-(CH_2)-(CF_2)-O-(CF_2)-O-(CF_2)-O-(CF_2)-(CH_2)-$, $-(CH_2)_2-(CF_2)-O-(CF_2)-O-(CF_2)-O-(CF_2)-(CH_2)_2-$, $-(CH_2)_3-(CF_2)-O-(CF_2)-O-(CF_2)-O-(CF_2)-(CH_2)_3-$, $-(CH_2)_4-(CF_2)-O-(CF_2)-O-(CF_2)-O-(CF_2)-(CH_2)_4-$, $-(CH_2)-(CF_2)-O-(CF_2)-O-(CF_2)-O-(CF_2)-(CH_2)_2-$, $—(CH_2)—(CF_2)—O—(CF_2)—O—(CF_2)—O—(CF_2)—(CH_2)_3—$, $—(CH_2)—(CF_2)—O—(CF_2)—O—(CF_2)—O—(CF_2)—(CH_2)_4—$, $—(CH_2)—(CF_2)—O—(CF_2)—O—(CF_2)—O—(CF_2)—(CH_2)_5—$, $—(CH_2)—(CF_2)—O—(CF_2)—O—(CF_2)—O—(CF_2)—(CH_2)_6—$, $—(CH_2)—(CF_2)—O—(CF_2)—O—(CF_2)—O—(CF_2)—(CH_2)_7—$, $—(CH_2)_2—(CF_2)—O—(CF_2)—O—(CF_2)—O—(CF_2)—(CH_2)—$, $—(CH_2)_3—(CF_2)—O—(CF_2)—O—(CF_2)—O—(CF_2)—(CH_2)—$, $—(CH_2)_4—(CF_2)—O—(CF_2)—O—(CF_2)—O—(CF_2)—(CH_2)—$, $—(CH_2)_5—(CF_2)—O—(CF_2)—O—(CF_2)—O—(CF_2)—(CH_2)—$, $—(CH_2)_6—(CF_2)—O—(CF_2)—O—(CF_2)—O—(CF_2)—(CH_2)—$, $—(CH_2)_7—(CF_2)—O—(CF_2)—O—(CF_2)—O—(CF_2)—(CH_2)—$, $—(CH_2)_2—(CF_2)—O—(CF_2)—O—(CF_2)—O—(CF_2)—(CH_2)_3—$, $—(CH_2)_2—(CF_2)—O—(CF_2)—O—(CF_2)—O—(CF_2)—(CH_2)_4—$, $—(CH_2)_2—(CF_2)—O—(CF_2)—O—(CF_2)—O—(CF_2)—(CH_2)_5—$, $—(CH_2)_2—(CF_2)—O—(CF_2)—O—(CF_2)—O—(CF_2)—(CH_2)_6—$, $—(CH_2)_3—(CF_2)—O—(CF_2)—O—(CF_2)—O—(CF_2)—(CH_2)_2—$, $—(CH_2)_4—(CF_2)—O—(CF_2)—O—(CF_2)—O—(CF_2)—(CH_2)_2—$, $—(CH_2)_5—(CF_2)—O—(CF_2)—O—(CF_2)—O—(CF_2)—(CH_2)_2—$, $—(CH_2)_6—(CF_2)—O—(CF_2)—O—(CF_2)—O—(CF_2)—(CH_2)_2—$, $—(CH_2)_3—(CF_2)—O—(CF_2)—O—(CF_2)—O—(CF_2)—(CH_2)_4—$, $—(CH_2)_4—(CF_2)—O—(CF_2)—O—(CF_2)—O—(CF_2)—(CH_2)_3—$, $—(CH_2)_3—(CF_2)—O—(CF_2)—O—(CF_2)—O—(CF_2)—(CH_2)_5—$, $—(CH_2)_5—(CF_2)—O—(CF_2)—O—(CF_2)—O—(CF_2)—(CH_2)_3—$, $—(CH_2)—(CF_2)_2—O—(CF_2)_2—O—(CF_2)_2—O—(CF_2)_2—(CH_2)—$, $—(CH_2)_2—(CF_2)_2—O—(CF_2)_2—O—(CF_2)_2—O—(CF_2)_2—(CH_2)_2—$, $—(CH_2)_3—(CF_2)_2—O—(CF_2)_2—O—(CF_2)_2—O—(CF_2)_2—(CH_2)_3—$, $—(CH_2)_4—(CF_2)_2—O—(CF_2)_2—O—(CF_2)_2—O—(CF_2)_2—(CH_2)_4—$, $—(CH_2)—(CF_2)_2—O—(CF_2)_2—O—(CF_2)_2—O—(CF_2)_2—(CH_2)_2—$, $—(CH_2)—(CF_2)_2—O—(CF_2)_2—O—(CF_2)_2—O—(CF_2)_2—(CH_2)_3—$, $—(CH_2)—(CF_2)_2—O—(CF_2)_2—O—(CF_2)_2—O—(CF_2)_2—(CH_2)_4—$, $—(CH_2)—(CF_2)_2—O—(CF_2)_2—O—(CF_2)_2—O—(CF_2)_2—(CH_2)_5—$, $—(CH_2)—(CF_2)_2—O—(CF_2)_2—O—(CF_2)_2—O—(CF_2)_2—(CH_2)_6—$, $—(CH_2)—(CF_2)_2—O—(CF_2)_2—O—(CF_2)_2—O—(CF_2)_2—(CH_2)_7—$, $—(CH_2)_2—(CF_2)_2—O—(CF_2)_2—O—(CF_2)_2—O—(CF_2)_2—(CH_2)—$, $—(CH_2)_3—(CF_2)_2—O—(CF_2)_2—O—(CF_2)_2—O—(CF_2)_2—(CH_2)—$, $—(CH_2)_4—(CF_2)_2—O—(CF_2)_2—O—(CF_2)_2—O—(CF_2)_2—(CH_2)—$, $—(CH_2)_5—(CF_2)_2—O—(CF_2)_2—O—(CF_2)_2—O—(CF_2)_2—(CH_2)—$, $—(CH_2)_6—(CF_2)_2—O—(CF_2)_2—O—(CF_2)_2—O—(CF_2)_2—(CH_2)—$, $—(CH_2)_7—(CF_2)_2—O—(CF_2)_2—O—(CF_2)_2—O—(CF_2)_2—(CH_2)—$, $—(CH_2)_2—(CF_2)_2—O—(CF_2)_2—O—(CF_2)_2—O—(CF_2)_2—(CH_2)_3—$, $—(CH_2)_2—(CF_2)_2—O—(CF_2)_2—O—(CF_2)_2—O—(CF_2)_2—(CH_2)_4—$, $—(CH_2)_2—(CF_2)_2—O—(CF_2)_2—O—(CF_2)_2—O—(CF_2)_2—(CH_2)_5—$, $—(CH_2)_2—(CF_2)_2—O—(CF_2)_2—O—(CF_2)_2—O—(CF_2)_2—(CH_2)_6—$, $—(CH_2)_3—(CF_2)_2—O—(CF_2)_2—O—(CF_2)_2—O—(CF_2)_2—(CH_2)_2—$, $—(CH_2)_4—(CF_2)_2—O—(CF_2)_2—O—(CF_2)_2—O—(CF_2)_2—(CH_2)_2—$, $—(CH_2)_6—(CF_2)_2—O—(CF_2)_2—O—(CF_2)_2—O—(CF_2)_2—(CH_2)_2—$, $—(CH_2)_6—(CF_2)_2—O—(CF_2)_2—O—(CF_2)_2—O—(CF_2)_2—(CH_2)_2—$, $—(CH_2)_3—(CF_2)_2—O—(CF_2)_2—O—(CF_2)_2—O—(CF_2)_2—(CH_2)_4—$, $—(CH_2)_4—(CF_2)_2—O—(CF_2)_2—O—(CF_2)_2—O—(CF_2)_2—(CH_2)_3—$, $—(CH_2)_3—(CF_2)_2—O—(CF_2)_2—O—(CF_2)_2—O—(CF_2)_2—(CH_2)_6—$, $—(CH_2)_6—(CF_2)_2—O—(CF_2)_2—O—(CF_2)_2—O—(CF_2)_2—(CH_2)_3—$,

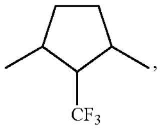, 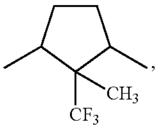, 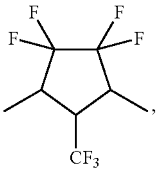, 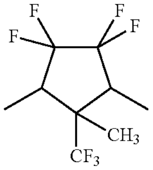, 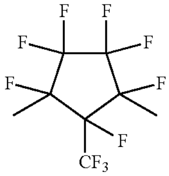 or 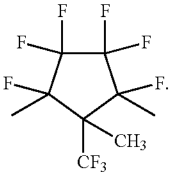

Preferred examples for $—R_2—$ are $—(CH_2)_6—$, $—(CH_2)_8—$, $—(CH_2)_{12}—$, $—(CH_2)_3—(CF_2)—(CH_2)_3—$, $—(CH_2)_2—(CFH)_2—(CH_2)_2—$, $—(CH_2)—(CF_2)_3—(CH_2)—$, $—(CH_2)_2—(CF_2)_4—(CH_2)_2—$, $—(CH_2)—[CH(CF_3)]—(CH_2)—$, $—(CH_2)—[C(CH_3)CF_3]—(CH_2)—$, $—(CH_2)—[CH(CH_2CF_3)]—(CH_2)—$, $—(CH_2)—[C(CH_3)(CH_2CF_3)]—(CH_2)—$, $—(CH_2)_2—(CF_2)—O—(CF_2)—O—(CF_2)—(CH_2)_2—$, $—(CH_2)—(CF_2)—O—(CF_2)—O—(CF_2)—O—(CF_2)—(CH_2)—$,

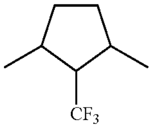 and 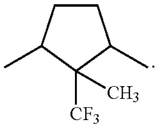.

Particularly preferred examples for $—R_2—$ are $—(CH_2)_6—$, $—(CH_2)_8—$, $—(CH_2)_{12}—$, $—(CH_2)_3—(CF_2)—(CH_2)_3—$, $—(CH_2)_2—(CFH)_2—(CH_2)_2—$ and $—(CH_2)_2—(CF_2)_4—(CH_2)_2—$.

Compounds of formula (I), (I-1), (I-2), (I'), (I'') and (I''') with linkers —[B]— and substituents as described before or preferably described before having a polymerizable group as described before or preferably described before or below are preferred in case the substituent $—R_2—$ within the at least one linking element $Y—R_2—$ corresponds to $—(C(R)_2)_o—$, wherein R is at each occurrence independently H or F and o has a meaning as described before.

The invention therefore relates to compounds of formula (I), (I-1), (I-2), (I'), (I'') and (I''') as described before or preferably described before wherein $—R_2—$ is at each occurrence independently $—(C(R)_2)_o—$, wherein R is at each occurrence independently H or F and o has a meaning as described before.

The substituent $Y—R_2—R_1$ is particularly preferably selected from the group consisting of $O—R_2—R_1$, $—R_2—R_1$ and $S—R_2—R_1$ wherein $—R_2—$ has a meaning as described before or preferably or particularly preferably described before and wherein $R_1$ is a polymerizable group or has a preferred meaning as described below.

The substituent $Y—R_2—R_1$ is preferably $O—R_2—R_1$ and $—R_2—$ is selected from the group consisting of $—(CH_2)_6—$, $—(CH_2)_8—$, $—(CH_2)_{12}—$, $—(CH_2)_3—(CF_2)—(CH_2)_3—$, $—(CH_2)_2—(CFH)_2—(CH_2)_2—$, $—(CH_2)—(CF_2)_3—(CH_2)—$, $—(CH_2)_2—(CF_2)_4—(CH_2)_2—$, $—(CH_2)—[CH(CF_3)]—(CH_2)—$, $—(CH_2)—[C(CH_3)CF_3]—(CH_2)—$, $—(CH_2)—[CH(CH_2CF_3)]—(CH_2)—$, $—(CH_2)—[C(CH_3)(CH_2CF_3)]—(CH_2)—$, $—(CH_2)_2—(CF_2)—O—(CF_2)—O—(CF_2)—(CH_2)_2—$, $—(CH_2)—(CF_2)—O—(CF_2)—O—(CF_2)—O—(CF_2)—(CH_2)—$,

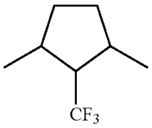 and 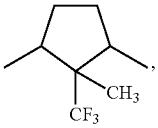, and wherein $R_1$ is a polymerizable group which contains a Si atom or has a preferred meaning as described below.

The substituent Y—$R_2$—$R_1$ is preferably O—$R_2$—$R_1$ and —$R_2$— is selected from the group consisting of —$(CH_2)_6$—, —$(CH_2)_8$—, —$(CH_2)_{12}$—, —$(CH_2)_3$—$(CF_2)$—$(CH_2)_3$—, —$(CH_2)_2$—$(CFH)_2$—$(CH_2)_2$— and —$(CH_2)_2$—$(CF_2)_4$—$(CH_2)_2$—, and wherein $R_1$ is a polymerizable group which contains at least one Si atom.

Preferably, $R_1$ is selected from the group consisting of a trialkoxysilyl group, a dialkoxyalkylsilyl group and silyl groups of formula (5), (6) and (7), (5)

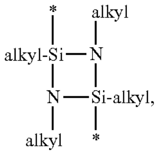

(6)

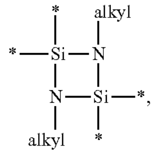

(7)

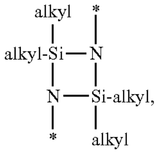

where alkyl means at each occurrence independently of each other a linear or branched alkyl group having 1 to 6 C atoms, alkoxy means at each occurrence independently of each other a linear or branched alkoxy group having 1 to 6 C atoms and the asterisk "*" denotes at each occurrence independently of each other a linkage to the linker [—$R_2$—Y]$_n$ and/or [Y—$R_2$—]$_m$ as described before or preferably described before.

Particularly preferably, $R_1$ is selected from the group consisting of trialkoxysilyl or dialkoxyalkylsilyl, where alkyl means at each occurrence independently of each other a linear or branched alkyl group having 1 to 6 C atoms and alkoxy means at each occurrence independently of each other a linear or branched alkoxy group having 1 to 6 C atoms.

The preferred groups $R_1$ are preferably combined with preferred groups of the linking element —$R_2$— and/or the linking element Y—$R_2$—. Combinations are excluded where two O atoms, two N atoms, one O atom and one S atom or one O atom and one N atom are directly bonded to each other as known for a skilled artisan in the field of organic chemistry.

The substituent Y—$R_2$—$R_1$ is therefore particularly preferably selected from the group consisting of O—$R_2$—$R_1$ and —$R_2$— is selected from the group consisting of —$(CH_2)_6$—, —$(CH_2)_8$—, —$(CH_2)_{12}$—, —$(CH_2)_3$—$(CF_2)$—$(CH_2)_3$—, —$(CH_2)_2$—$(CFH)_2$—$(CH_2)_2$—, —$(CH_2)$—$(CF_2)_3$—$(CH_2)$—, —$(CH_2)_2$—$(CF_2)_4$—$(CH_2)_2$—, —$(CH_2)$—$[CH(CF_3)]$—$(CH_2)$—, —$(CH_2)$—$[C(CH_3)CF_3]$—$(CH_2)$—, —$(CH_2)$—$[CH(CH_2CF_3)]$—$(CH_2)$—, —$(CH_2)$—$[C(CH_3)(CH_2CF_3)]$—$(CH_2)$—, —$(CH_2)_2$—$(CF_2)$—O—$(CF_2)$—O—$(CF_2)$—$(CH_2)_2$—, —$(CH_2)$—$(CF_2)$—O—$(CF_2)$—O—$(CF_2)$—O—$(CF_2)$—$(CH_2)$—,

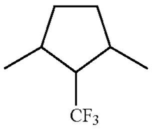 and 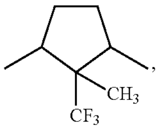, wherein $R_1$ is trialkoxysilyl or dialkoxyalkylsilyl, where alkyl means a linear or branched alkyl group having 1 to 6 C atoms and alkoxy means at each occurrence independently of each other a linear or branched alkoxy group having 1 to 6 C atoms.

The substituent Y—$R_2$—$R_1$ is therefore very particularly preferably selected from the group consisting of O—$R_2$—$R_1$ and —$R_2$— is selected from the group consisting of —$(CH_2)_6$—, —$(CH_2)_8$—, —$(CH_2)_{12}$—, —$(CH_2)_3$—$(CF_2)$—$(CH_2)_3$—, —$(CH_2)_2$—$(CFH)_2$—$(CH_2)_2$— and —$(CH_2)_2$—$(CF_2)_4$—$(CH_2)_2$—, wherein $R_1$ is trialkoxysilyl or dialkoxyalkylsilyl, where alkyl means a linear or branched alkyl group having 1 to 6 C atoms and alkoxy means at each occurrence independently of each other a linear or branched alkoxy group having 1 to 6 C atoms.

Very particularly preferably, $R_1$ is triethoxysilyl or diethoxymethylsilyl.

The invention therefore relates further to compounds of formula (I), (I-1), (I-2), (I'), (I'') and/or (I''') as described before or preferably described before wherein $R_1$ is at each occurrence independently a triethoxysilyl group or a diethoxymethylsilyl group.

Examples for compounds of formula (I), (I-1), (I-2), (I'), (I'') and/or (I''') are the following compounds Si-001 to Si-094:

Si-001

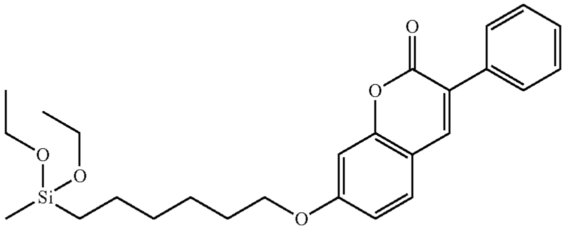

Si-002

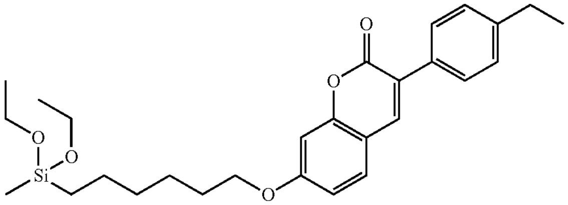

-continued
Si-003
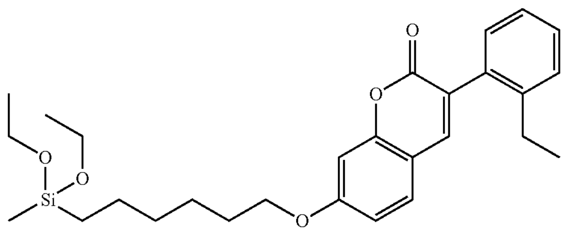
Si-004
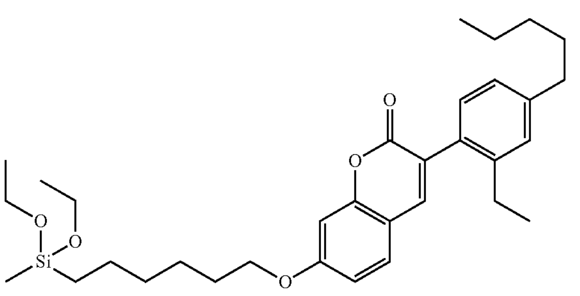
Si-005
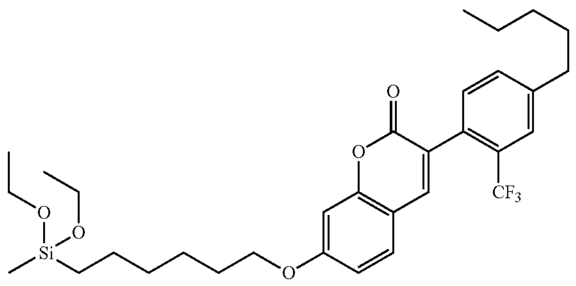
Si-006
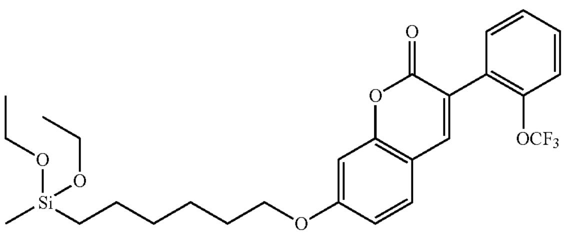
Si-007
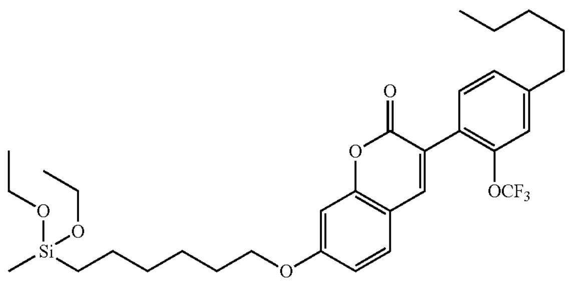
Si-008
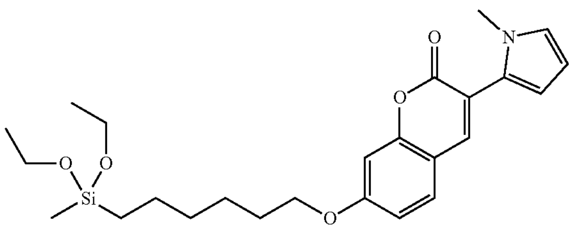
Si-009
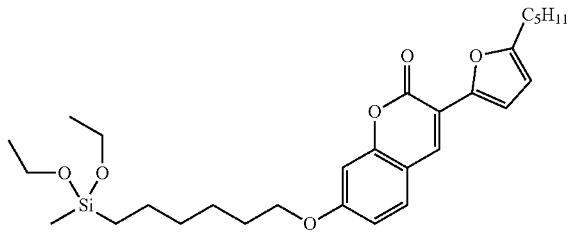
Si-010
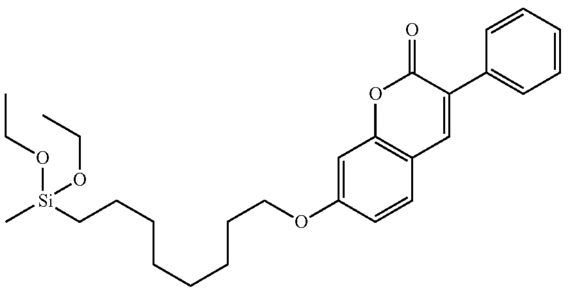
Si-011
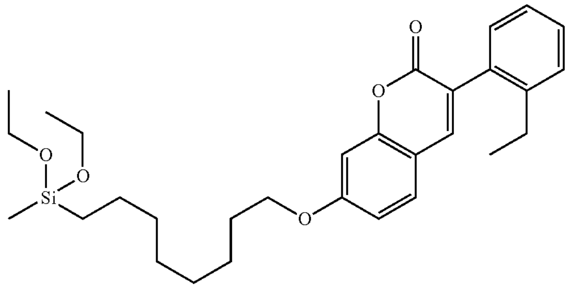
Si-012
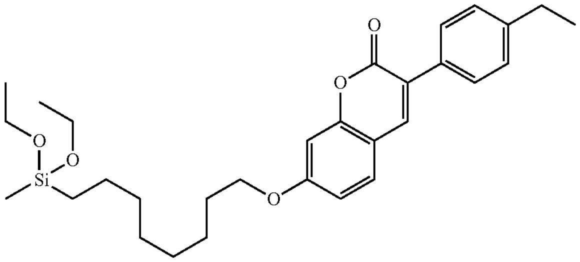

-continued
Si-013
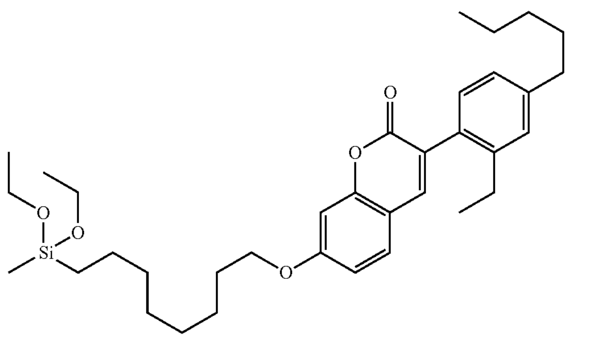
Si-014
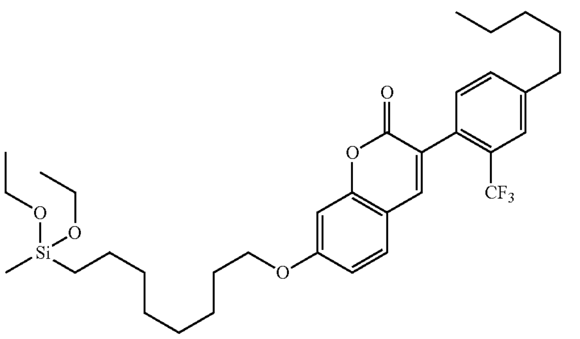
Si-015
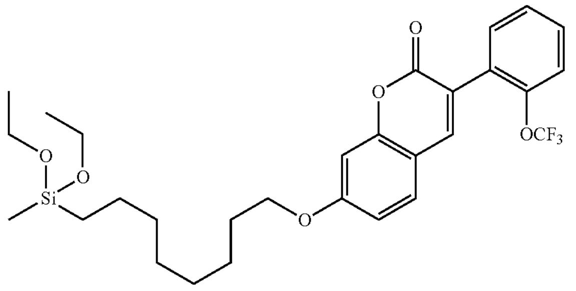
Si-016
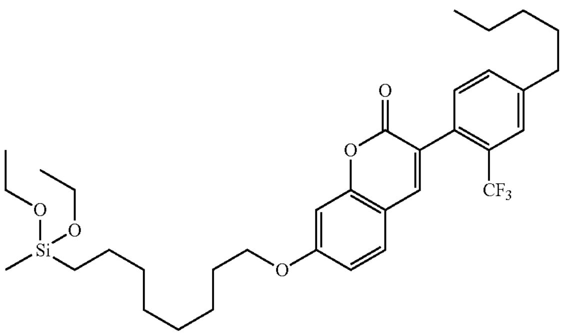
Si-017
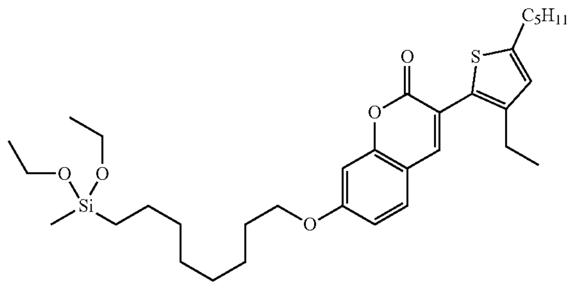
Si-018
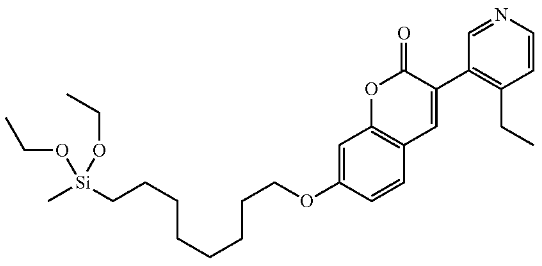
Si-019
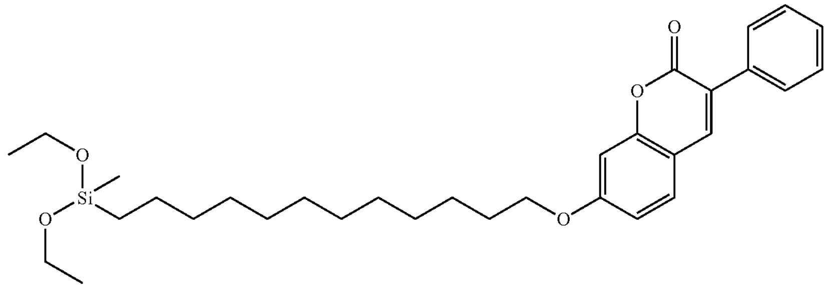
Si-020
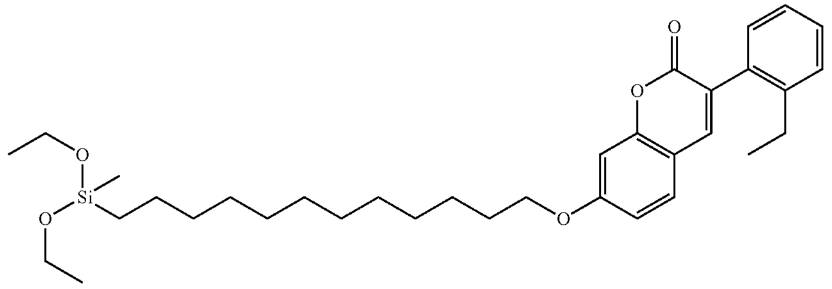

-continued
Si-021
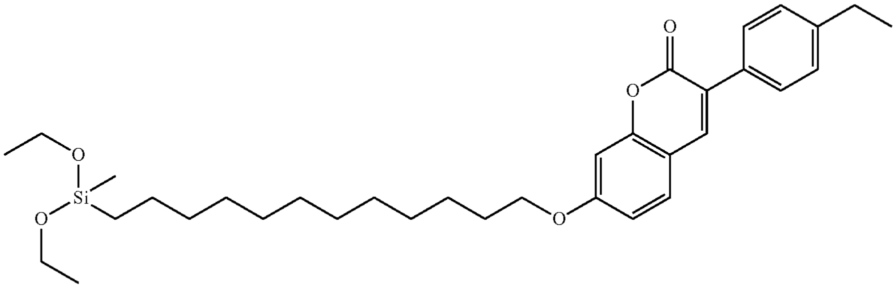
Si-022
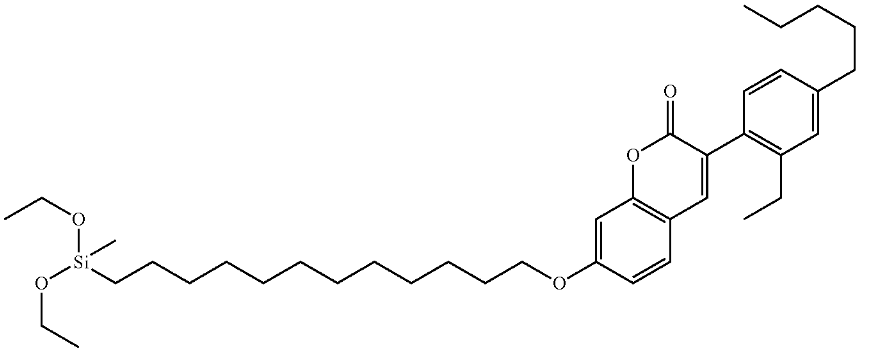
Si-023
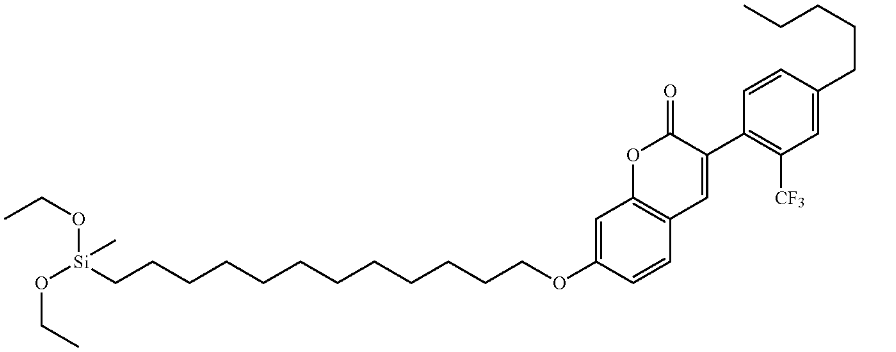
Si-024
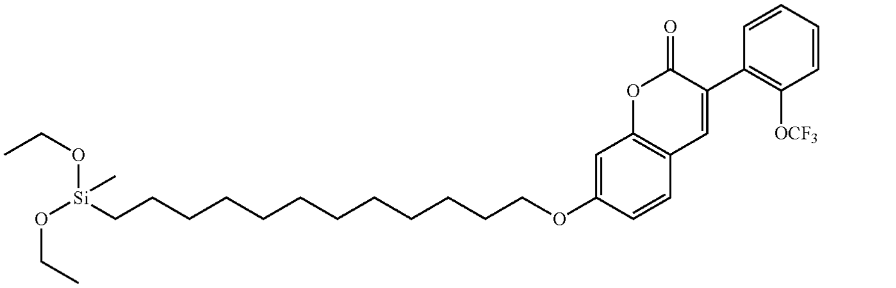

-continued
Si-025
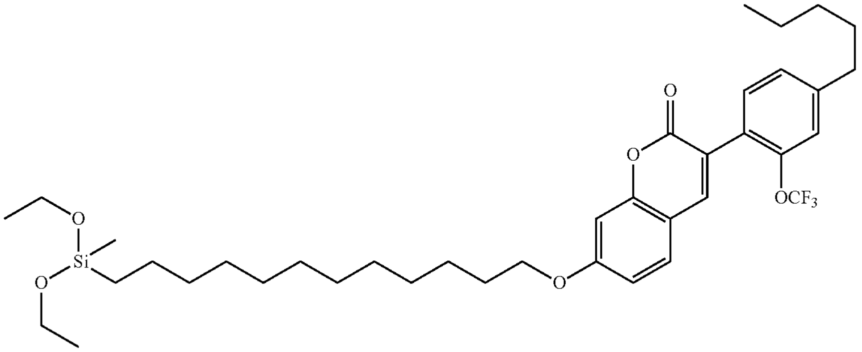
Si-026
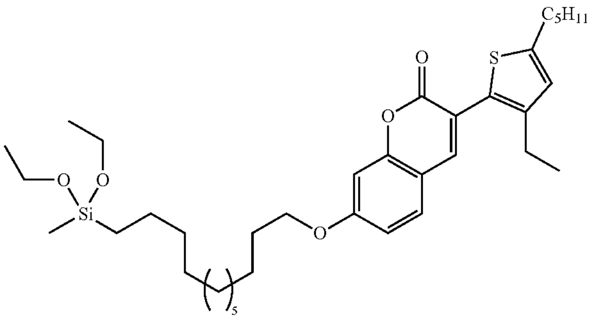
Si-027
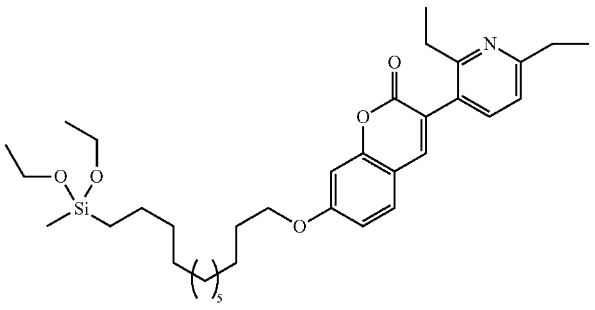
Si-028
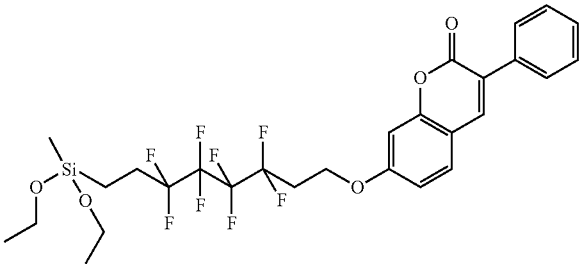
Si-029
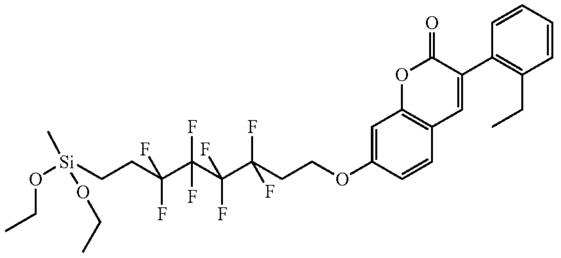
Si-030
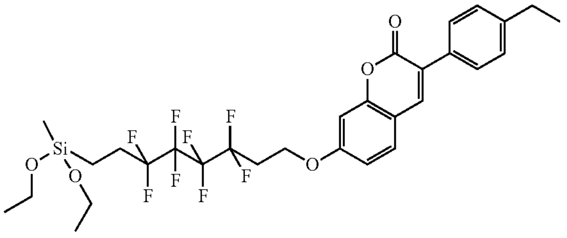
Si-031
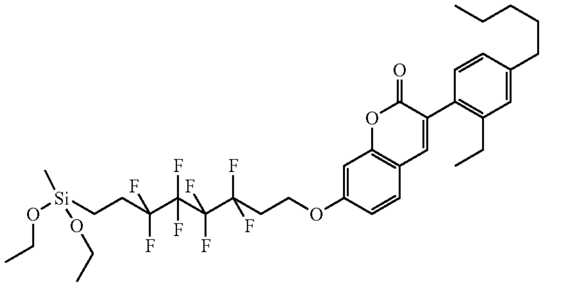
Si-032
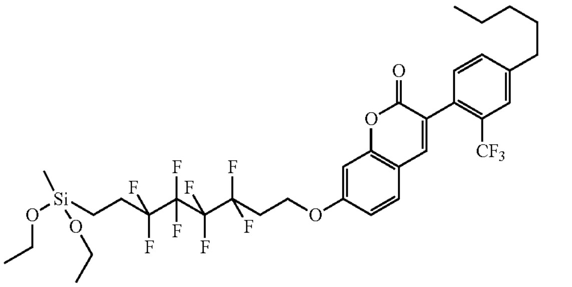
Si-033
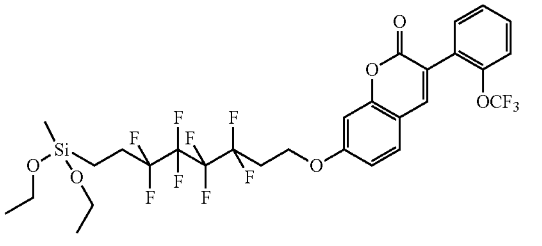

-continued
Si-034
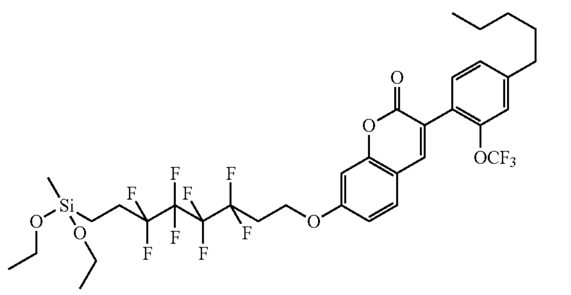
Si-035
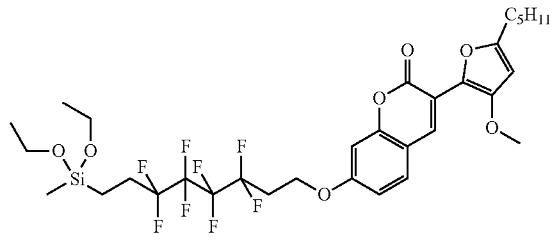
Si-036
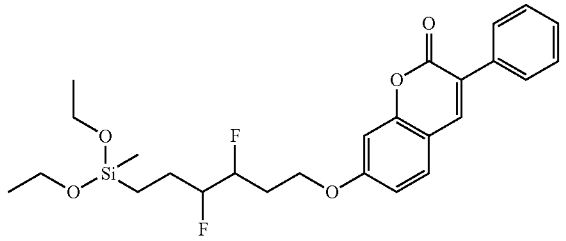
Si-037
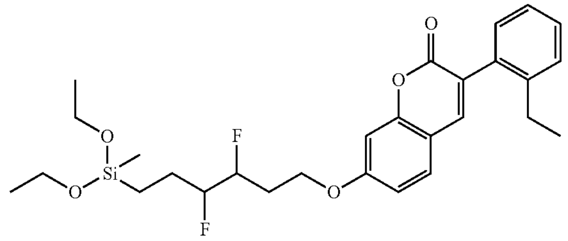
Si-038
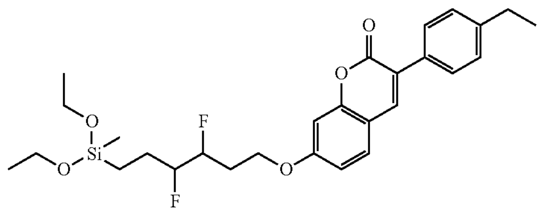
Si-039
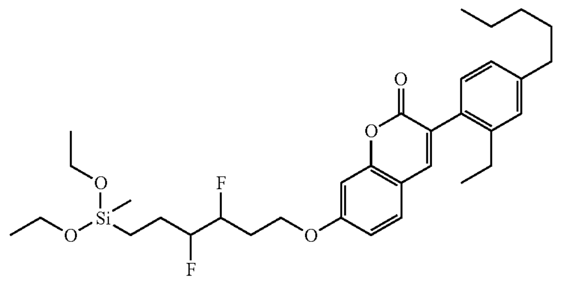
Si-040
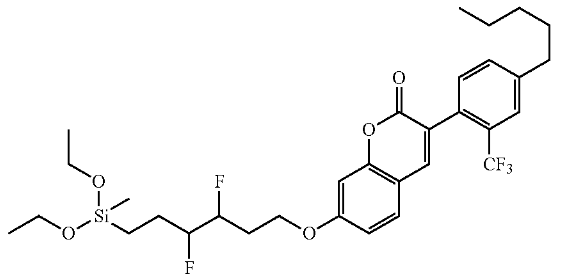
Si-041
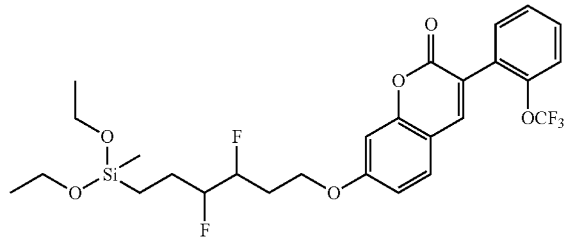
Si-042
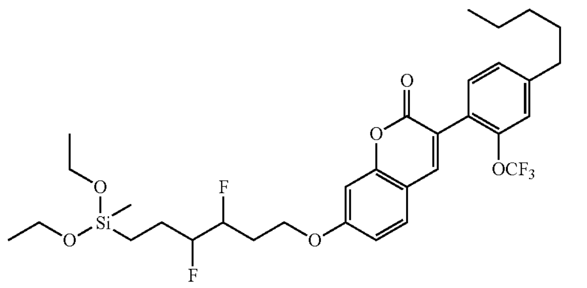
Si-043
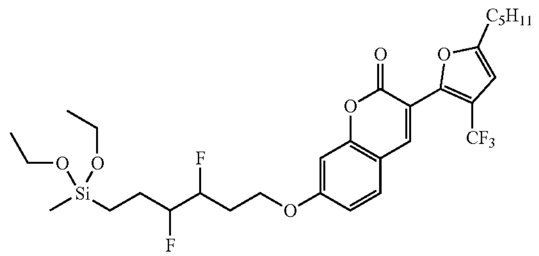

-continued
Si-044
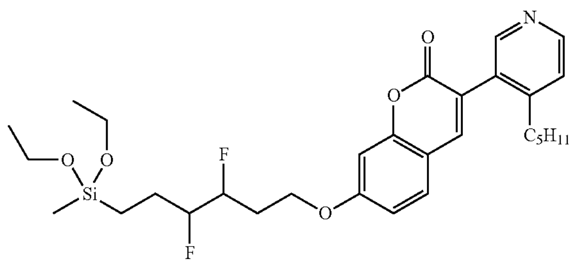
Si-045
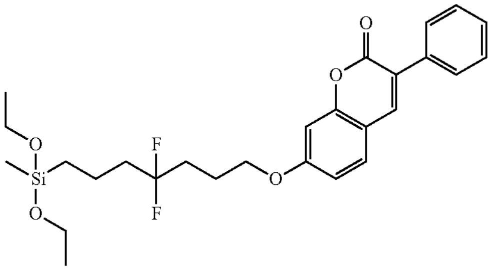
Si-046
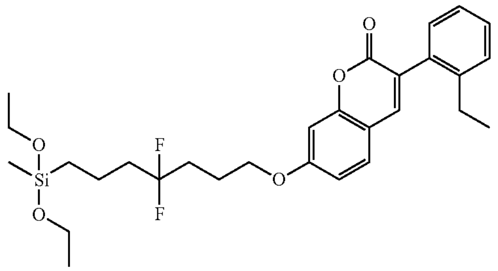
Si-047
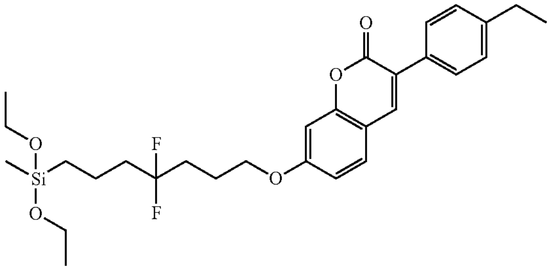
Si-048
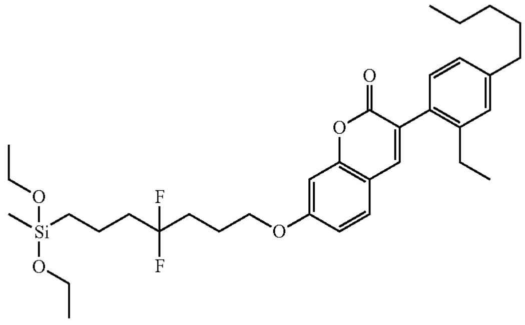
Si-049
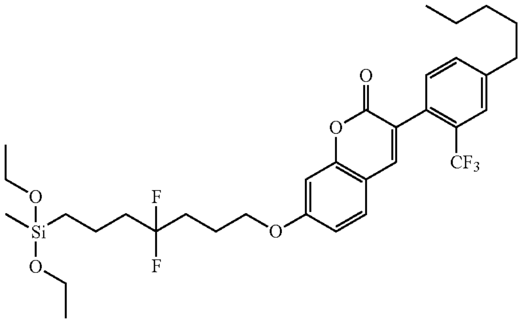
Si-050
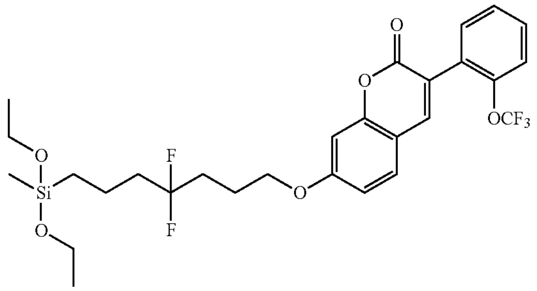
Si-051
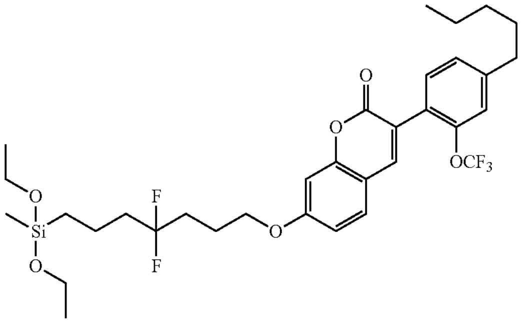
Si-052
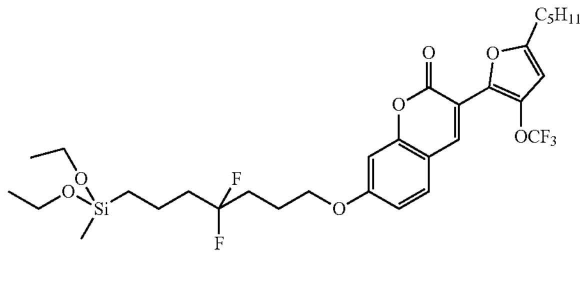
Si-053
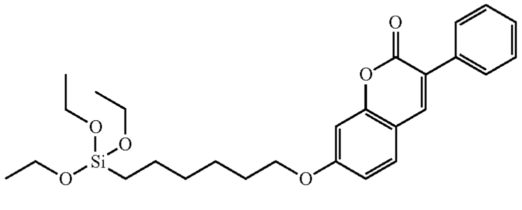

-continued
Si-054
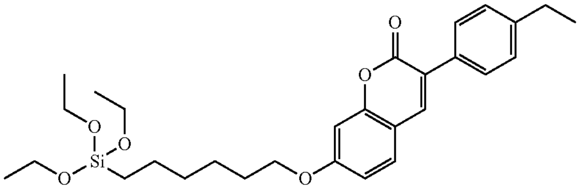
Si-055
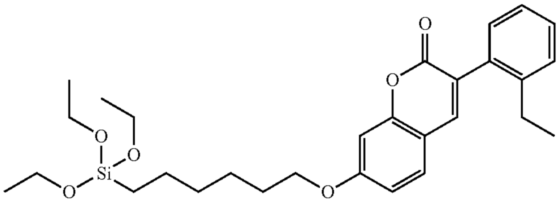
Si-056
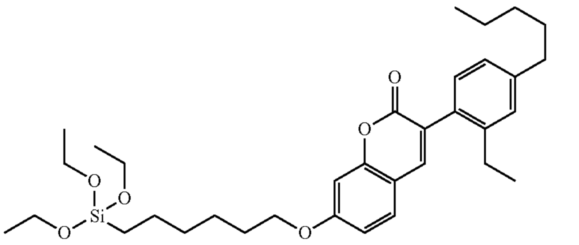
Si-057
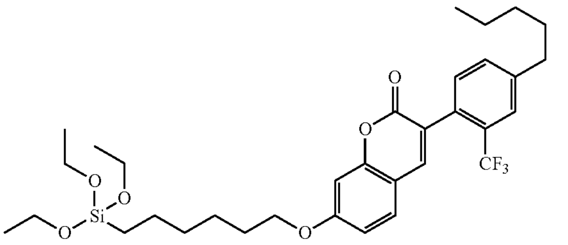
Si-058
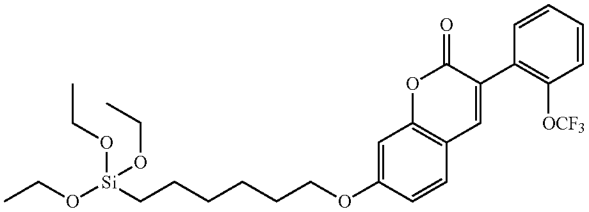
Si-059
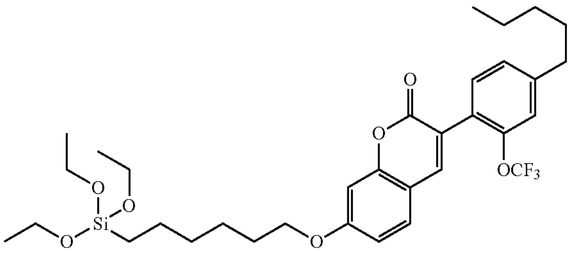
Si-060
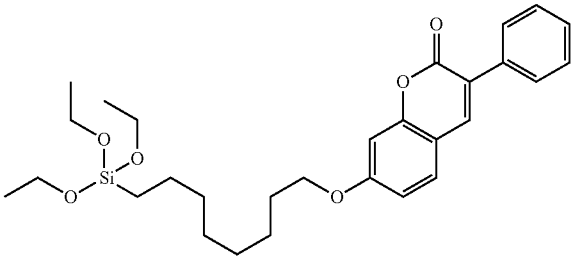
Si-061
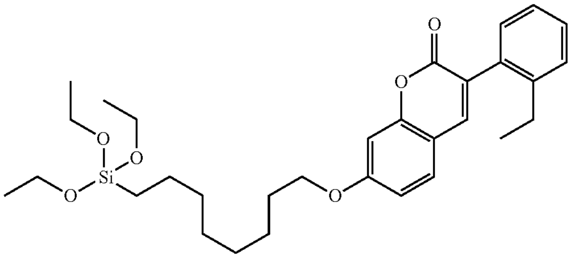
Si-062
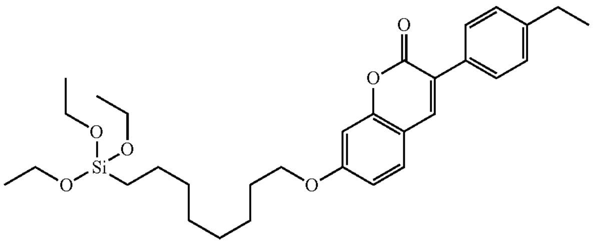
Si-063
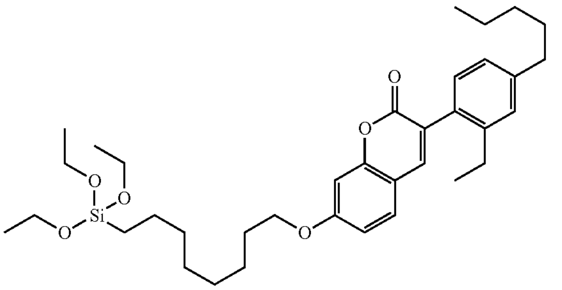

-continued
Si-064
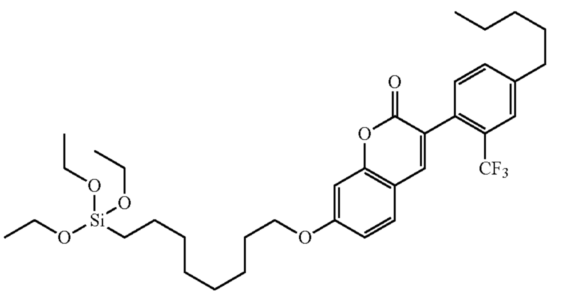
Si-065
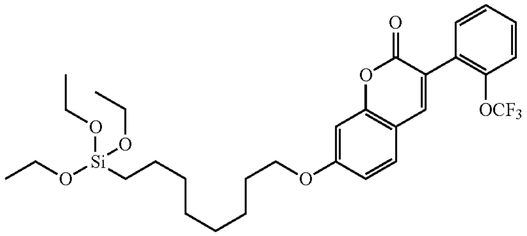
Si-066
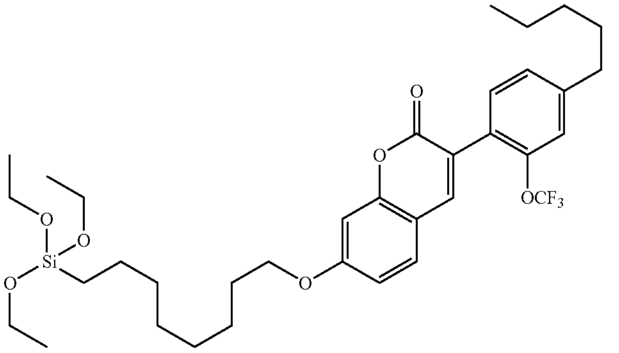
Si-067
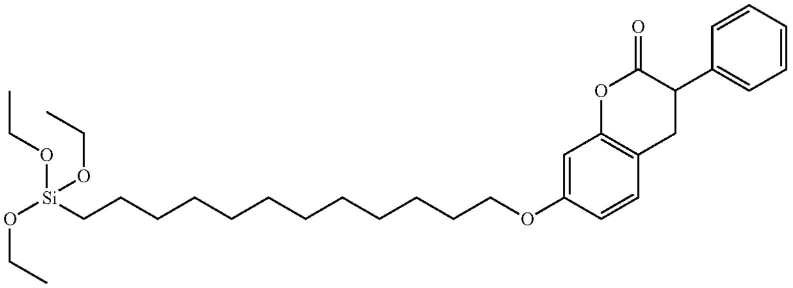
Si-068
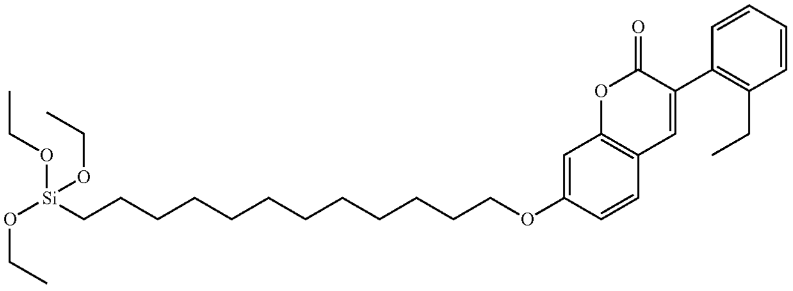
Si-069
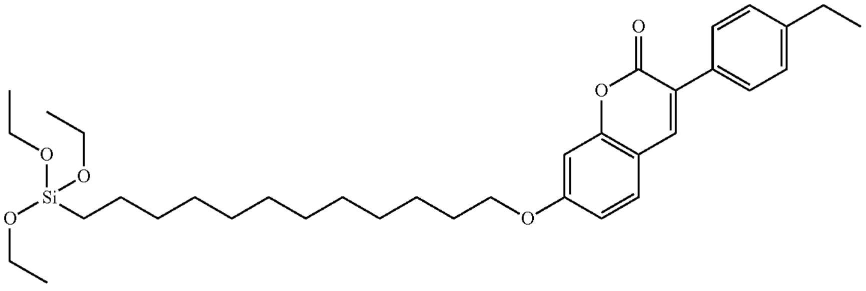

-continued
Si-070
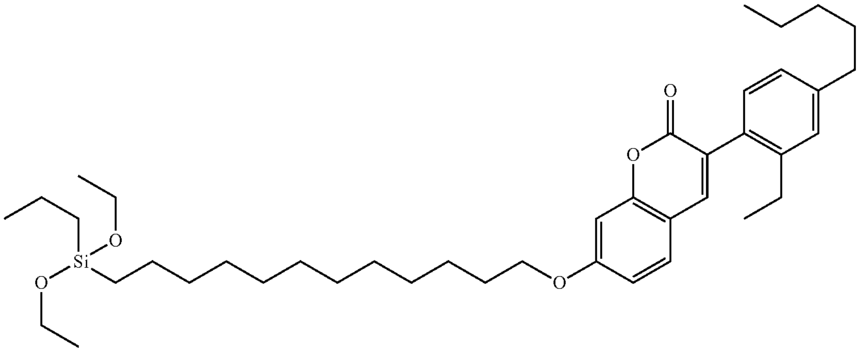
Si-071
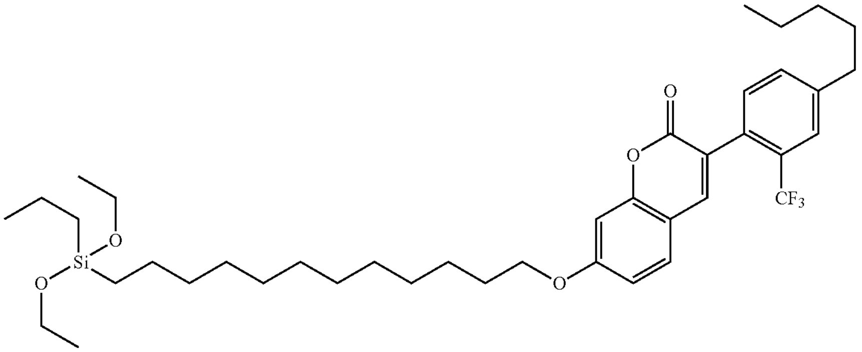
Si-072
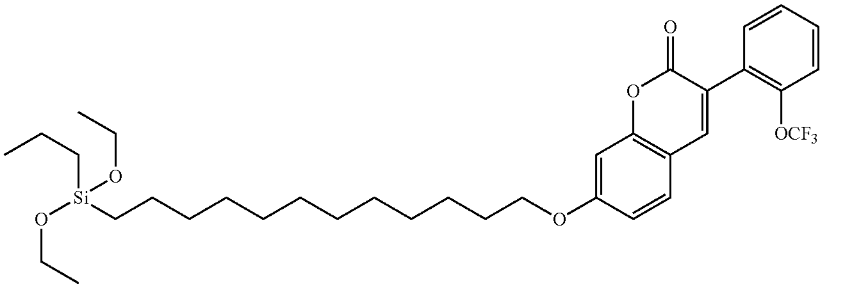
Si-073
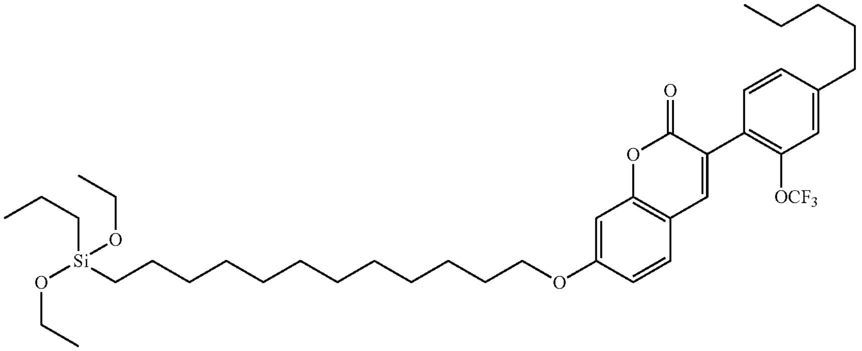
Si-074
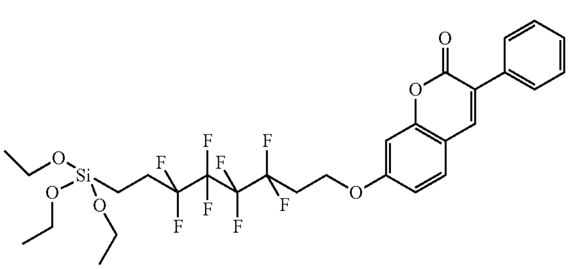
Si-075
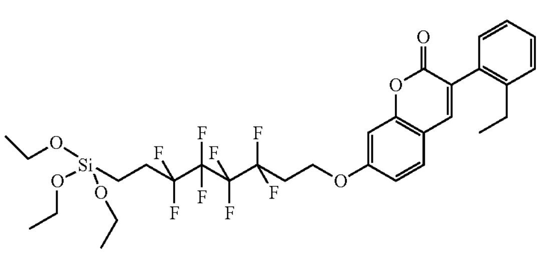

-continued
Si-076
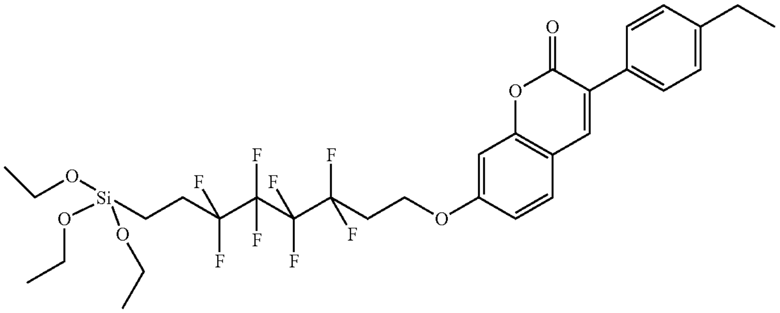
Si-077
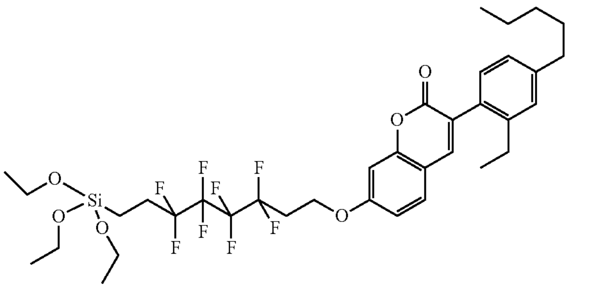
Si-078
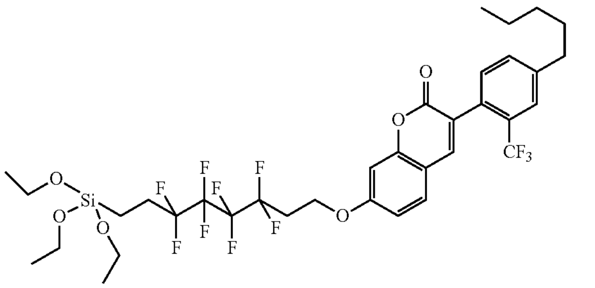
Si-079
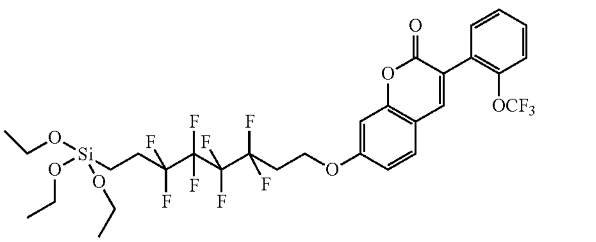
Si-080
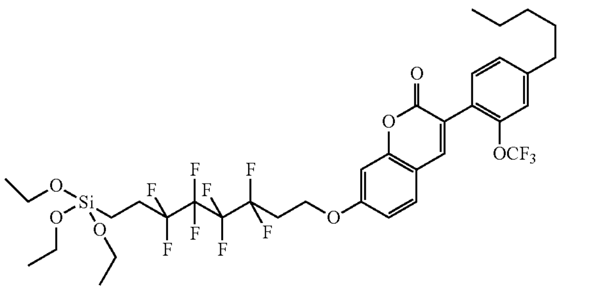
Si-081
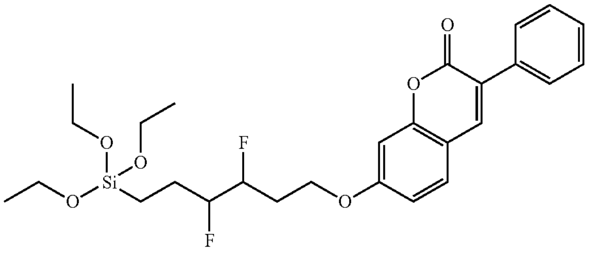
Si-082
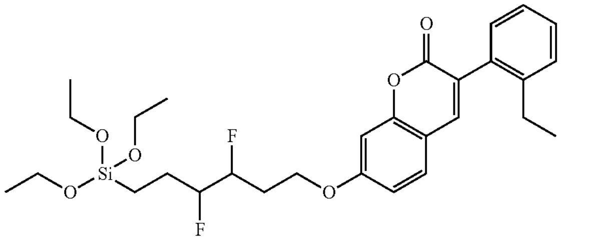
Si-083
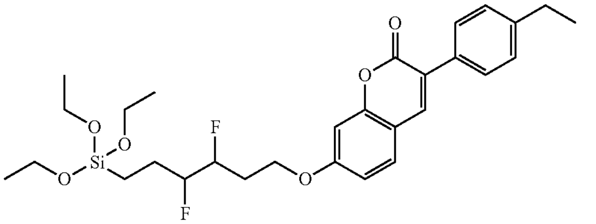
Si-084
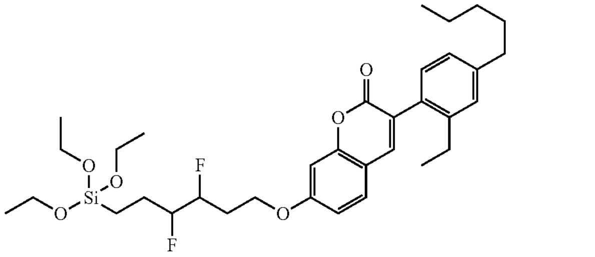

-continued
Si-085
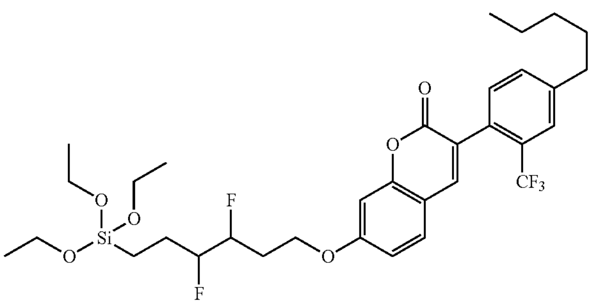
Si-086
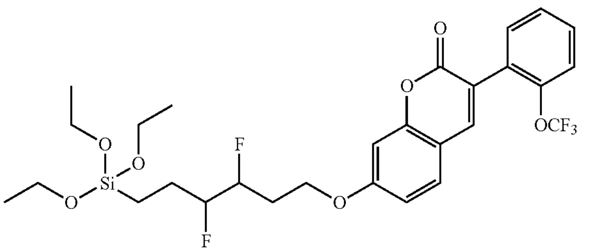
Si-087
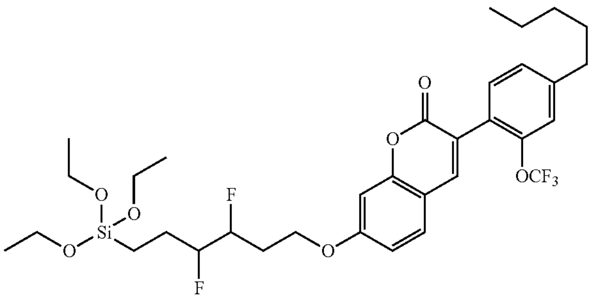
Si-088
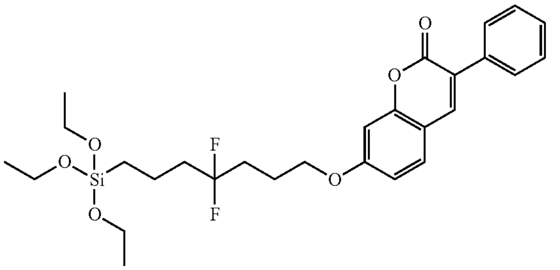
Si-089
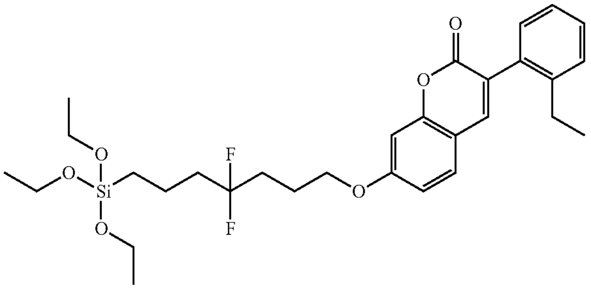
Si-090
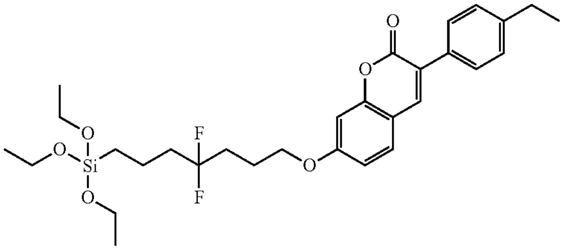
Si-091
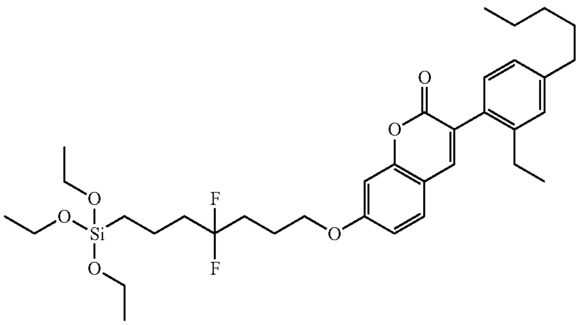
Si-092
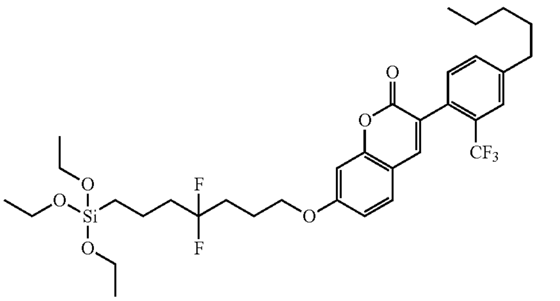
Si-093
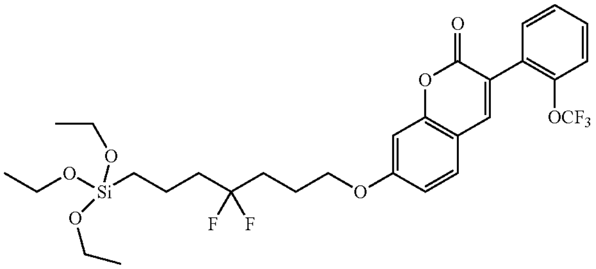
Si-094
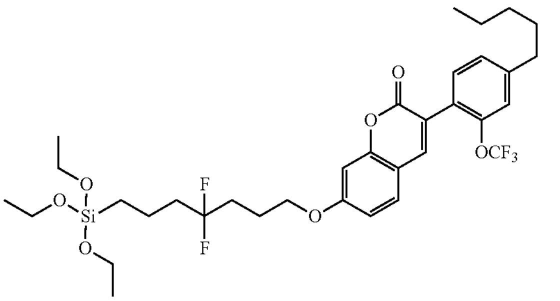

The compounds of the present application may be synthesized by methods well known to the skilled person. Preferably, all syntheses are carried out under an inert atmosphere using dried solvents.

An exemplary reaction sequence is shown in Scheme 1 for the compound Si-001.

Scheme 1

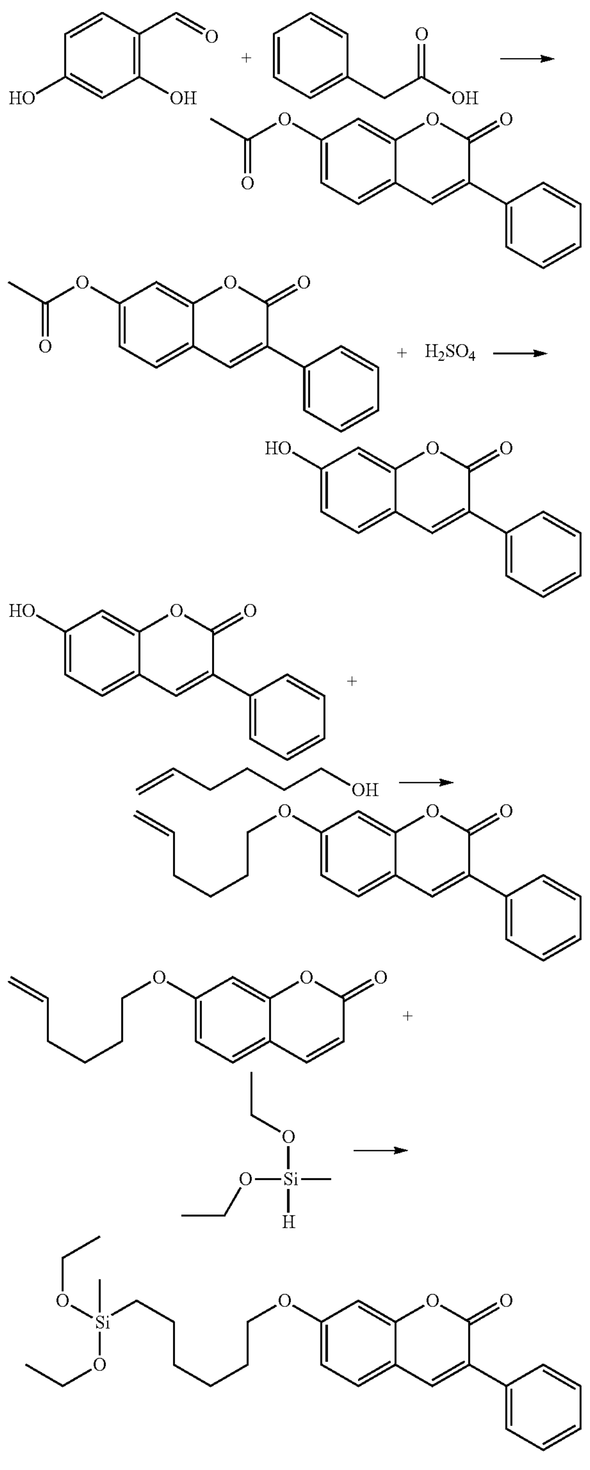

The first type of reaction is a classic Pechmann condensation in acetic anhydride.

The second type of reaction is an ester hydrolysis.

The third type is a Mitsunobu reaction.

The fourth type is a hydrosilylation reaction with Karstedt's catalyst.

All these types of reaction and their reaction conditions are well known to a skilled person and can be easily optimized for the specific starting materials forming the compounds of formula (I). More details can be found in the experimental section.

As described before, the compounds of formula (I), (I-1), (I-2), (I'), (I") and/or (I'") as described before or preferably described before contain a polymerizable group and are predestinated as monomers for an oligomerization or a polymerization.

The invention is therefore further directed to an oligomer or polymer comprising polymerized compounds of formula (I), (I-1), (I-2), (I'), (I") and/or (I'") as described before or preferably described before.

The term "polymer" generally means a molecule of high relative molecular mass, the structure of which essentially comprises the multiple repetition of units derived, actually or conceptually, from molecules of low relative molecular mass (PAC, 1996, 68, 2291). The term "polymer" includes homopolymers and co-polymers. The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having ≥30 repeating units, and an oligomer means a compound with >1 and <30 repeating units.

Above and below, in formulae showing a polymer, an oligomer, a compound of formula (I), (I-1) or (I-2) or a monomeric unit formed from a compound of formula (I), (I-1) or (I-2), an asterisk ("*") denotes a linkage to the adjacent repeating unit in the polymer chain or oligomer chain or to a terminal end group.

Suitable terminal end groups are known to the skilled artisan and depend on the polymerization method used.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

Unless stated otherwise, the molecular weight is given as the number average molecular weight $M_n$ or weight average molecular weight $M_W$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, tetrahydrofurane is used as solvent. The degree of polymerization (n) means the number average degree of polymerization given as $n=M_n/M_U$, wherein $M_U$ is the molecular weight of the single repeating unit as described in J. M. G. Cowie, *Polymers: Chemistry & Physics of Modern Materials*, Blackie, Glasgow, 1991. The polydispersity (PDI) means the ratio of weight average molecular weight $M_w$, divided by the number average molecular weight $M_n$ and is described with the letter D. The value of D is dimensionless and describes the broadness of the molecular weight distribution. The value of D can be calculated from the obtained values ($M_w$, $M_n$) from the GPC analysis.

In the polymers according to the present invention, the total number of repeating units n is preferably ≥30, very preferably ≥100, most preferably ≥200, and preferably up to 5000, very preferably up to 3000, most preferably up to 2000, including any combination of the aforementioned lower and upper limits of n.

The polymers of the present invention include homopolymers, statistical co-polymers, random co-polymers, alternating co-polymers and block co-polymers, and combinations of the aforementioned.

Throughout the description and claims of this specification, the words “comprise” and “contain” and variations of the words, for example “comprising” and “comprises”, mean “including but not limited to”, and are not intended to (and do not) exclude other components Preferably the polymerizable group $R_1$ forms the regioregular, alternated, regiorandom, statistical, block or random homopolymer or co-polymer backbone or is part of the polymer backbone where $R_1$ has a meaning as described or preferably described before. Preferably, such oligomer or polymer comprises a constitutional unit $M^0$ of formulae (1-p-1), (1-p-2), (1-p-3), (1-p-4), (1-p-5), (1-p-6), (1-p-7), (1-p-8), (1-p-9), (1-p-10) and (1-p-11), (1-p-1)

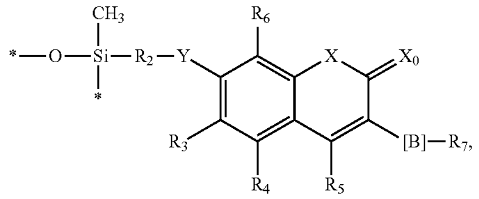

(1-p-2)

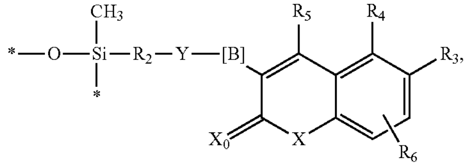

(1-p-3)

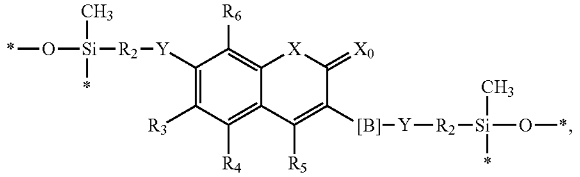

(1-p-4)

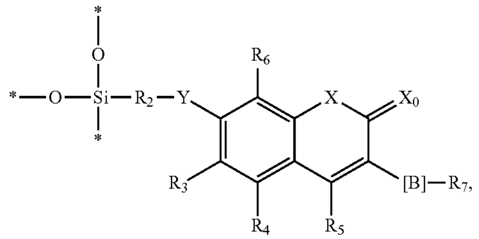

(1-p-5)

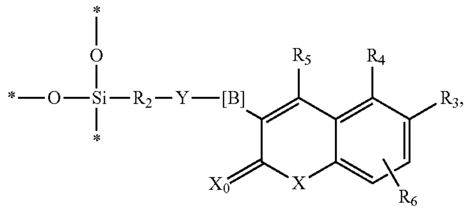

-continued (1-p-6)

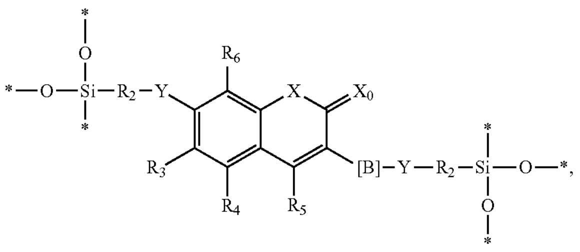

(1-p-7)

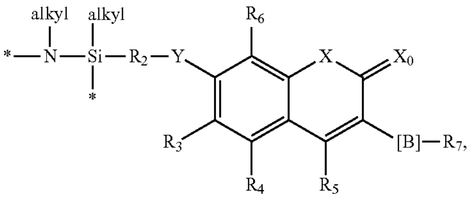

(1-p-8)

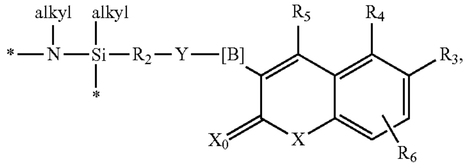

(1-p-9)

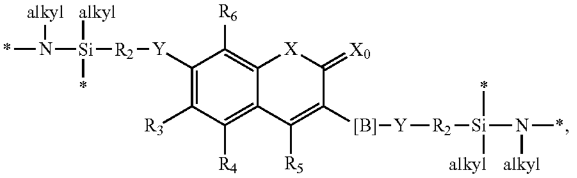

(1-p-10)

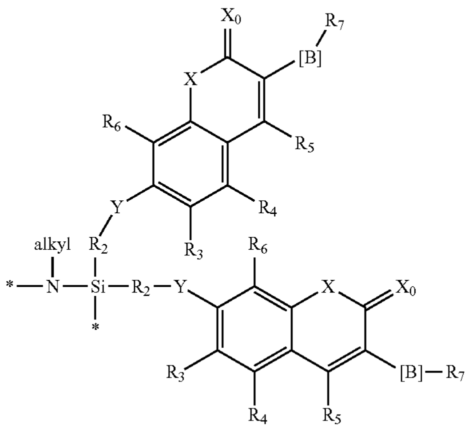

-continued (1-p-11)

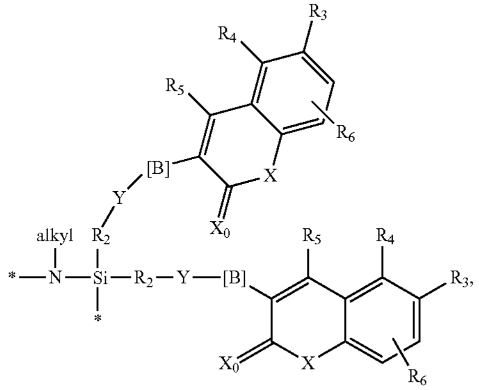

wherein

—$R_2$—, Y, $R_3$, $R_4$, $R_5$, $R_6$, X, $X_0$, —[B]—, $R_7$ and "alkyl" have a meaning or a preferred meaning as described or preferably described before. Combinations are excluded where two O atoms, two N atoms, an O atom and a S atom or an O atom and a N atom are directly linked to each other as known for a skilled artisan in the field of organic chemistry.

The co-polymer may be an oligomer or polymer comprising one or more polymerized compounds of formula (I), (I-1), (I-2), (I'), (I'') or (I''') or a constitutional unit $M^0$ of formulae (1-p-1) to (1-p-11), which may be the same or different from one another, and one or more constitutional units $M^2$, which may be the same or different from one another. Said one or more constitutional units $M^2$ are chemically different from the units $M^0$. Preferably, said one or more constitutional units $M^2$ are derived by polymerization of one or more monomers selected from the group consisting of trialkoxyalkenylsilane, dialkoxyalkylalkenylsilane or a silane of formula (8) and (9), (8)

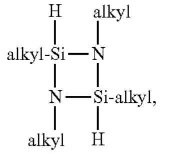

(9)

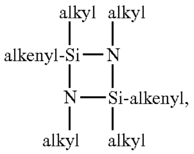

where the alkyl and alkoxy groups are at each occurrence independently of each other linear or branched having 1 to 6 C atoms and where the alkenyl group is at each occurrence independently linear having 2 to 4 C atoms.

Preferably, the alkenyl group is vinyl.

Particularly preferably, said one or more constitutional units $M^2$ are derived by polymerization of one or more monomers selected from the group consisting of trialkoxyalkenylsilane and dialkoxyalkylalkenylsilane, where the alkyl and alkoxy groups are each independently linear or branched having 1 to 6 C atoms and where the alkenyl group is at each occurrence independently linear having 2 to 4 C atoms with inventive monomers as described before or preferably described before.

Alternatively the oligomer or polymer according to the invention is a homopolymer, i.e. an oligomer or polymer comprising one or more constitutional unit $M^0$ of formula of formulae (1-p-1) to (1-p-11), wherein all constitutional units $M^0$ are the same.

Exemplary polymeric compounds may be selected from the following formulae (P-001) to (P-094):

P-001

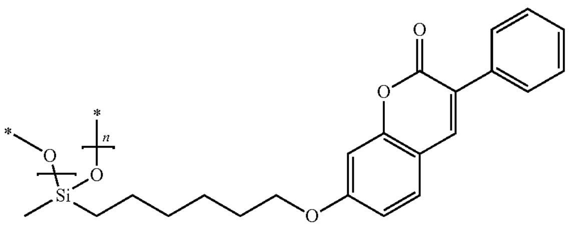

P-002

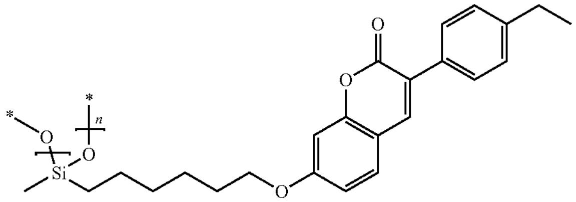

P-003

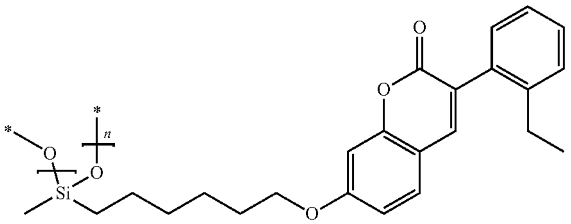

P-004

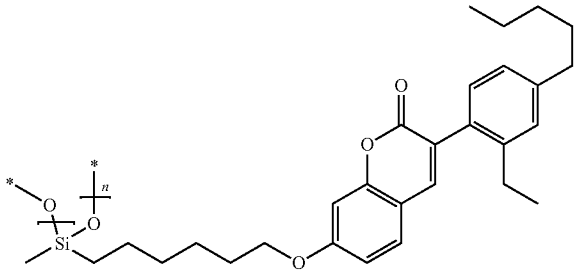

-continued
P-005
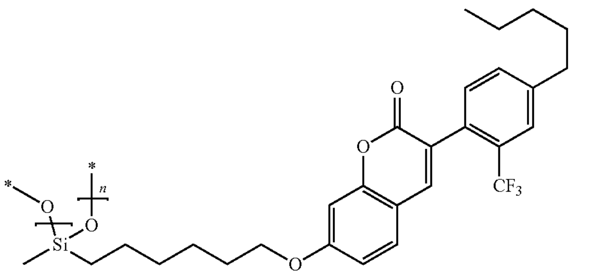
P-006
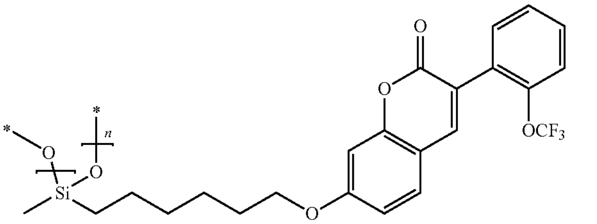
P-007
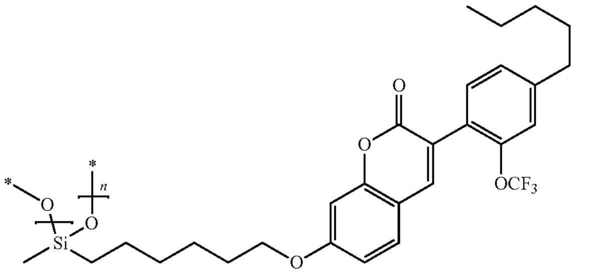
P-008
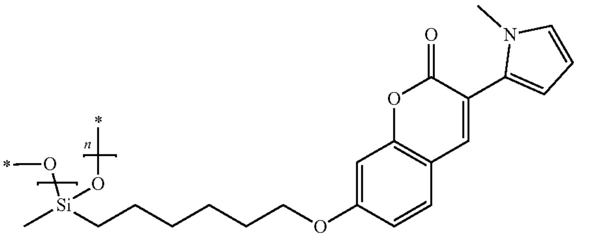
P-009
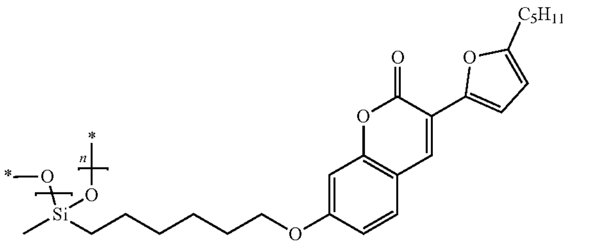
P-010
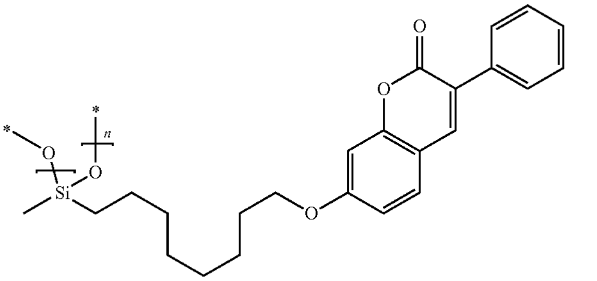
P-011
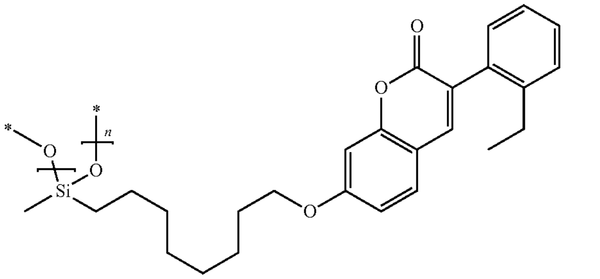
P-012
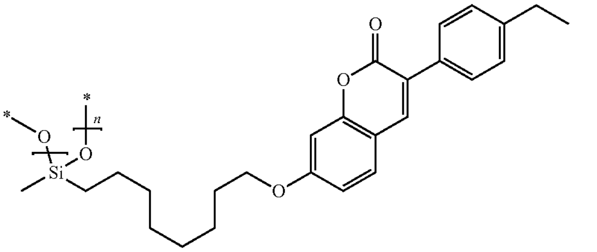
P-013
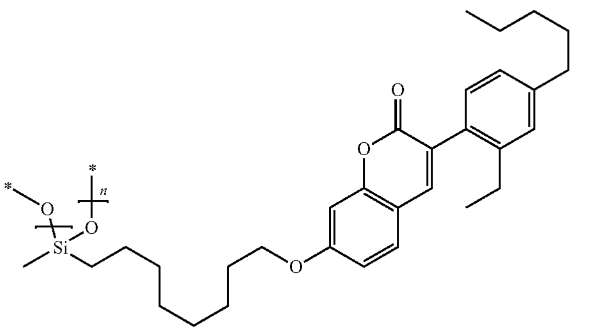
P-014
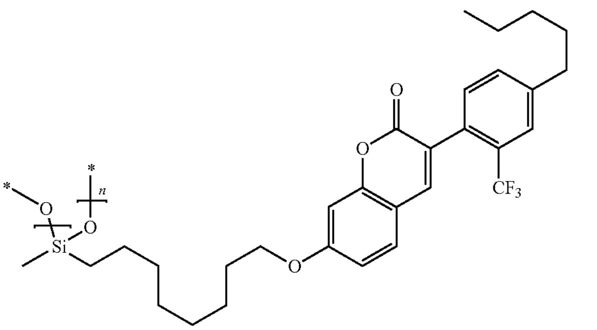

-continued
P-015
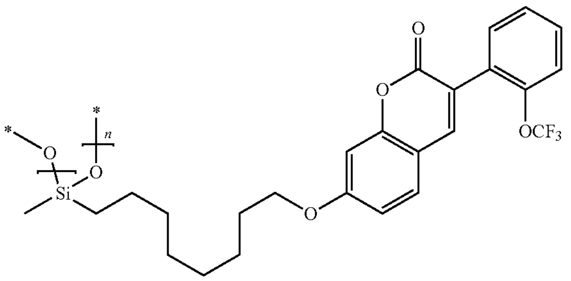
P-016
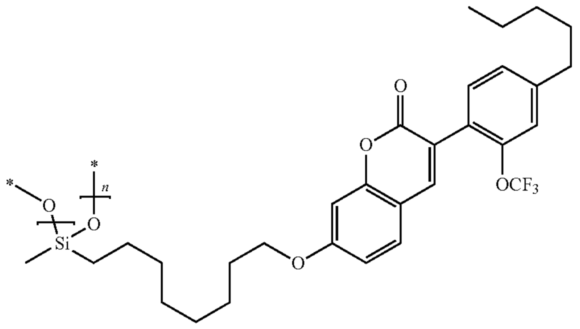
P-017
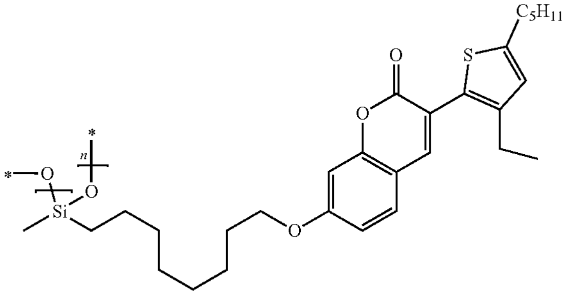
P-018
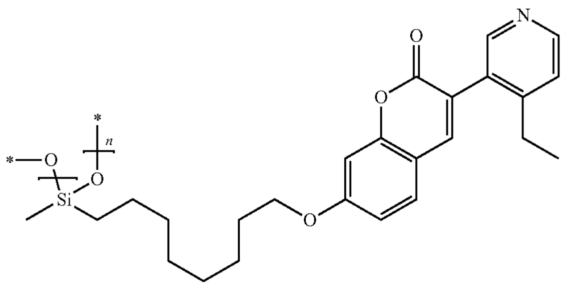
P-019
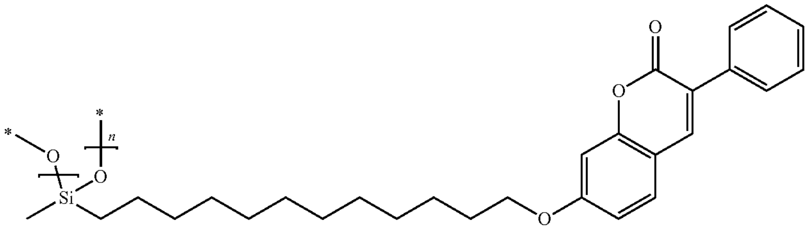
P-020
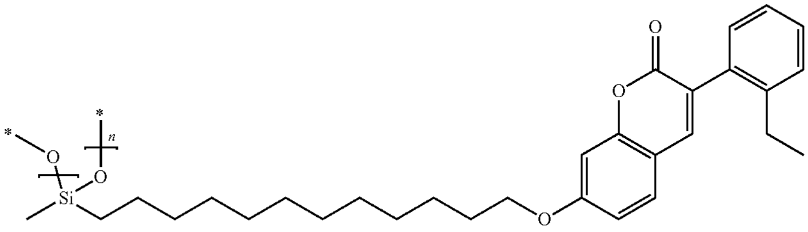
P-021
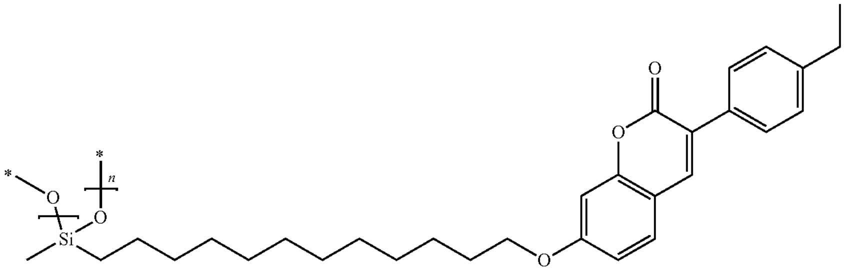

-continued
P-022
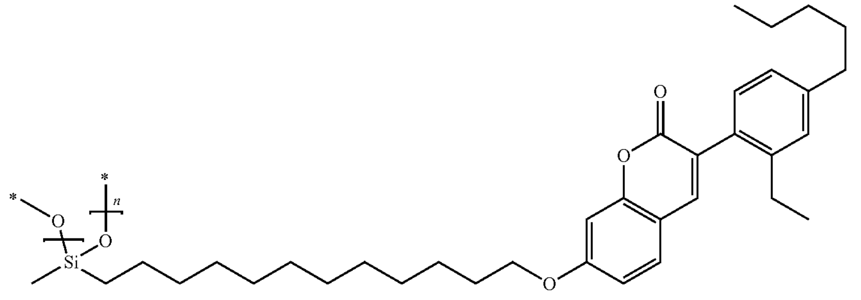
P-023
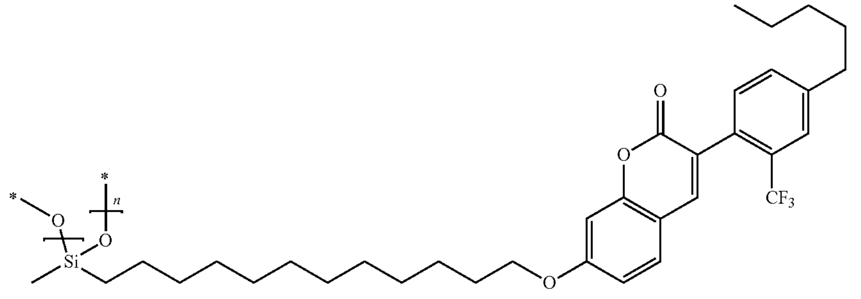
P-024
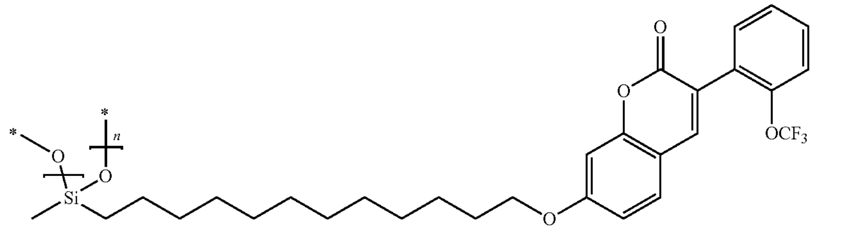
P-025
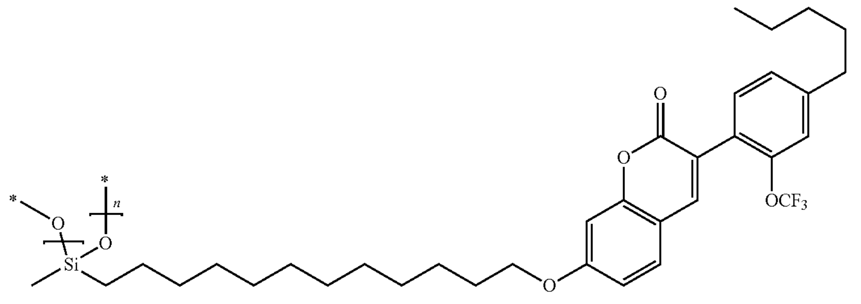
P-026
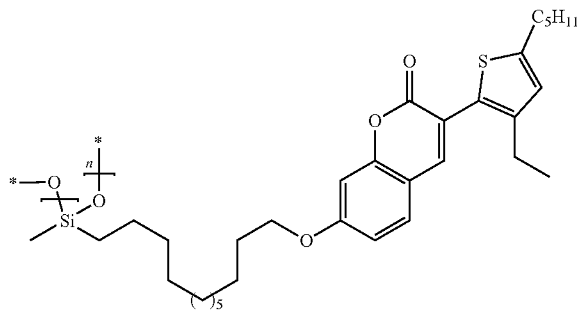
P-027
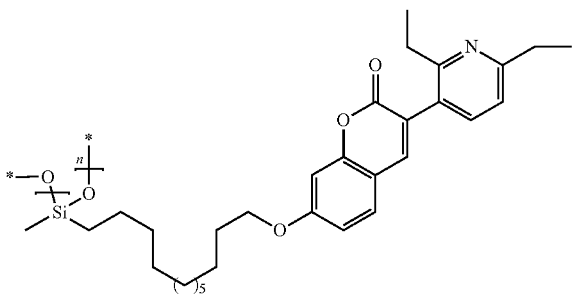

-continued
P-028
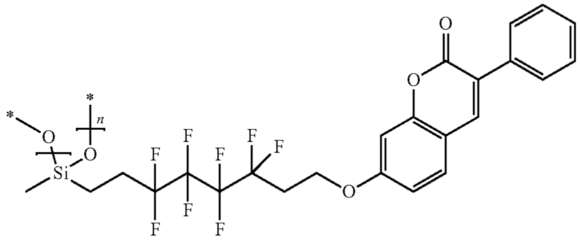
P-029
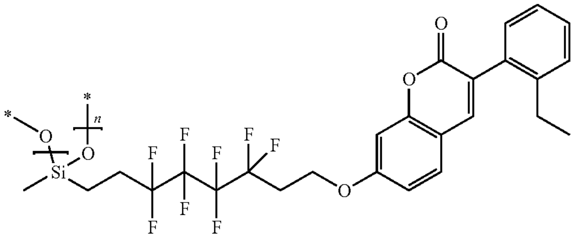
P-030
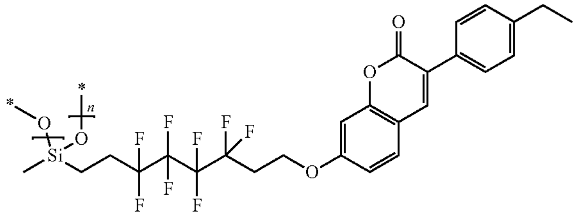
P-031
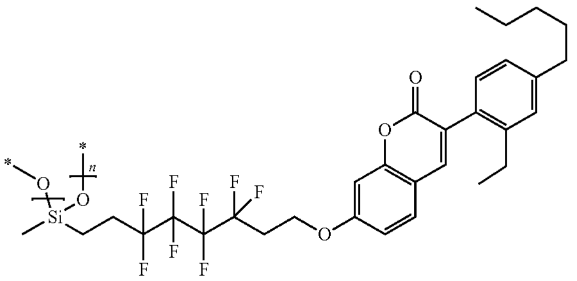
P-032
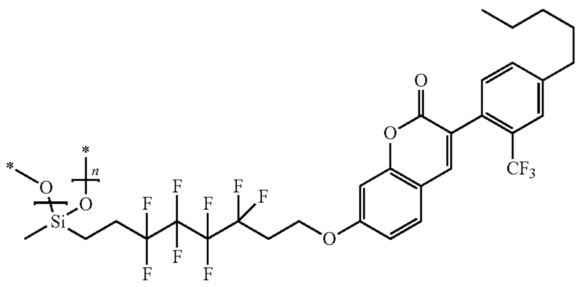
P-033
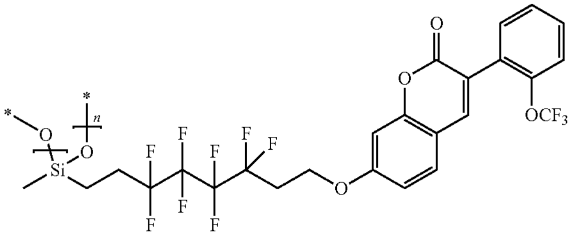
P-034
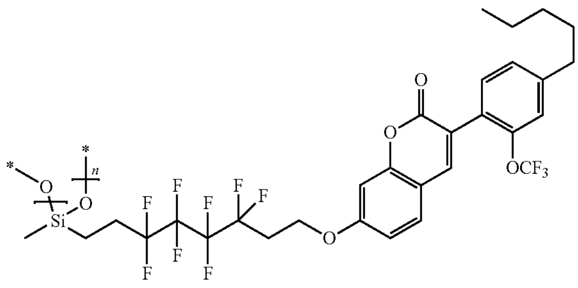
P-035
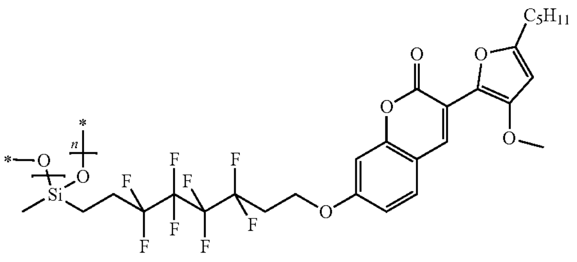
P-036
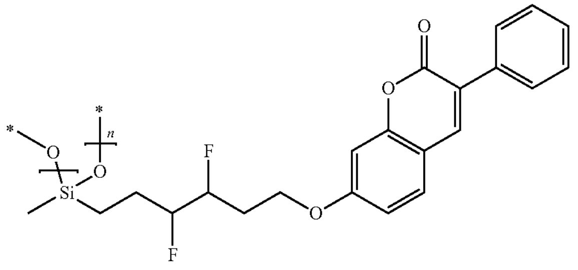
P-037
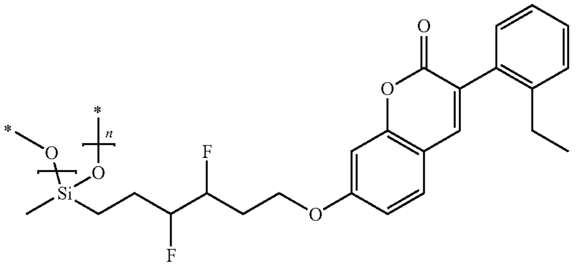

-continued
P-038
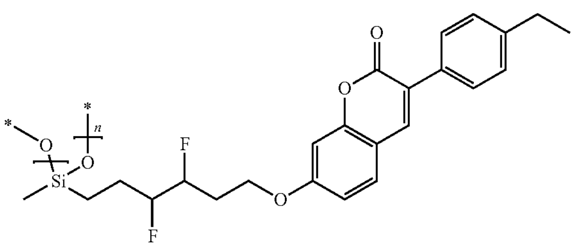
P-039
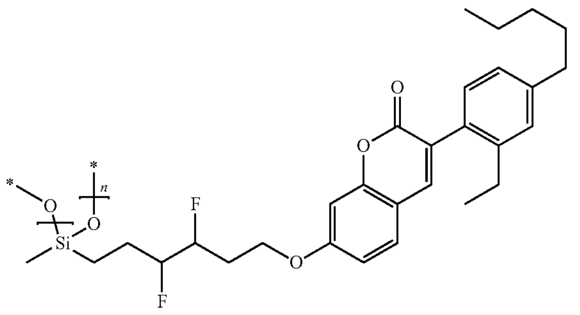
P-040
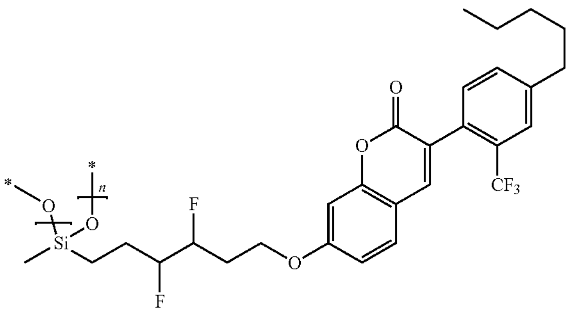
P-041
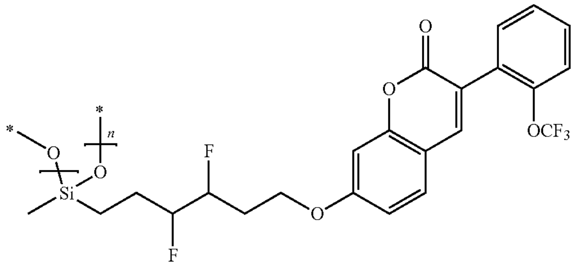
P-042
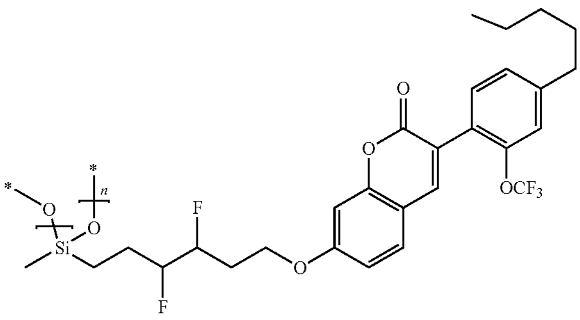
P-043
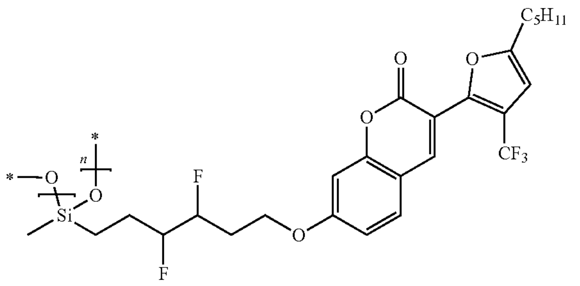
P-044
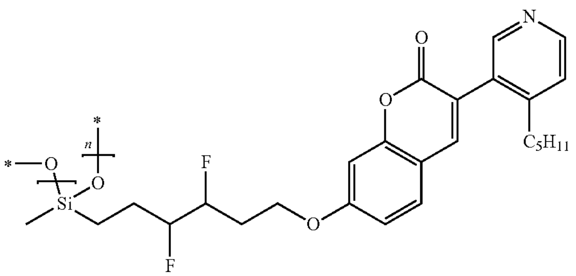
P-045
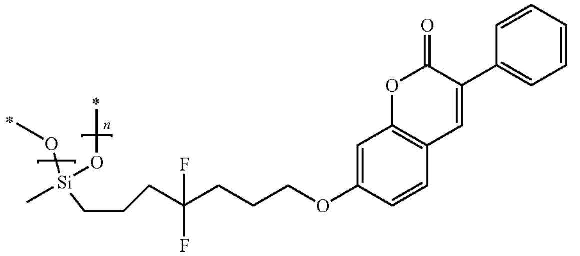
P-046
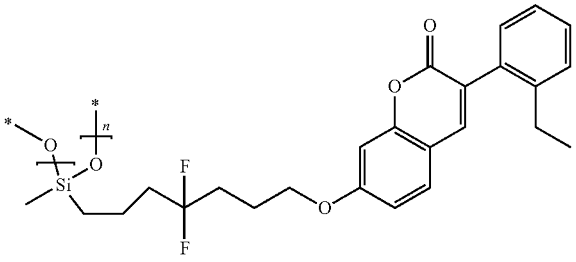
P-047
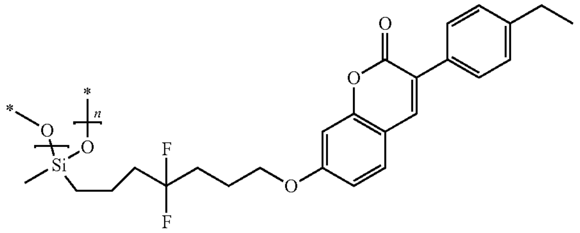

-continued
P-048
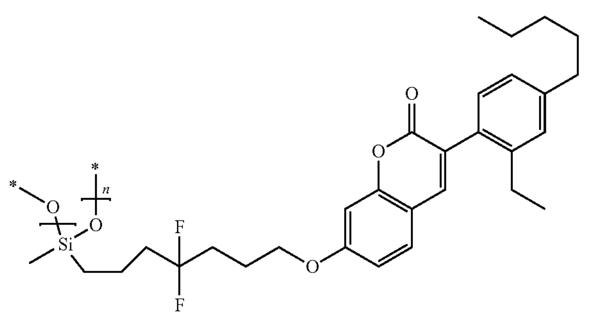
P-049
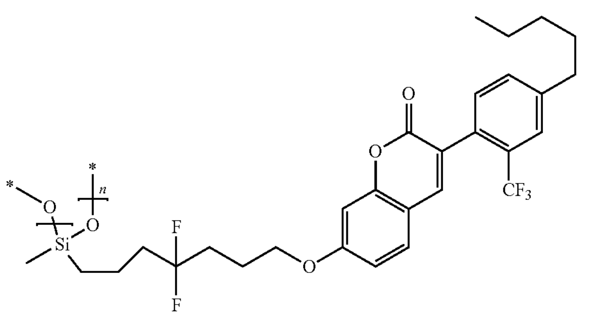
P-050
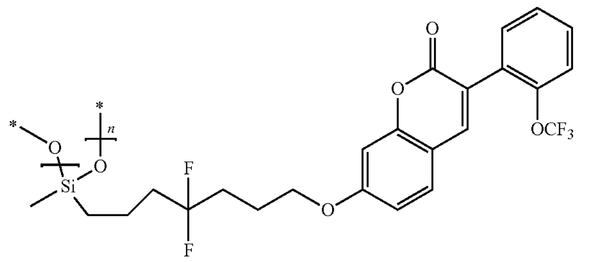
P-051
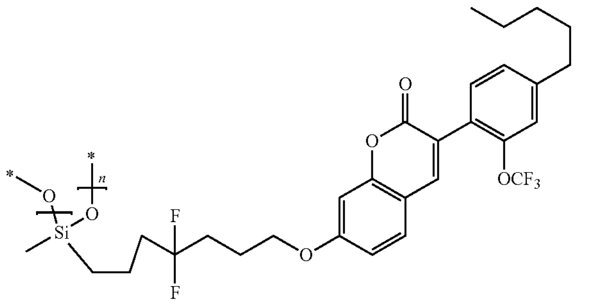
P-052
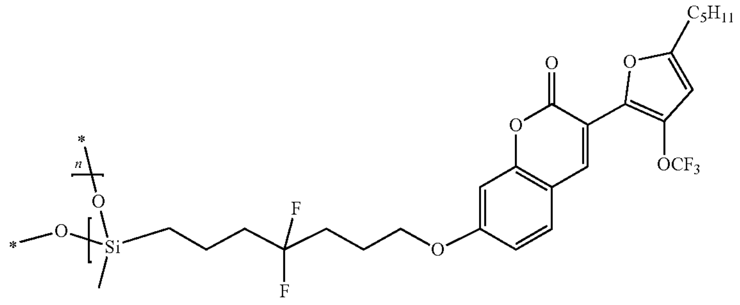
P-053
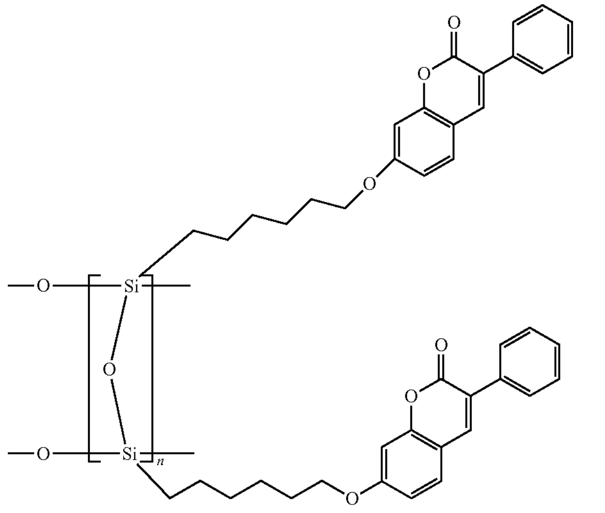
P-054
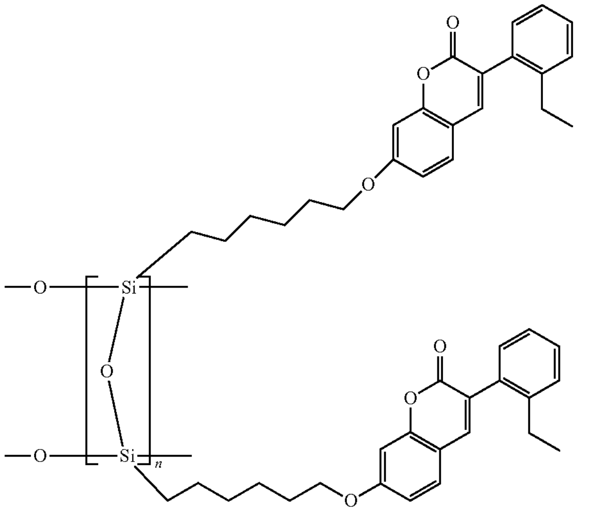

-continued
P-055
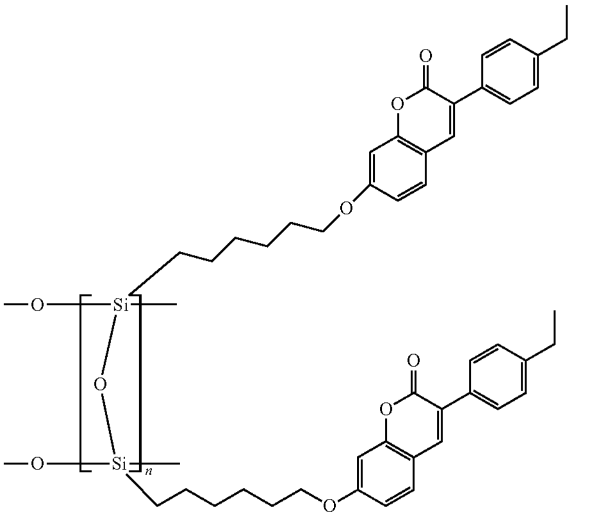
P-056
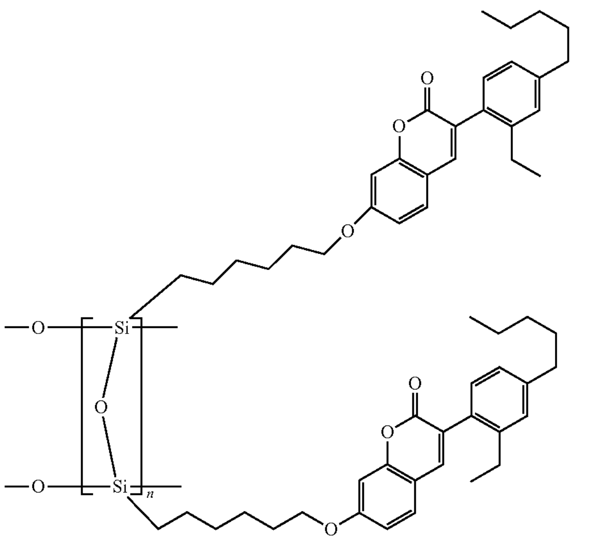
P-057
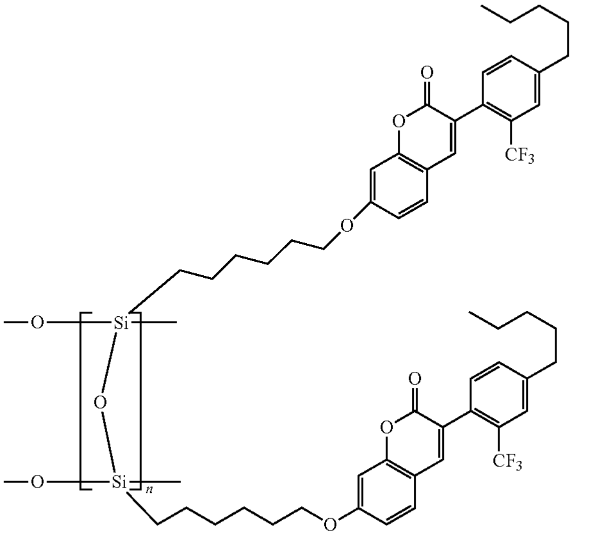
P-058
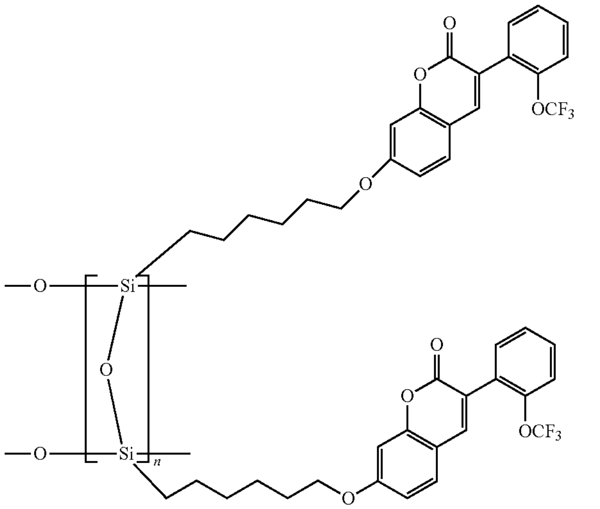
P-059
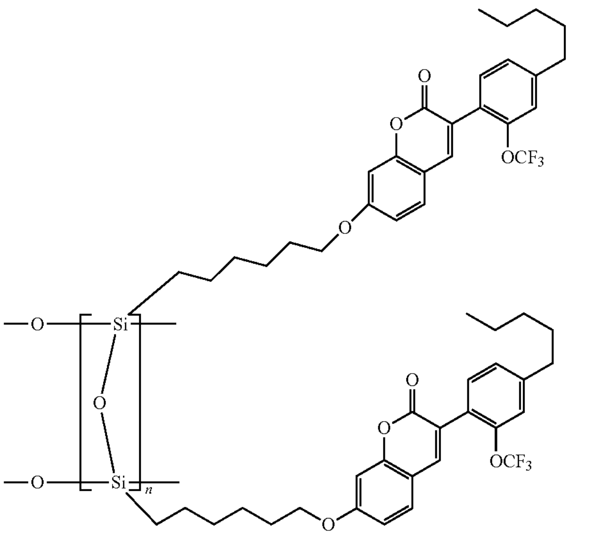
P-060
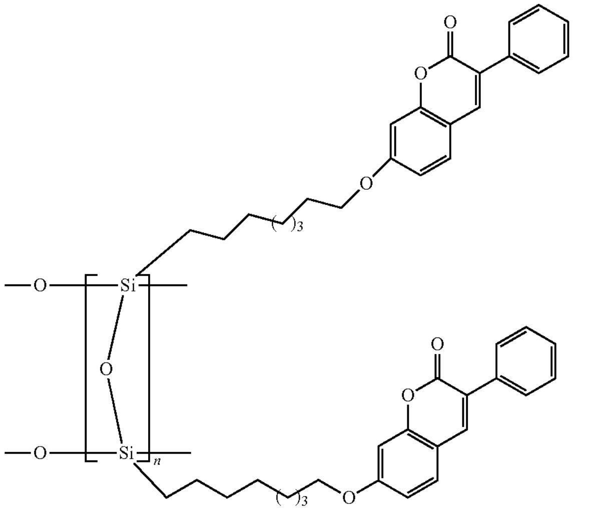

-continued
P-061
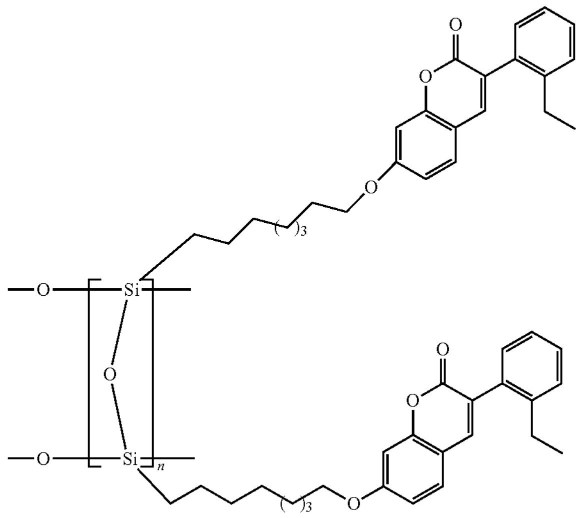
P-062
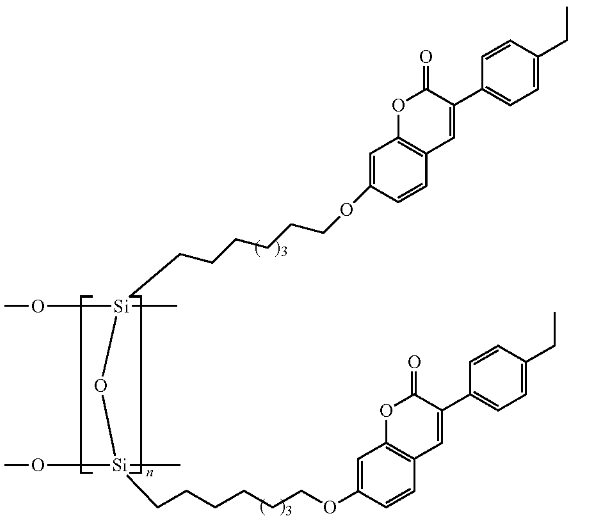
9-063
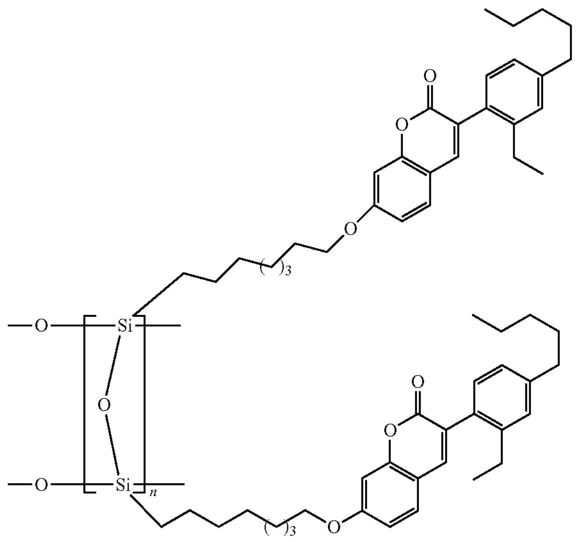
P-064
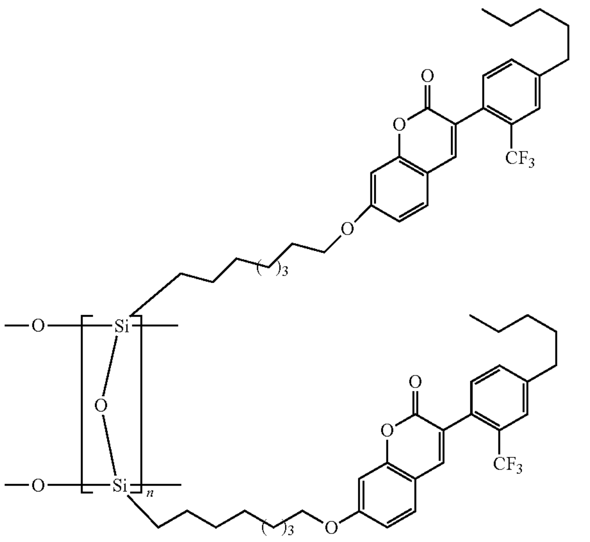
P-065
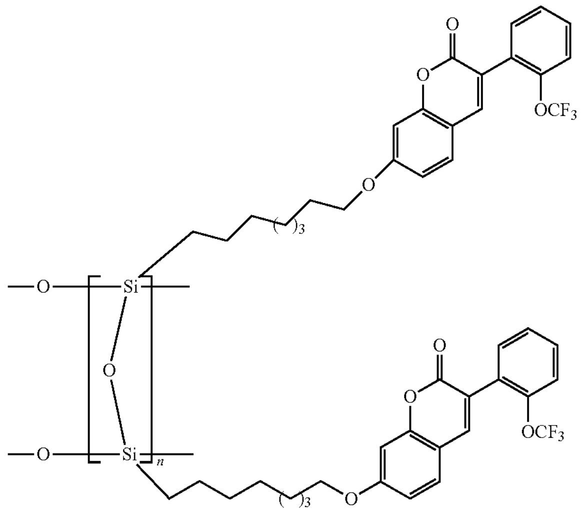
P-066
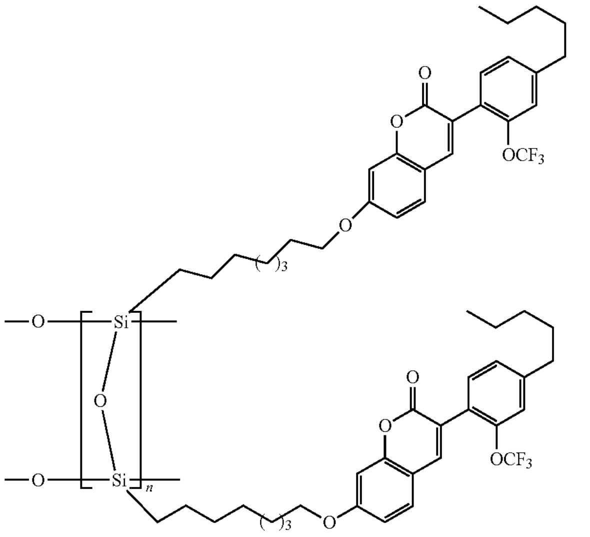

-continued
P-067
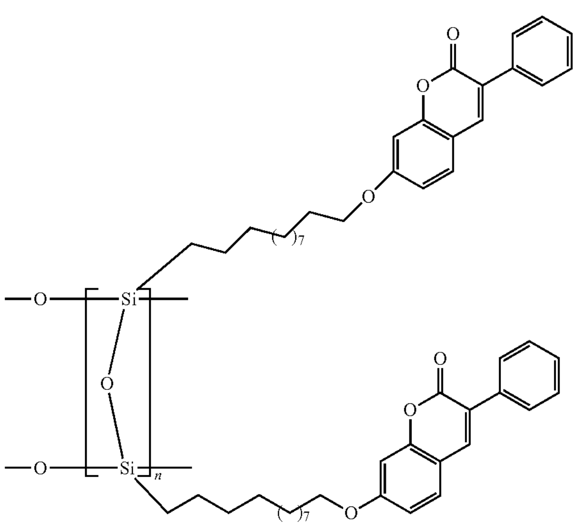
P-068
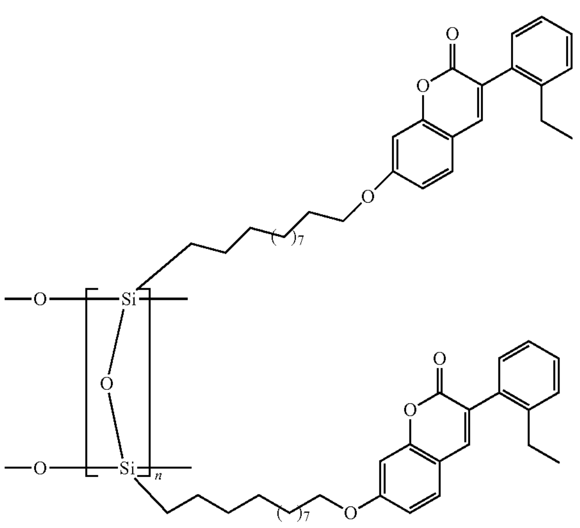
P-069
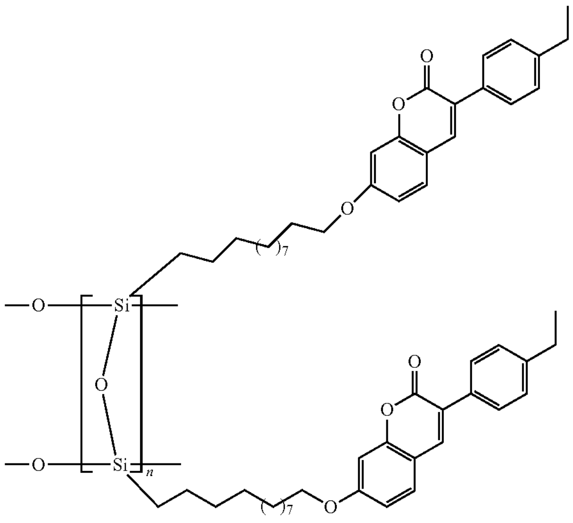
P-070
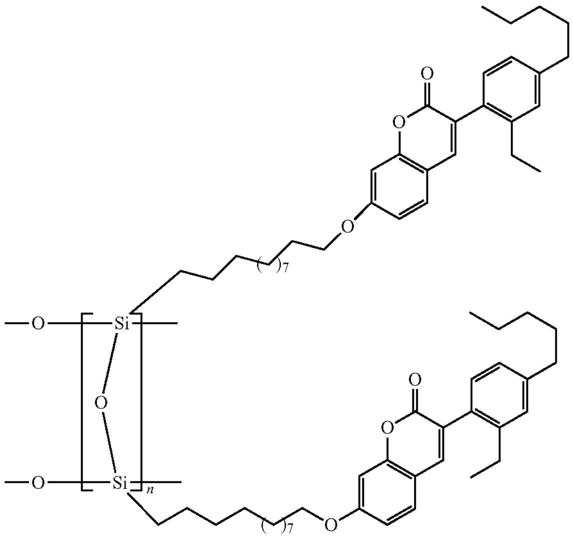
P-071
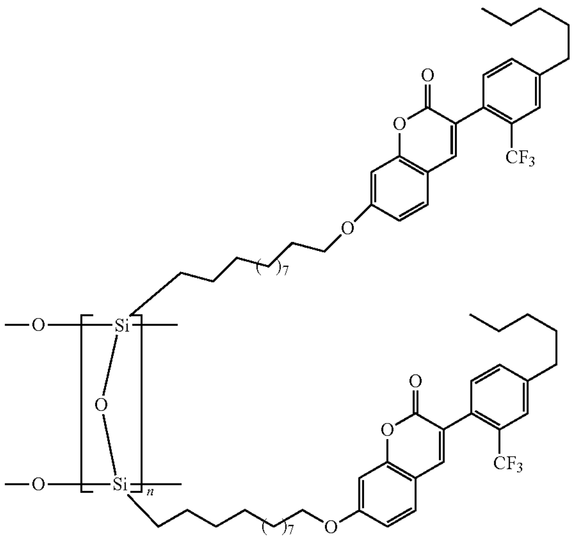
P-072
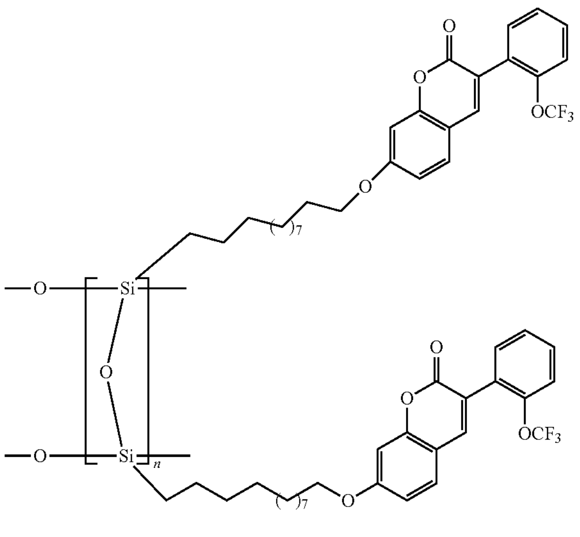

-continued
P-073
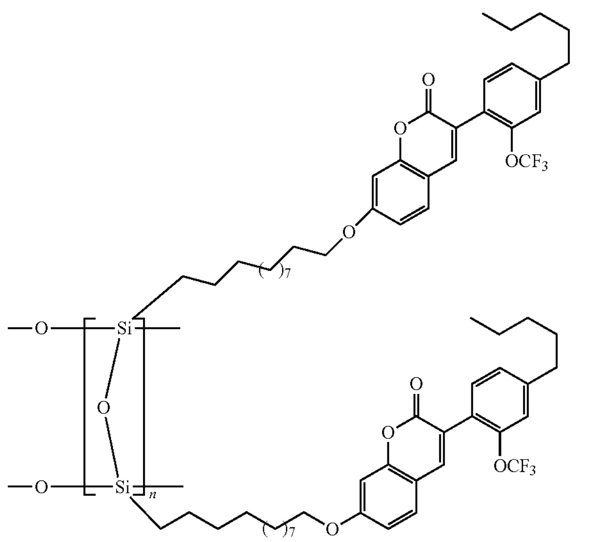
P-074
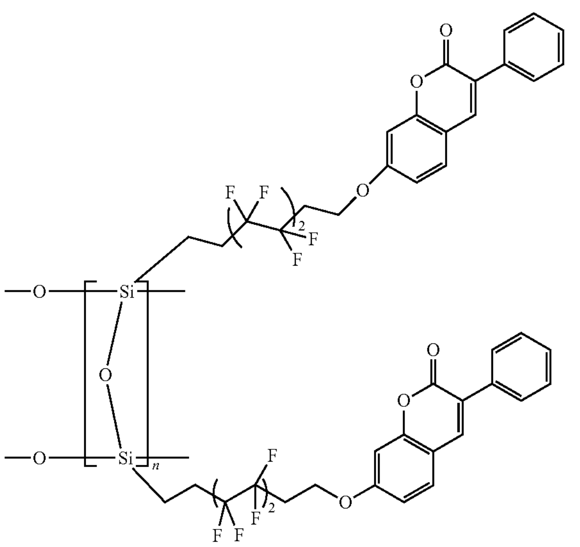
P-075
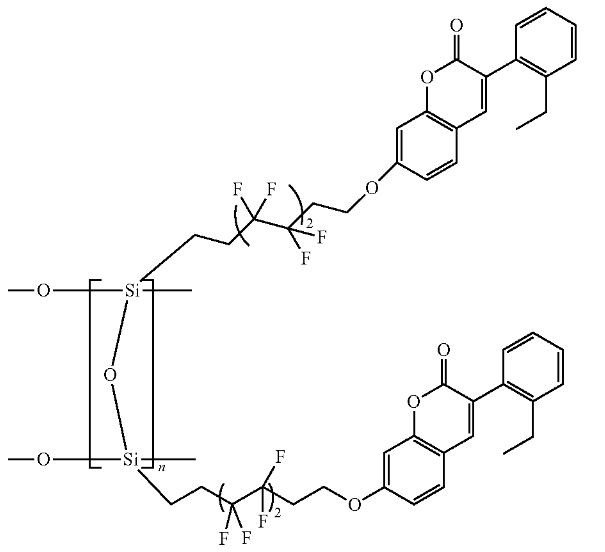
P-076
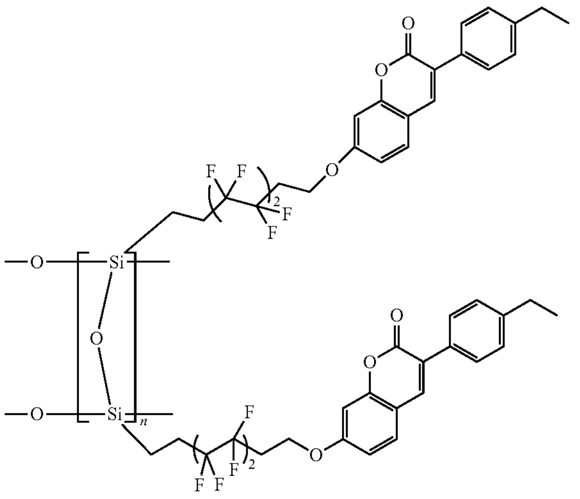

-continued
P-077
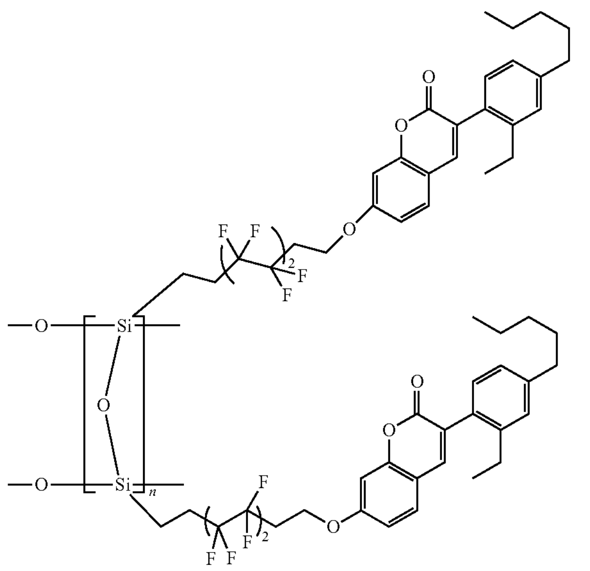
P-078
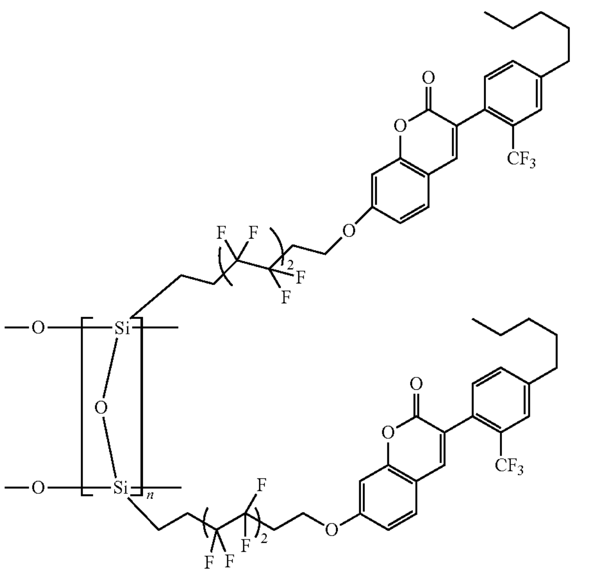
P-079
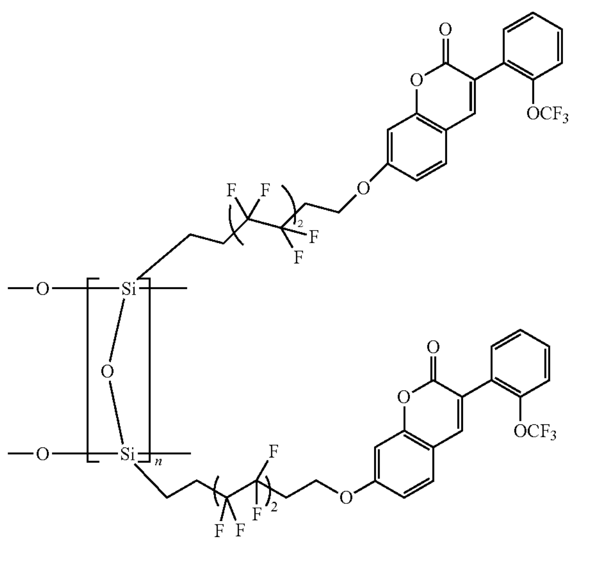
P-080
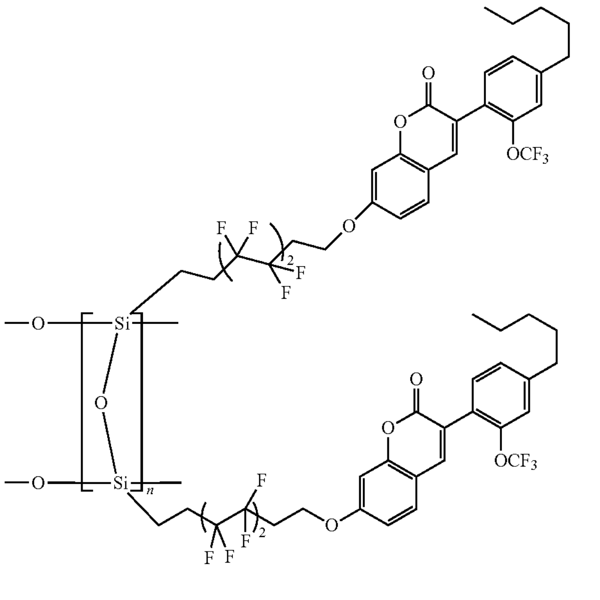

-continued
P-081
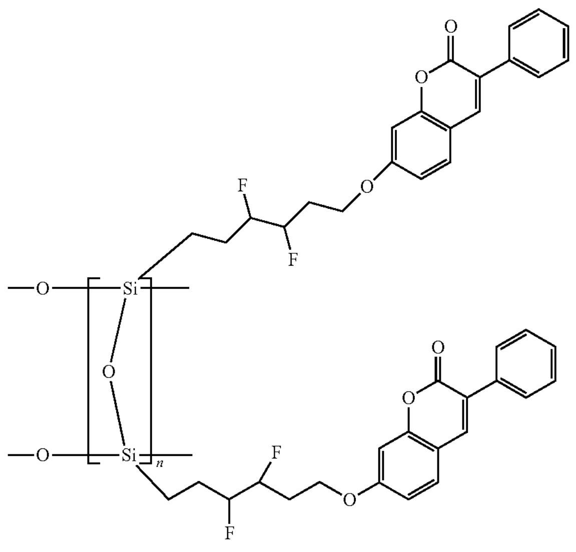
P-082
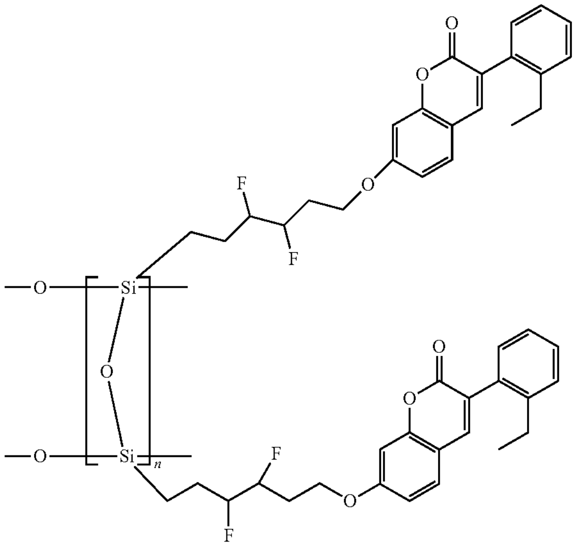
P-083
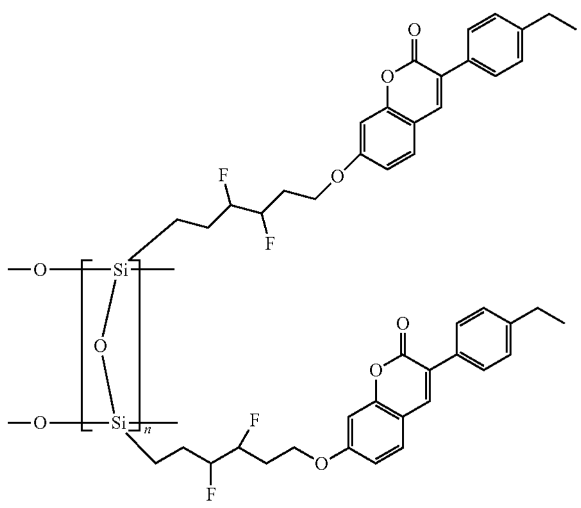
P-084
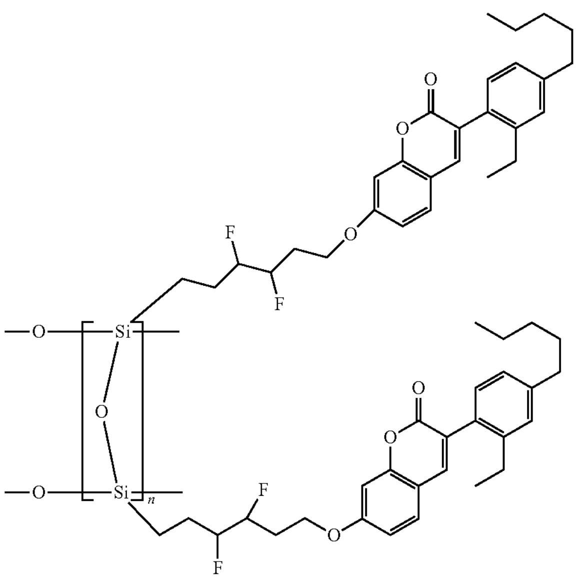

-continued
P-085
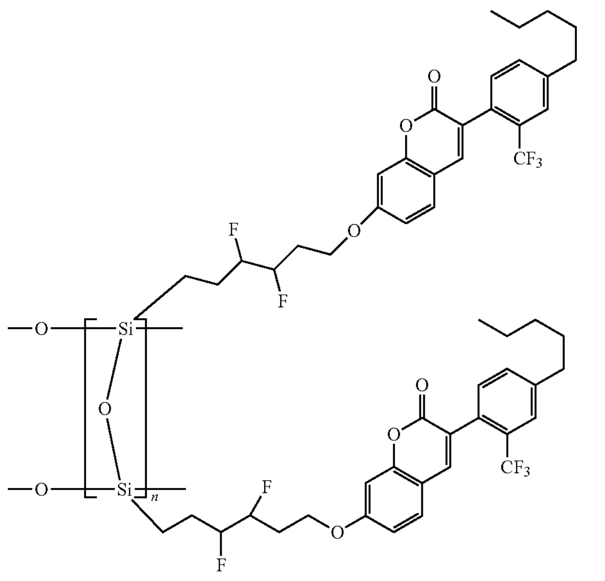
P-086
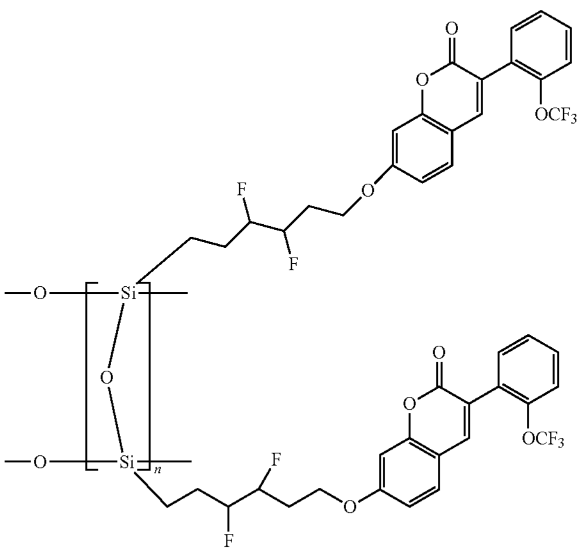
P-087
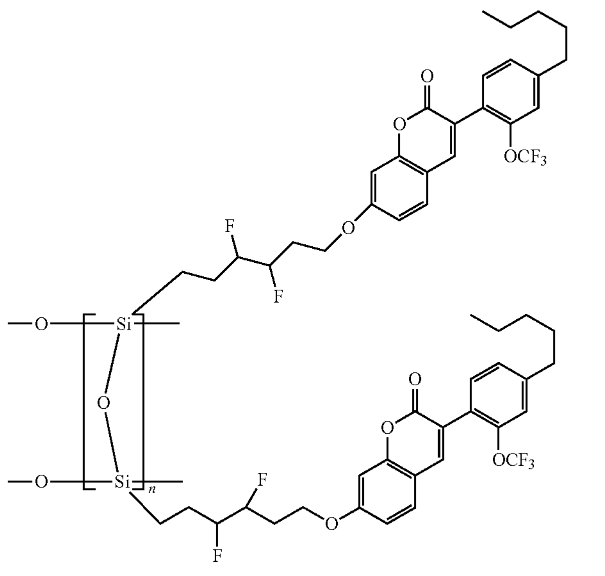
P-088
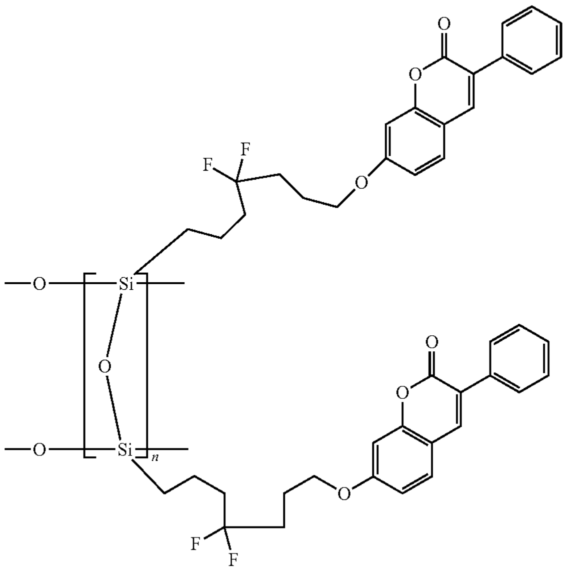

-continued
P-089
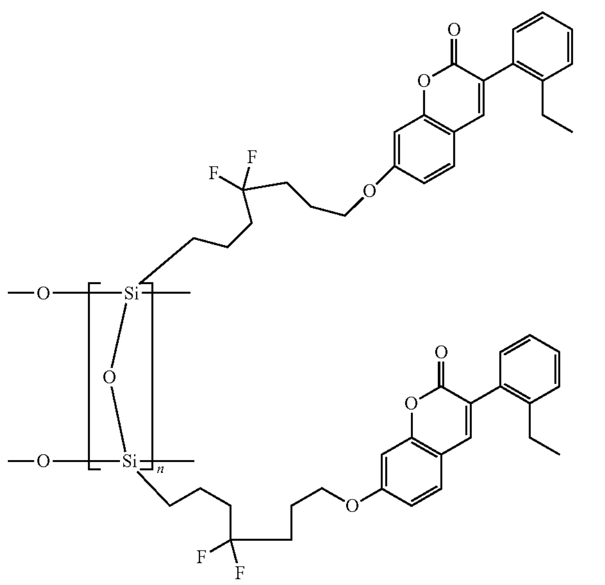
P-090
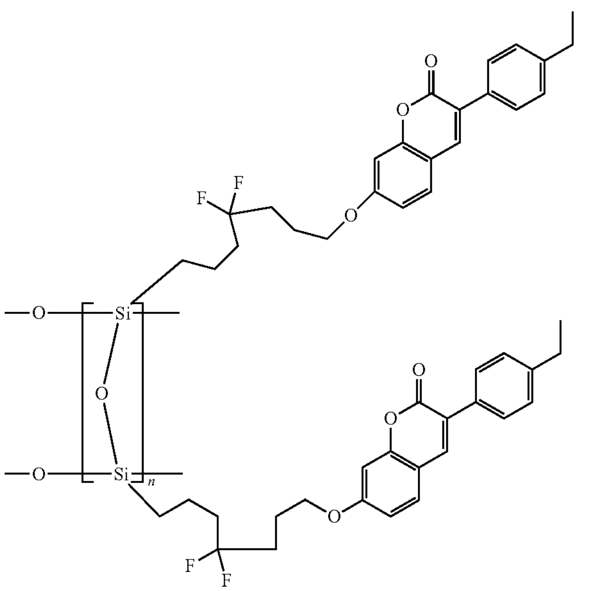
P-091
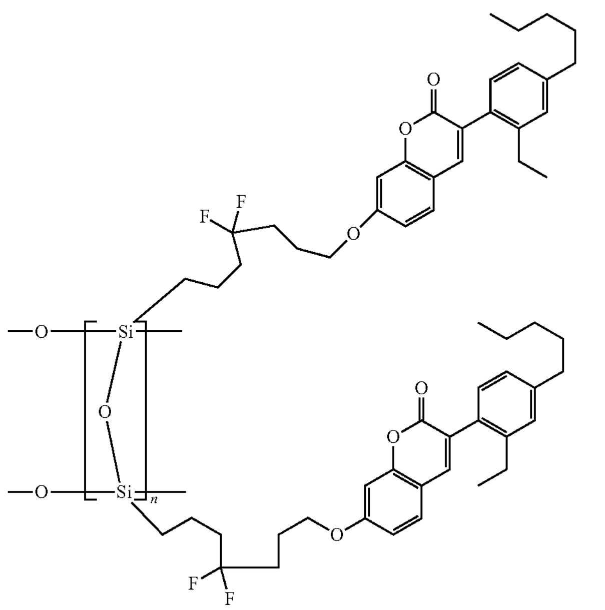
P-092
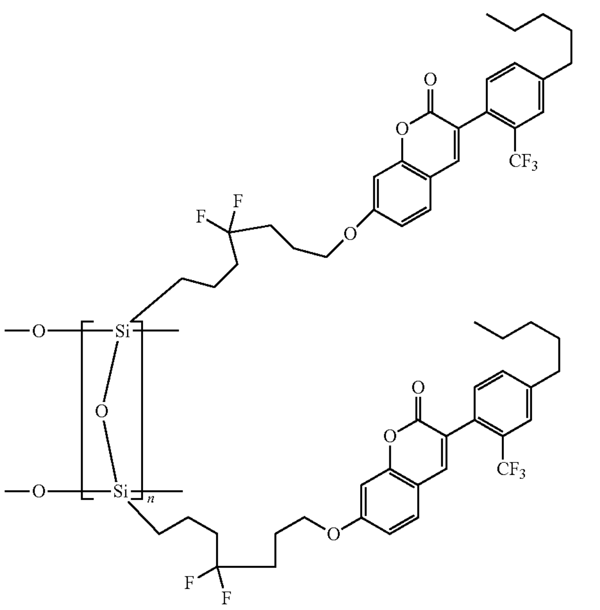

-continued

P-093

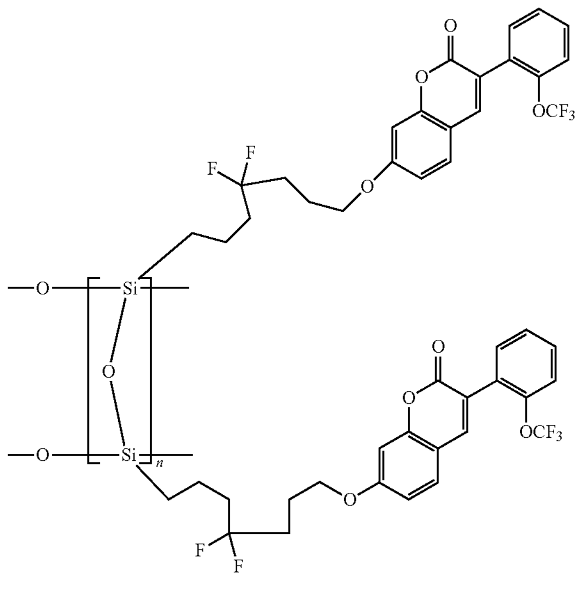

P-094

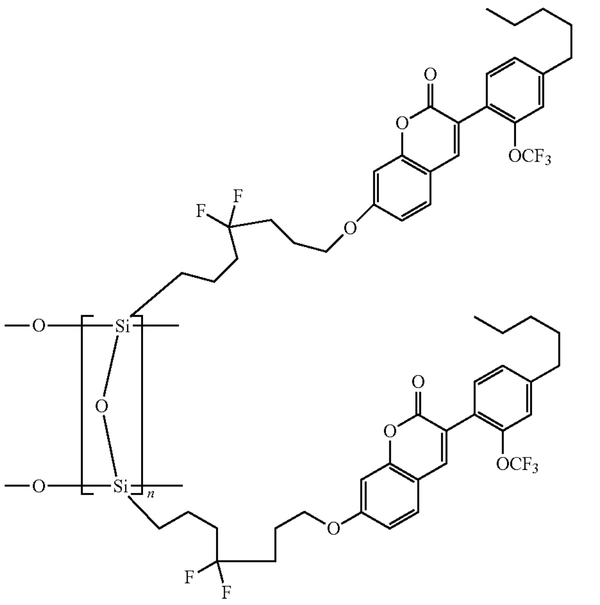

The letter n gives the degree of polymerization as explained before.

Preferably a co-polymer according to the invention as described before or preferably described before comprises the one or more constitutional units $M^0$ in a molar ratio m1 and the one or more constitutional units $M^2$ in a molar ratio m2, wherein the ratio m1:m2 is at least 0.01 and at most 100.

The oligomers or polymers according to the invention as described before or preferably described may be cross-linked depending on the monomer of formula (I) used.

The oligomers and polymers of the present invention may be made by any suitable method. It is, however, preferred that the present oligomers and polymers are made by reaction with sulfuric acid in case of the synthesis of polysiloxanes or by reaction with organo lithium compounds with cyclodisilazanes according to compounds of formula (I) containing polymerizable groups of formulae (5) to (7) in toluene/THF at room temperature for the synthesis of polysilazanes.

The present invention is also directed to a composition comprising at least one compound of formula (I), (I-1), (I-2), (I'), (I'') or (I''') as described or preferably described before and/or an oligomer or polymer as described before or preferably described before.

A composition comprising at least one compound of formula (I), (I-1), (I-2), (I'), (I'') or (I''') as described or preferably described before and an oligomer or polymer as described before is primarily used for the synthesis of block co-polymers with the condition that the oligomer or polymer has at least one reactive group left which may react with the monomers.

Depending upon the intended use such composition may comprise further different components. Such further components may, for example, be selected from the group of UV absorbers.

The compositions may include or comprise, essentially consist of or consist of the said requisite or optional constituents. All compounds or components which can be used in the compositions are either known and commercially available or can by synthesized by known processes.

The UV absorber that may be used in the present composition is not particularly limited and can easily be selected from those generally known to the skilled person. Generally suitable UV absorbers are characterized by being unsaturated compounds, preferably compounds comprising one or more selected from group consisting of olefinic groups, aryl groups and heteroaryl groups; these groups may be present in any combination.

Suitable UV-absorbers for use in the present composition may, for example, be selected from those comprising a group selected from benzotriazole, benzophenone and triazine. Suitable UV-absorbers are, for example, disclosed in U.S. Pat. Nos. 5,290,892; 5,331,073 and 5,693,095.

The compounds of formula (I) according to the invention and their oligomers or polymers as described before or preferably described before are particularly well suited for use in optically active devices.

Hence the present invention is also directed to articles e.g. blanks which may be transformed into optically active devices comprising at least one compound of formula (I) as described before or preferably described before or at least one oligomer or polymer as described before or preferably described before.

Preferred articles are blanks which may be transformed into optically active devices or the optically active devices as such. Preferred optically active devices are ophthalmic devices. Examples of such ophthalmic devices include lenses, keratoprostheses, and cornea inlays or rings. More preferably, said article is a blank which may be transformed into an eye-implant or the eye-implant as such. More preferably, said eye-implant is a lens. Most preferably, such article is a blank which may be transformed into an intraocular lens or the intraocular lens as such, which may, for example, be a posterior chamber intraocular lens or an anterior chamber intraocular lens.

A blank of this invention may be produced as a step in the manufacturing process used to create an intraocular lens. For example, without limitation, a manufacturing process may include the steps of polymer synthesis, polymer sheet casting, blank cutting, optic lathe cutting, optic milling, haptic milling or attachment, polishing, solvent extraction, sterilization and packaging.

The present articles according to the invention as described before or preferably described before may be formed by a process comprising the steps of

- providing a composition comprising at least one compound of formula (I) as described herein or preferably described herein and/or an oligomer or polymer as described herein or preferably described herein; and
- subsequently forming the article of said composition.

Intraocular lenses in accordance with the present invention are believed to show particularly advantageous properties in that they are flexible enough so as to be rolled or folded and consequently requiring a much smaller incision for them to be inserted into the eye. It is believed that this will allow for improved healing of the eye, particularly in respect to the time for the eye to heal.

The type of intraocular lens is not limited in any way. It may, for example, comprise one or more optic and one or more haptic components, wherein the one or more optic components serve as lens and the one or more haptic components are attached to the one or more optic components and hold the one or more optic components in place in the eye. The present intraocular lens may be of a one-piece design or of multi-piece design, depending on whether the one or more optic components and the one or more haptic components are formed from a single piece of material (one-piece design) or are made separately and then combined (multi-piece design). The present intraocular lens is also designed in such a way that it allows to be, for example, rolled up or folded small enough so that it fits through an incision in the eye, said incision being as small as possible, for example, at most 3 mm in length.

Additionally, intraocular lenses in accordance with the present invention allow for the non-invasive adjustment of the optical properties, particularly the refractive power, after implantation of the lens into the eye, thus reducing the need for post-surgery vision aids or reducing or totally avoiding follow-up surgery.

In order to change the optical properties and particularly the refractive power of the intraocular lens it is exposed to irradiation having a wavelength of at least 200 nm and of at most 1500 nm. Hence, the present invention is also directed to a process of changing the optical properties of an article as defined or preferably defined herein, said process comprising the steps of

- providing an article as defined herein; and
- subsequently exposing said article to irradiation having a wavelength of at least 200 nm and at most 1500 nm.

Preferably, said irradiation has a wavelength of at least 250 nm or 300 nm, more preferably of at least 350 nm, even more preferably of at least 400 nm, still even more preferably of at least 450 nm, and most preferably of at least 500 nm. Preferably, said irradiation has a wavelength of at most 1400 nm or 1300 nm or 1200 nm or 1100 nm or 1000 nm, more preferably of at most 950 nm or 900 nm, even more preferably of at most 850 nm, still even more preferably of at most 800 nm and most preferably of at most 750 nm.

EXAMPLES

The following examples are intended to show the advantages of the present compounds in a non-limiting way.

Unless indicated otherwise, all syntheses can be or are carried out under an inert atmosphere using dried (i.e. water-free) solvents. Solvents and reagents are purchased or can be purchased from commercial suppliers.

DCM is used to denote dichloromethane. DMF is used to denote dimethylformamide. EE is used to denote ethyl acetate. THF is used to denote tetrahydrofuran.

Co-polymer-properties can be investigated on blanks, prepared by bulk polymerization of the monomers. Co-monomers, cross-linkers and initiators therefore can be purchased from commercial sources. All chemicals are of highest purity available and can be used as received.

Synthesis of Precursor Materials:

General Remarks & General Synthetic Procedures (GSP 1) for the Synthesis of Acetic Acid 3-phenyl-coumarin-7-yl Ester Derivative:

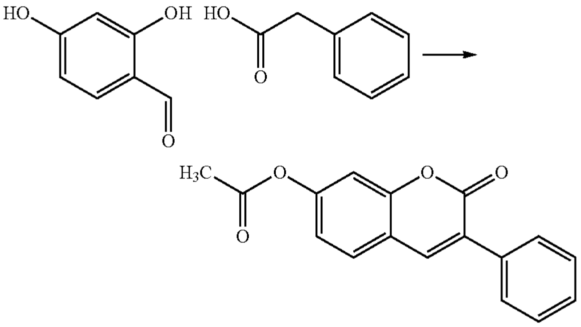

30 g (0.213 mmol) 2,4-Dihydroxy-benzaldehyde and 29.273 g (0213 mmol) phenyl-acetic acid are dissolved in 67.47 ml acetic anhydride and 65.485 ml pyridine. The batch is stirred at 135° C. for 72 h and is then cooled to room temperature. The solid which has precipitated out is filtered off with suction and rinsed neutral with water. The residue is dried at 40° C. in vacuo. The yield of 2-oxo-3-phenyl-2H-chromen-7-yl acetate is 59.7 g (0.18 mmol) (87% of theory).

Analogously, other derivatives are prepared in the same manner: R1 means reactant 1, R2 means reactant 2, [P] means product

| No. | | | Yield [%] |
|---|---|---|---|
| 1a | R1 | 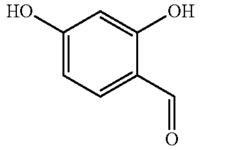 | |
| | R2 | 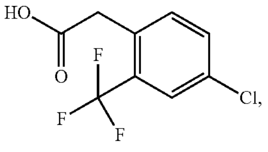<br>CAS: 601513-31-9 | |

-continued
| No. | | | Yield [%] |
|---|---|---|---|
| | [P] | 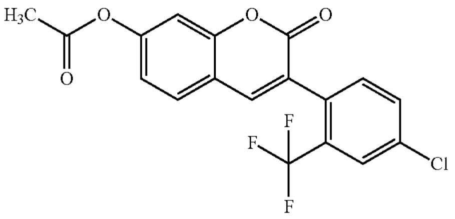 [SMILES: CC(=O)Oc1ccc2cc(-c3ccc(Cl)cc3C(F)(F)F)c(=O)oc2c1] | 57 |
| 1b | R1 | 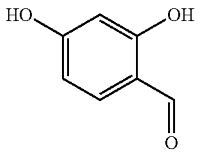 | |
| | R2 | 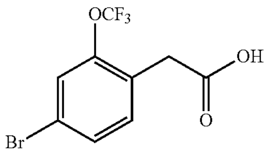 | |
| | [P] | 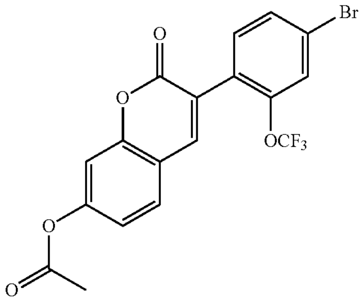 [SMILES: CC(=O)Oc1ccc2cc(-c3ccc(Br)cc3OC(F)(F)F)c(=O)oc2c1] | 69 |
| 1c | R1 | 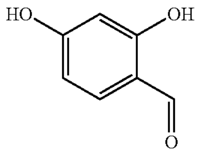 | |
| | R2 | 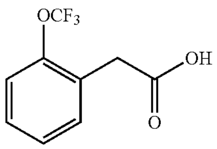 [SMILES: O=C(O)Cc1ccccc1OC(F)(F)F] | |
| | [P] | 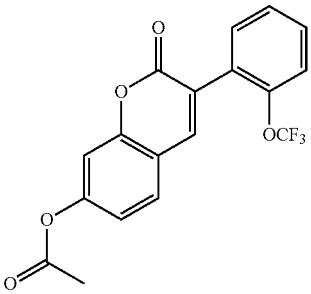 [SMILES: CC(=O)Oc1ccc2cc(-c3ccccc3OC(F)(F)F)c(=O)oc2c1] | 75 |
-continued
| No. | | | Yield [%] |
|---|---|---|---|
| 1d | R1 | 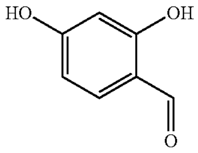 | |
| | R2 | 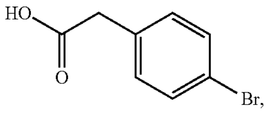 CAS: 1878-68-8 | |
| | [P] | 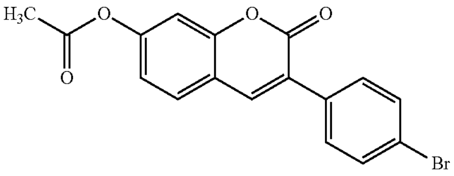 [SMILES: CC(=O)Oc1ccc2cc(-c3ccc(Br)cc3)c(=O)oc2c1] | 96 |
| 1e | R1 | 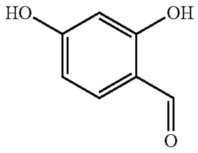 | |
| | R2 | 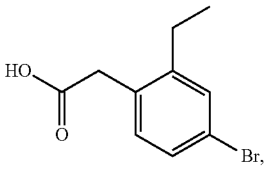 CAS: 855931-72-5 | |
| | [P] | 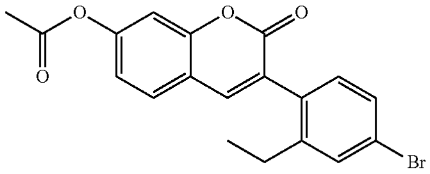 [SMILES: CCc1cc(Br)ccc1-c1cc2ccc(OC(C)=O)cc2oc1=O] | 75 |
| 1f | R1 | 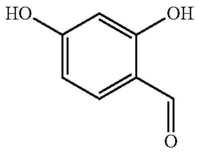 | |
| | R2 | 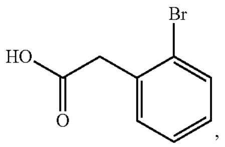 CAS: 18698-97-0 | |

-continued

| No. | | Yield [%] |
|---|---|---|
| [P] | 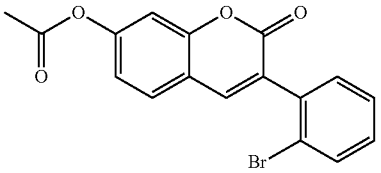 [SMILES: CC(=O)Oc1ccc2cc(-c3ccccc3Br)c(=O)oc2c1] | 61 |

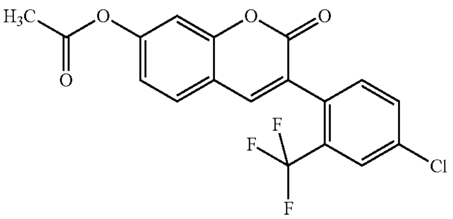 [SMILES: CC(=O)Oc1ccc2cc(-c3ccc(Cl)cc3C(F)(F)F)c(=O)oc2c1]

$^1$H NMR (500 MHz, CDCl3) δ 7.77 (d, 2H, J=2.1 Hz), 7.63 (s, 1H), 7.60 (dd, 1H, J=8.2 Hz, J=2.2 Hz), 7.53 (d, 1H, J=8.4 Hz), 7.36 (d, 1H, J=8.2 Hz), 7.19 (d, 1H, J=2.1 Hz), 7.10 (dd, 1H, J=8.5 Hz, J=2.2 Hz), 2.36 (s, 3H).

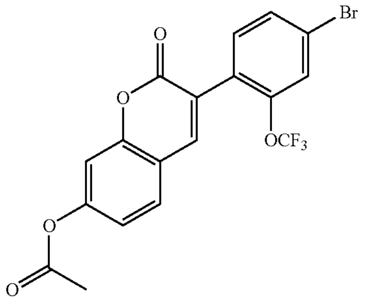 [SMILES: CC(=O)Oc1ccc2cc(-c3ccc(Br)cc3OC(F)(F)F)c(=O)oc2c1]

$^1$H NMR (500 MHz, $CDCl_3$) δ 8.21 (s, 1H), 7.84 (d, 1H, J=8.5 Hz), 7.79-7.72 (m, 2H), 7.58 (d, 1H, J=8.7 Hz), 7.37 (d, 1H, J=2.1 Hz), 7.22 (dd, 1H, J=8.4 Hz, J=2.2 Hz), 2.33 (s, 3H).

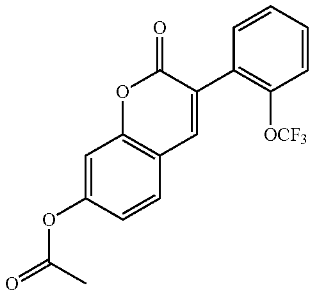 [SMILES: CC(=O)Oc1ccc2cc(-c3ccccc3OC(F)(F)F)c(=O)oc2c1]

$^1$H NMR (500 MHz, $CDCl_3$) δ 7.74 (s, 1H), 7.54 (d, 1H, J=8.5 Hz), 7.51 (dd, 1H, J=7.8 Hz, J=1.7 Hz), 7.49-7.44 (m, 1H), 7.40-7.35 (m, 3H), 7.18 (d, 1H, J=2.1 Hz), 7.38 (d, J=2.1 Hz), 7.09 (dd, J=8.4 Hz, J=2.2 Hz), 2.36 (s, 3H).

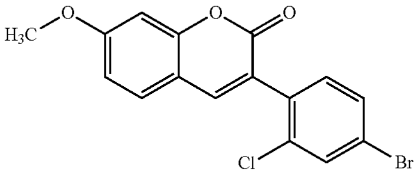 [SMILES: COc1ccc2cc(-c3ccc(Br)cc3Cl)c(=O)oc2c1]

$^1$H NMR (500 MHz, CDCl3) δ 8.31 (m, 2H), 7.47 (dd, 1H, J=8.2 Hz, J=1.8 Hz), 7.43 (d, 1H, J=8.3 Hz), 7.29 (d, 1H, J=8.2 Hz), 6.89 (d, 2H, J=8.4 Hz), 3.90 (s, 3H).

Example 2

General Remarks & General Synthetic Procedures (GSP 2) for the Deprotection of the Acetate Derivative to the Phenol Derivative:

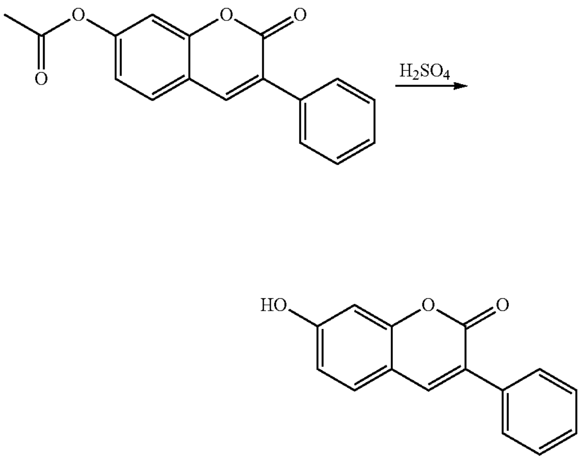

7.0 mmol acetic acid 3-phenyl-coumarin-7-yl ester are suspended in a mixture of 14 ml ethanol and 10 ml sulfuric acid (20%, aq.) and refluxed for 2 h. The batch is then cooled to room temperature, and the precipitated solid is filtered off with suction and rinsed neutral with water. The yield is 6.8 mmol, 97% of theory.

$^1$H NMR (500 MHz, DMSO-d6) δ 10.59 (s, 1H), 8.16 (s, 1H), 7.70 (dd, 2H, J=7.3 Hz, J=1.7 Hz), 7.61 (d, 1H, J=8.5 Hz), 7.45 (t, 2H, J=7.5 Hz), 7.39 (t, 1H, J=7.3 Hz), 6.83 (dd, 1H, J=8.5 Hz, J=2.2 Hz), 6.77 (d, 1H, J=2.2 Hz).

Analogously, other 7-hydroxy-3-phenyl-coumarin derivatives are prepared in the same manner:

| No. | Reactant | Product | Yield [%] |
|---|---|---|---|
| 2a | 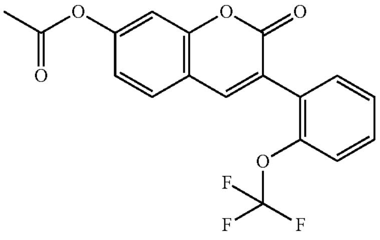 [SMILES: CC(=O)Oc1ccc2cc(-c3ccccc3OC(F)(F)F)c(=O)oc2c1] | 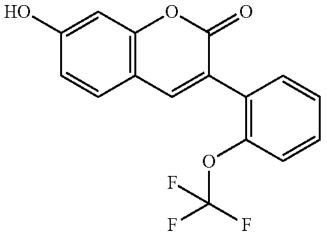 [SMILES: O=c1oc2cc(O)ccc2cc1-c1ccccc1OC(F)(F)F] | 89 |

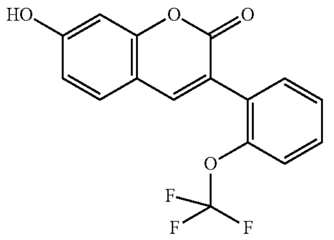 [SMILES: O=c1oc2cc(O)ccc2cc1-c1ccccc1OC(F)(F)F]

$^1$H NMR (500 MHz, DMSO-d6) δ 10.68 (s, 1H), 8.04 (s, 1H), 7.61 (d, J=8.5 Hz, 1H), 7.57 (td, J=7.4 Hz, 1.7 Hz, 1H), 7.49 (dd, J=7.2, 1.3 Hz, 1H), 7.46 (d, J=7.6 Hz, 1H), 6.85 (dd, J=8.5 Hz, 2.3 Hz, 1H), 6.80 (d, J=2.1 Hz, 1H).

Example 3

General Remarks & General Synthetic Procedures (GSP 3) for the Suzuki Coupling of Halogenated 2-oxo-3-phenyl-2H-chromen-7-yl Acetate Derivatives:

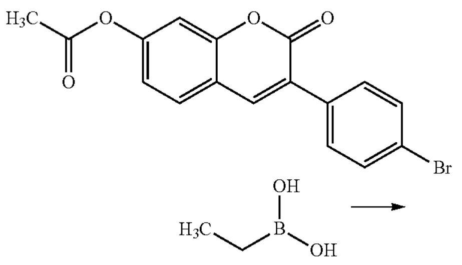

-continued

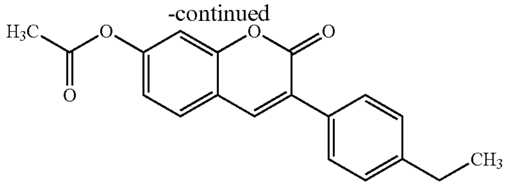

3.0 g (8.4 mmol) of acetic acid 3-(4-bromophenyl)-coumarin-7-yl ester, 0.65 g (8.8 mmol) of ethylboronic acid and 3.7 g (17.5 mmol) of tri-potassium phosphate trihydrate are dissolved in 80 ml of toluene and degassed. 171 mg (0.4 mmol) of 2-dicyclohexylphoshino-2',6'-dimethoxy-1,1'-biphenyl [S-Phos] and 47 mg (0.2 mmol) of palladium(II) acetate are added. The reaction mixture is subsequently stirred at 110° C. for 24 h under a protective-gas atmosphere. The cooled solution is diluted with ethyl acetate and washed with water, dried and evaporated. The product is purified by column chromatography on silica gel (heptane/ethyl acetate). Yield: 2.12 g (6.88 mmol), 82% of theory.

Under the basic conditions, deprotection of the acetate group to the corresponding phenol is observed during several Suzuki coupling reactions. To complete the deprotection step, the crude organic phase after workup is refluxed with a 1:2 mixture sulfuric acid (~20%):ethanol until completion. Then column chromatography of the obtained residue, as described above, is done.

$^1$H NMR (500 MHz, DMSO-d6) δ 8.23 (s, 1H), 7.81 (d, 1H, J=8.4 Hz), 7.64 (d, 2H, J=8.2 Hz), 7.34-7.25 (m, 3H), 7.18 (dd, 1H, J=8.4 Hz, J=2.2 Hz), 7.20 (dd, 1H, J=8.4 Hz, J=2.1 Hz), 2.62 (t, 2H, J=7.6 Hz), 2.32 (s, 3H), 2.72 (q, 2H), 1.18 (t, 3H, J=7.2 Hz).

Analogously, other Suzuki derivatives are prepared in the same manner: R1 means reactant 1, R2 means reactant 2, [P] means product

| No. | | | Yield [%] |
|---|---|---|---|
| 3a | R1 | 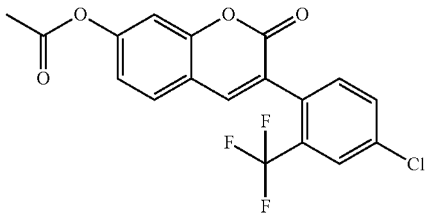 [SMILES: CC(=O)Oc1ccc2cc(-c3ccc(Cl)cc3C(F)(F)F)c(=O)oc2c1] | |
| | R2 | 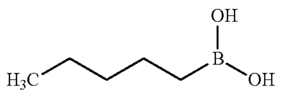 | |

-continued
| No. | | | Yield [%] |
|---|---|---|---|
| | [P] | 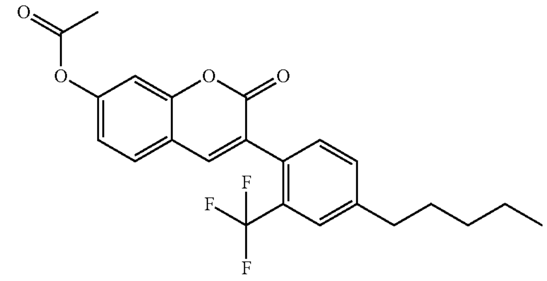 [SMILES: CCCCCc1ccc(-c2cc3ccc(OC(C)=O)cc3oc2=O)c(C(F)(F)F)c1] | 94 |
| 3b | R1 | 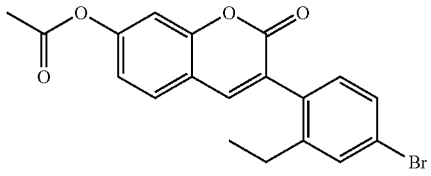 [SMILES: CCc1cc(Br)ccc1-c1cc2ccc(OC(C)=O)cc2oc1=O] | |
| | R2 | 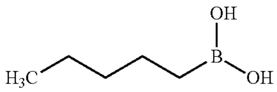 | |
| | [P] | 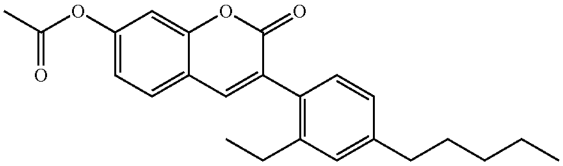 [SMILES: CCCCCc1ccc(-c2cc3ccc(OC(C)=O)cc3oc2=O)c(CC)c1] | 88 |
| 3c | R1 | 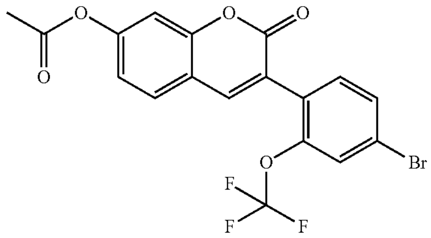 [SMILES: CC(=O)Oc1ccc2cc(-c3ccc(Br)cc3OC(F)(F)F)c(=O)oc2c1] | |
| | R2 | 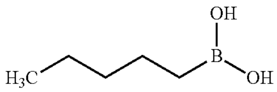 | |
| | [P] | 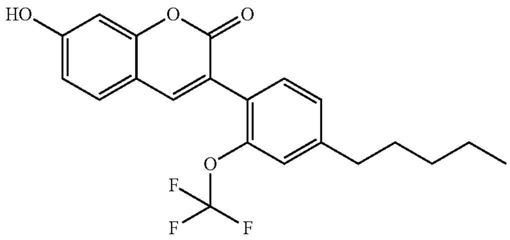 [SMILES: CCCCCc1ccc(-c2cc3ccc(O)cc3oc2=O)c(OC(F)(F)F)c1] | 90 |
| 3d | R1 | 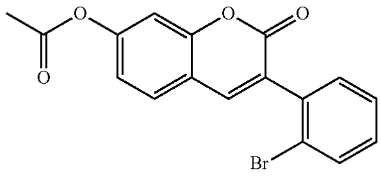 [SMILES: CC(=O)Oc1ccc2cc(-c3ccccc3Br)c(=O)oc2c1] | |

-continued

| No. | | Yield [%] |
|---|---|---|
| R2 | 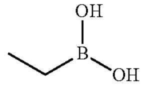 | |
| [P] | 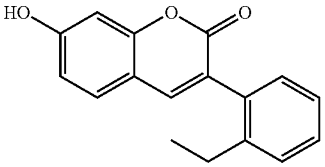 [SMILES: CCc1ccccc1-c1cc2ccc(O)cc2oc1=O] | 56 |

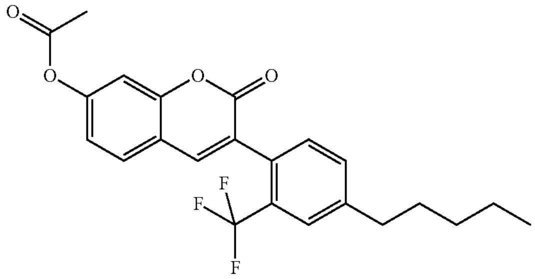 [SMILES: CCCCCc1ccc(-c2cc3ccc(OC(C)=O)cc3oc2=O)c(C(F)(F)F)c1]

$^1$H NMR (500 MHz, CDCl3) δ 7.62 (s, 1H), 7.57 (d, 1H, J=1.7 Hz), 7.51 (d, 1H, J=8.5 Hz), 7.44-7.38 (m, 1H), 7.30 (d, 1H, J=7.8 Hz), 7.17 (d, 1H, J=2.2 Hz), 7.08 (dd, 1H, J=8.4 Hz, J=2.2 Hz), 2.70 (t, 2H, J=8.7 Hz), 2.36 (s, 3H), 1.71-1.62 (m, 2H), 1.38-1.35 (m, 4H), 0.92 (m, 3H).

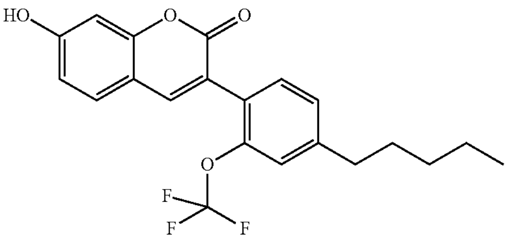 [SMILES: CCCCCc1ccc(-c2cc3ccc(O)cc3oc2=O)c(OC(F)(F)F)c1]

$^1$H NMR (500 MHz, CDCl3) δ 7.69 (d, 1H, J=9.9 Hz), 7.40 (d, 2H, J=8.0 Hz), 7.18-7.15 (m, 2H), 6.96 (d, 1H, J=2.2 Hz), 6.83 (dd, 1H, J=8.5 Hz, J=2.3 Hz), 5.98 (d, 1H, J=9.2 Hz), 2.71-2.61 (m, 2H), 1.69-1.60 (m, 2H), 1.37-1.34 (m, 4H), 0.91 (t, 3H, J=6.9 Hz).

Example 4

General Remarks & General Synthetic Procedures (GSP 4) for the Reaction of the Corresponding (Fluorinated) Monoalcohol with 7-hydroxy-3-phenyl-2H-chromen-2-one Derivatives (Mitsunobu Alkylation Type Reaction):

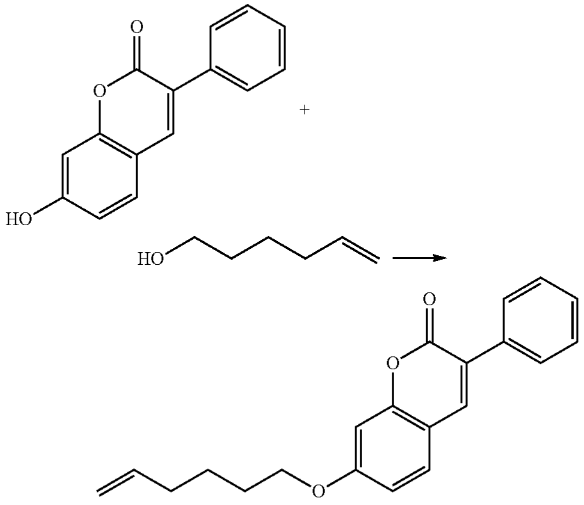

To an ice-cooled solution of 7-hydroxy-3-phenyl-2H-chromen-2-one (9.02 g, 36.94 mmol), 5-hexen-1-ol (4.24 ml, 36.94 mmol, 1.0 equiv.), and triphenylphosphine (9.787 g, 1.00 equiv.) in 100 ml THF, diisopropyl azodicarboxylate (7.42 ml, 1.00 equiv.) is added dropwise. After stirring at room temperature overnight, the reaction mixture is evaporated. The crude product is purified by column chromatography (cyclohexane/DCM). 9.045 g (28.23 mmol, 76% of theory) of 7-Hex-5-enyloxy-3-phenyl-2H-chromen-2-on is isolated.

Analogously, other derivatives are prepared in the same manner: R1 means reactant 1, R2 means reactant 2, [P] means product

| No. | | | Yield [%] |
|---|---|---|---|
| 4a | R1 | 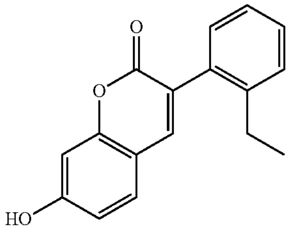 [SMILES: CCc1ccccc1-c1cc2ccc(O)cc2oc1=O] | |

-continued
| No. | | | Yield [%] |
|---|---|---|---|
| | R2 | 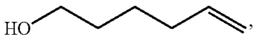, CAS: 821-41-0 | |
| | [P] | 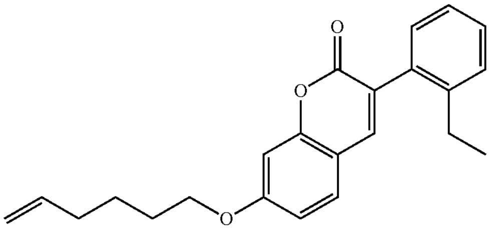 [SMILES: C=CCCCCOc1ccc2cc(-c3ccccc3CC)c(=O)oc2c1] | 58 |
| 4b | R1 | 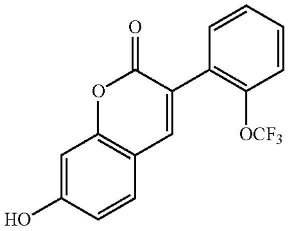 [SMILES: O=c1oc2cc(O)ccc2cc1-c1ccccc1OC(F)(F)F] | |
| | R2 | 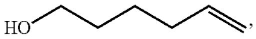, CAS: 821-41-0 | |
| | [P] | 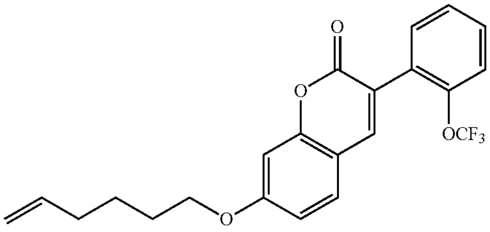 [SMILES: C=CCCCCOc1ccc2cc(-c3ccccc3OC(F)(F)F)c(=O)oc2c1] | 61 |
| 4c | R1 | 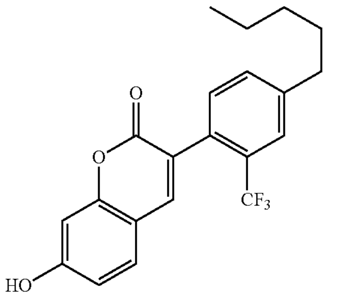 [SMILES: CCCCCc1ccc(-c2cc3ccc(O)cc3oc2=O)c(C(F)(F)F)c1] | |
| | R2 | 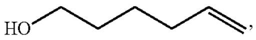, CAS: 821-41-0 | |
| | [P] | 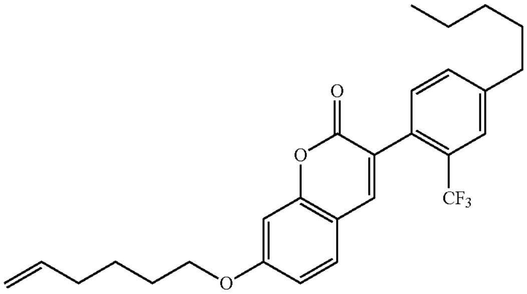 [SMILES: C=CCCCCOc1ccc2cc(-c3ccc(CCCCC)cc3C(F)(F)F)c(=O)oc2c1] | 81 |

-continued
| No. | | | Yield [%] |
|---|---|---|---|
| 4d | R1 | 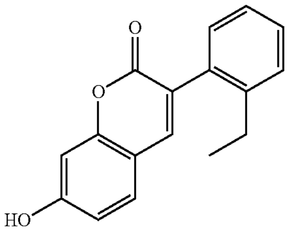 [SMILES: CCc1ccccc1-c1cc2ccc(O)cc2oc1=O] | |
| | R2 | 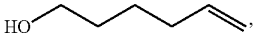, CAS: 821-41-0 | |
| | [P] | 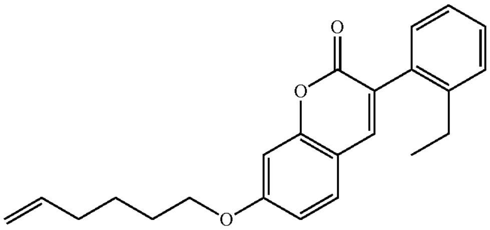 [SMILES: C=CCCCCOc1ccc2cc(-c3ccccc3CC)c(=O)oc2c1] | 69 |
| 4e | R1 | 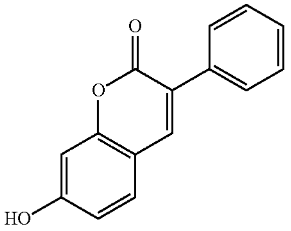 [SMILES: O=c1oc2cc(O)ccc2cc1-c1ccccc1] | |
| | R2 | 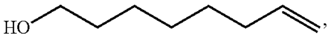, CAS: 13175-44-5 | |
| | [P] | 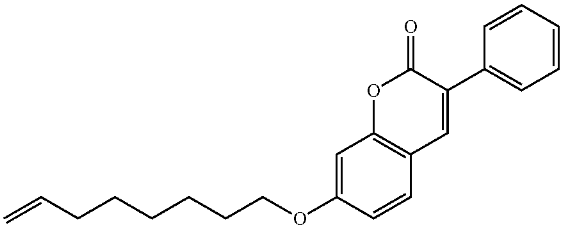 [SMILES: C=CCCCCCCOc1ccc2cc(-c3ccccc3)c(=O)oc2c1] | 63 |
| 4f | R1 | 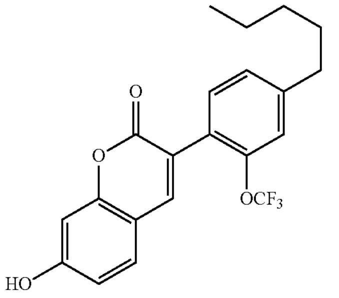 [SMILES: CCCCCc1ccc(-c2cc3ccc(O)cc3oc2=O)c(OC(F)(F)F)c1] | |
| | R2 | 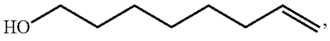, CAS: 13175-44-5 | |

-continued
| No. | | | Yield [%] |
|---|---|---|---|
| | [P] | 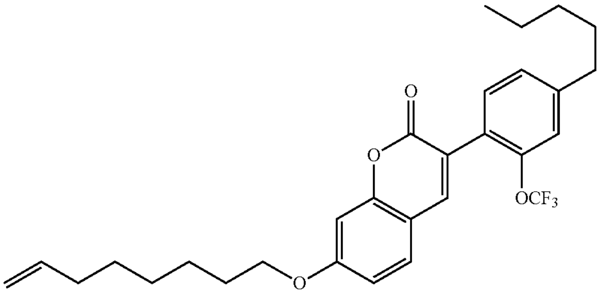 [SMILES: C=CCCCCCCOc1ccc2cc(-c3ccc(CCCCC)cc3OC(F)(F)F)c(=O)oc2c1] | 45 |
| 4g | R1 | 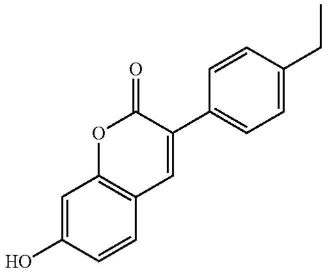 [SMILES: CCc1ccc(-c2cc3ccc(O)cc3oc2=O)cc1] | |
| | R2 | 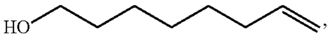, CAS: 13175-44-5 | |
| | [P] | 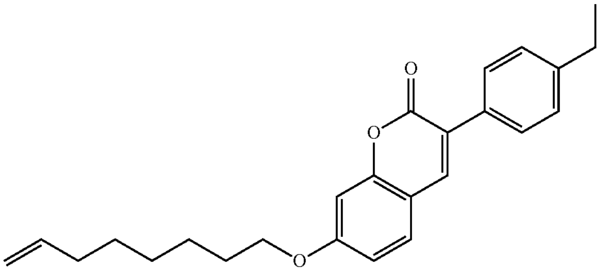 [SMILES: C=CCCCCCCOc1ccc2cc(-c3ccc(CC)cc3)c(=O)oc2c1] | 60 |
| 4h | R1 | 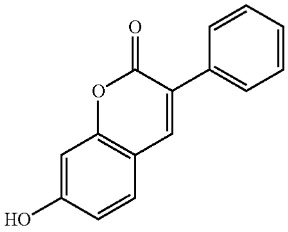 [SMILES: O=c1oc2cc(O)ccc2cc1-c1ccccc1] | |
| | R2 | 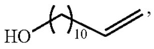, CAS: 35289-31-7 | |
| | [P] | 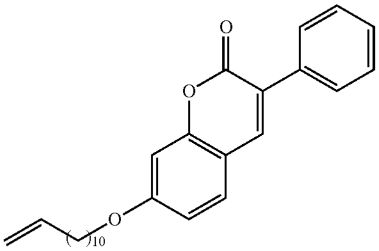 | 49 |

-continued
| No. | | | Yield [%] |
|---|---|---|---|
| 4i | R1 | 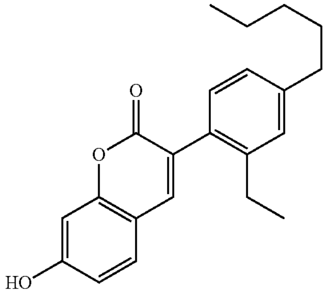 [SMILES: CCCCCc1ccc(-c2cc3ccc(O)cc3oc2=O)c(CC)c1] | |
| | R2 | 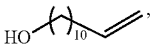, CAS: 35289-31-7 | |
| | [P] | 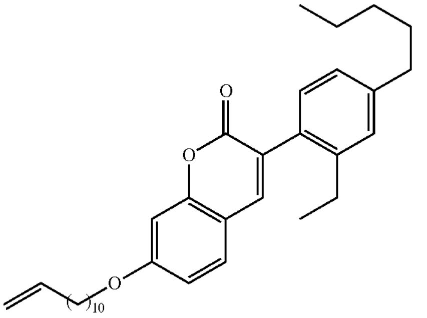 | 43 |
| 4j | R1 | 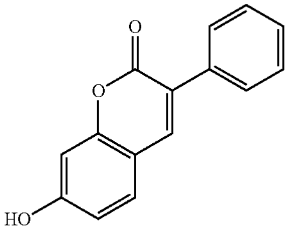 [SMILES: O=c1oc2cc(O)ccc2cc1-c1ccccc1] | |
| | R2 | 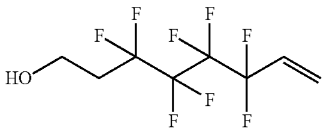 [SMILES: C=CC(F)(F)C(F)(F)C(F)(F)C(F)(F)CCO] | |
| | [P] | 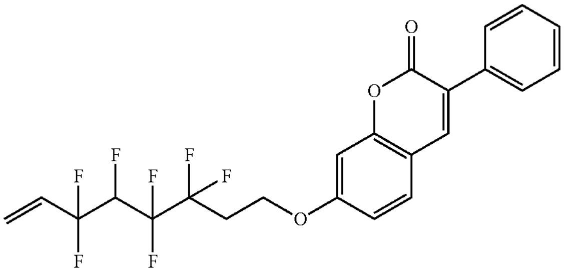 [SMILES: C=CC(F)(F)C(F)C(F)(F)C(F)(F)CCOc1ccc2cc(-c3ccccc3)c(=O)oc2c1] | 39 |
| 4k | R1 | 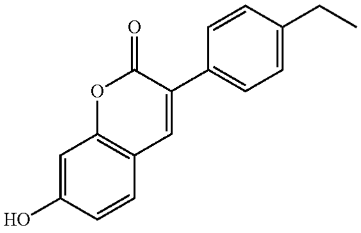 [SMILES: CCc1ccc(-c2cc3ccc(O)cc3oc2=O)cc1] | |

-continued

| No. | | Yield [%] |
| --- | --- | --- |
| R2 | 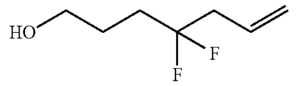 | |
| [P] | 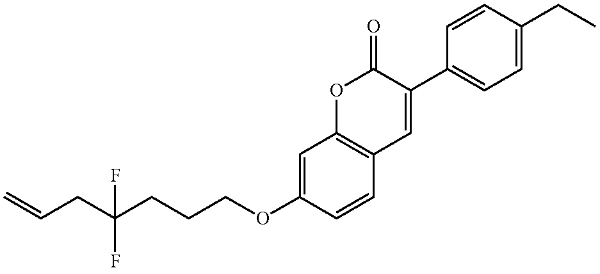 [SMILES: C=CCC(F)(F)CCCOc1ccc2cc(-c3ccc(CC)cc3)c(=O)oc2c1] | 32 |

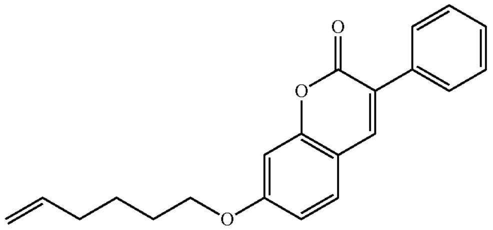 [SMILES: C=CCCCCOc1ccc2cc(-c3ccccc3)c(=O)oc2c1]

$^1$H NMR (500 MHz, $CDCl_3$) δ 7.76 (s, 1H), 7.72-7.66 (m, 2H), 7.46-7.40 (m, 3H), 7.40-7.35 (m, 1H), 6.90-6.81 (m, 2H), 5.84 (ddt, 1H, J=16.9 Hz, J=10.2 Hz, J=6.7 Hz), 5.06 (dd, 1H, J=17.2 Hz, J=1.8 Hz), 5.02-4.97 (m, 1H), 4.04 (t, 2H, J=6.5 Hz), 2.15 (q, 2H, J=7.2 Hz), 1.89-1.81 (m, 2H), 1.64-1.55 (m, 2H).

7-(hex-5-en-1-yloxy)-3-(4-pentyl-2-(trifluoromethyl) phenyl)-2H-chromen-2-one

1H NMR (500 MHz, DMSO-$d_6$) δ 7.96 (s, 1H), 7.68-7.64 (m, 2H), 7.58 (d, J=8.0 Hz, 1H), 7.44 (d, J=7.9 Hz, 1H), 7.07 (d, J=2.3 Hz, 1H), 7.00 (dd, J=8.6, 2.4 Hz, 1H), 5.85 (ddt, J=16.9, 10.2, 6.6 Hz, 1H), 5.09-4.96 (m, 2H), 4.12 (t, J=6.5 Hz, 2H), 2.76-2.70 (m, 2H), 2.12 (q, J=7.2 Hz, 2H), 1.81-1.74 (m, 2H), 1.64 (p, J=7.5 Hz, 2H), 1.54 (p, J=7.6 Hz, 2H), 1.37-1.28 (m, 4H), 0.89 (t, J=7.0 Hz, 3H).

Example 5

General Remarks & General Synthetic Procedures (GSP 5) for the Hydrosilylation of the Corresponding Alkene with the Karstedt Catalyst:

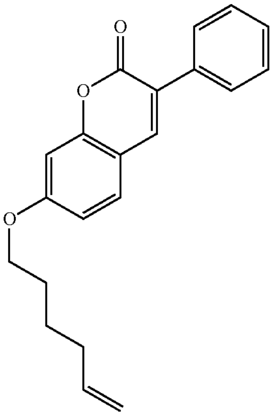

+

-continued

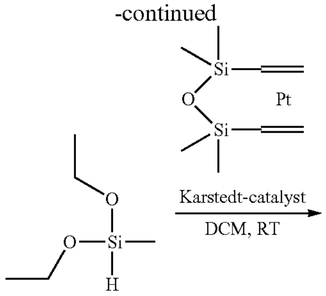

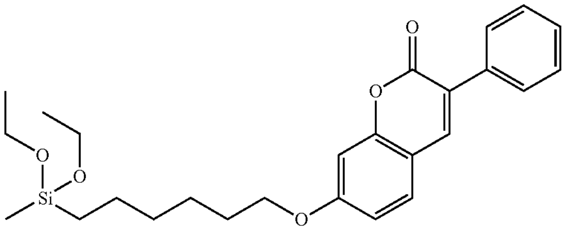

7-Hex-5-enyloxy-3-phenyl-2H-chromen-2-one (1.09 g, 3.4 mmol) is dissolved in 10 ml dry DCM. The solution is saturated with an syringe in the DCM solution. Then 167 μl (16.7 μmol, 0.005 equiv.) of a solution of platinum-divinyltetramethyldisiloxane complex (0.1 mol/l, in poly(dimethylsiloxane) vinyl terminated) is added. Finally, methyldiethoxysilane (1.7 ml, 10.21 mmol, 3.0 equivs.) is added. The solution is stirred at room temperature until completion of the starting material, observed by TLC analysis. The crude reaction mixture is concentrated in vacuo and purified via column chromatography using cyclohexane/ethyl acetate as eluent. 0.815 g of 7-[6-(Diethoxy-methyl-silanyl)-hexyloxy]-3-phenyl-2H-chromen-2-on is isolated (53% of theory).

Analogously, other derivatives are prepared in the same manner: R1 means reactant 1, R2 means reactant 2, [P] means product
| No. | | | Yield [%] |
|---|---|---|---|
| 5a | R1 | 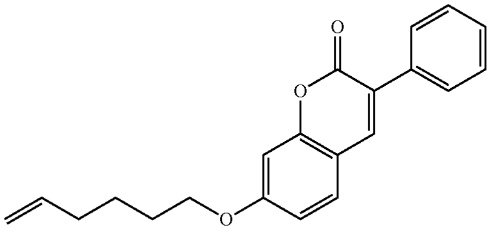 [SMILES: C=CCCCCOc1ccc2cc(-c3ccccc3)c(=O)oc2c1] | |
| | R2 | 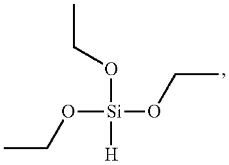, CAS: 998-30-1 | |
| | [P] | 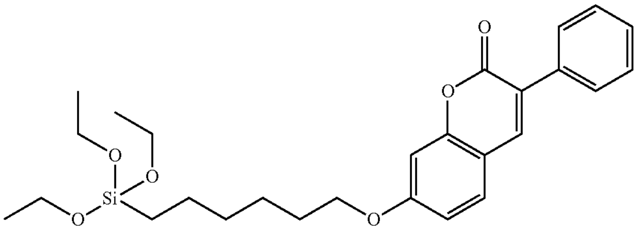 [SMILES: CCO[Si](CCCCCCOc1ccc2cc(-c3ccccc3)c(=O)oc2c1)(OCC)OCC] | 30 |
| 5b | R1 | 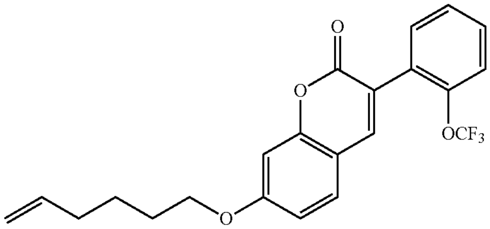 [SMILES: C=CCCCCOc1ccc2cc(-c3ccccc3OC(F)(F)F)c(=O)oc2c1] | |
| | R2 | 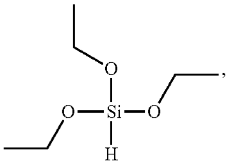, CAS: 998-30-1 | |
| | [P] | 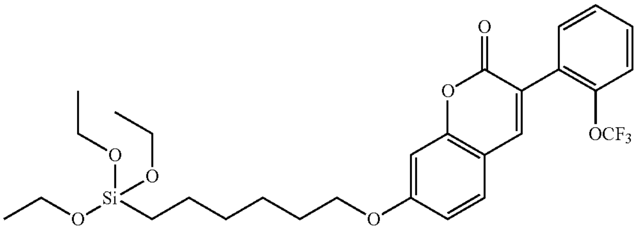 [SMILES: CCO[Si](CCCCCCOc1ccc2cc(-c3ccccc3OC(F)(F)F)c(=O)oc2c1)(OCC)OCC] | 38 |

-continued
| No. | | | Yield [%] |
|---|---|---|---|
| 5c | R1 | 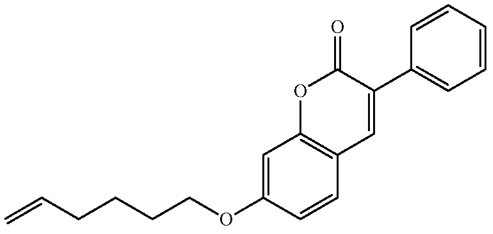 [SMILES: C=CCCCCOc1ccc2cc(-c3ccccc3)c(=O)oc2c1] | |
| | R2 | 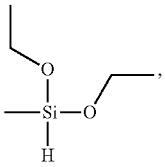, CAS: 2031-62-1 | |
| | [P] | 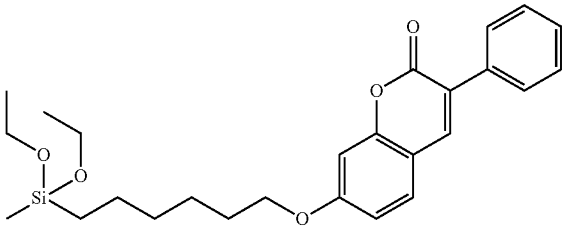 [SMILES: CCO[Si](C)(CCCCCCOc1ccc2cc(-c3ccccc3)c(=O)oc2c1)OCC] | 42 |
| 5d | R1 | 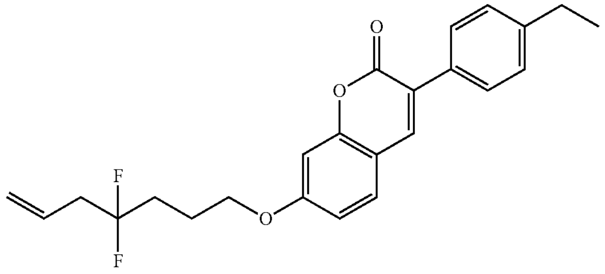 [SMILES: C=CCC(F)(F)CCCOc1ccc2cc(-c3ccc(CC)cc3)c(=O)oc2c1] | |
| | R2 | 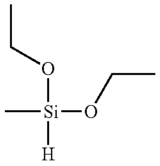 | |
| | [P] | 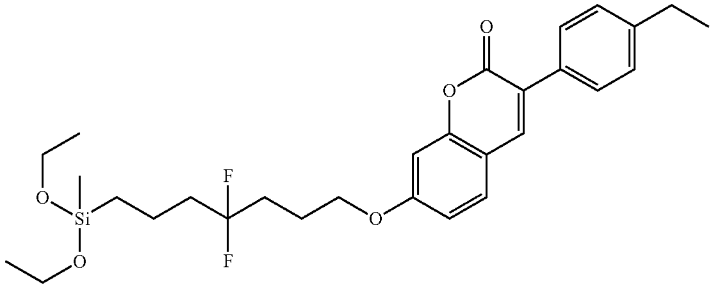 [SMILES: CCO[Si](C)(CCCC(F)(F)CCCOc1ccc2cc(-c3ccc(CC)cc3)c(=O)oc2c1)OCC] | 28 |

-continued
| No. | | | Yield [%] |
|---|---|---|---|
| 5e | R1 | 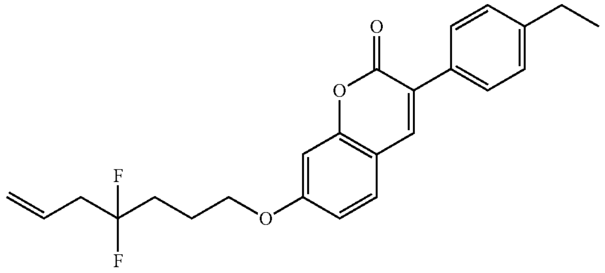 [SMILES: C=CCC(F)(F)CCCOc1ccc2cc(-c3ccc(CC)cc3)c(=O)oc2c1] | |
| | R2 | 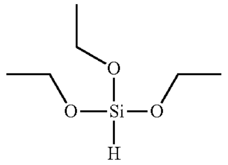 | |
| | [P] | 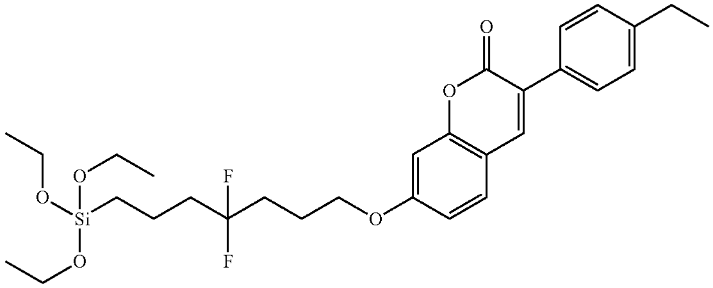 [SMILES: CCO[Si](CCCC(F)(F)CCCOc1ccc2cc(-c3ccc(CC)cc3)c(=O)oc2c1)(OCC)OCC] | 33 |
| 5f | R1 | 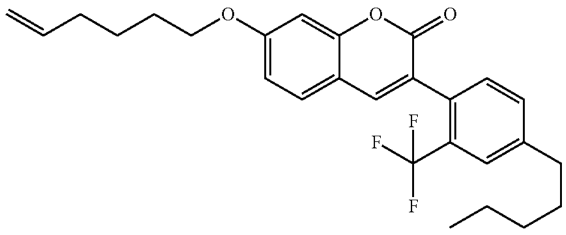 [SMILES: C=CCCCCOc1ccc2cc(-c3ccc(CCCCC)cc3C(F)(F)F)c(=O)oc2c1] | |
| | R2 | 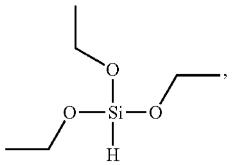, CAS: 998-30-1 | |
| | [P] | 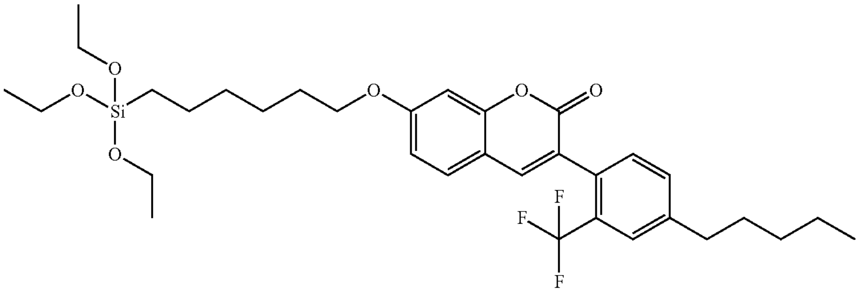 [SMILES: CCCCCc1ccc(-c2cc3ccc(OCCCCCC[Si](OCC)(OCC)OCC)cc3oc2=O)c(C(F)(F)F)c1] | 51 |

-continued

| No. | | | Yield [%] |
|---|---|---|---|
| 5g | R1 | 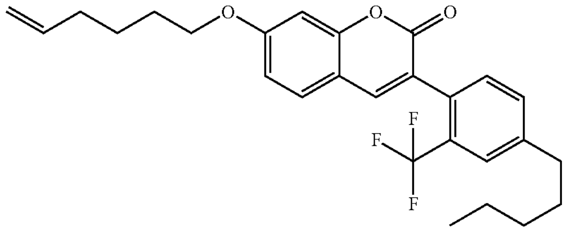 [SMILES: C=CCCCCOc1ccc2cc(-c3ccc(CCCCC)cc3C(F)(F)F)c(=O)oc2c1] | |
| | R2 | 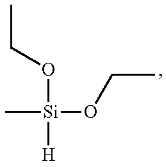, CAS: 2031-62-1 | |
| | [P] | 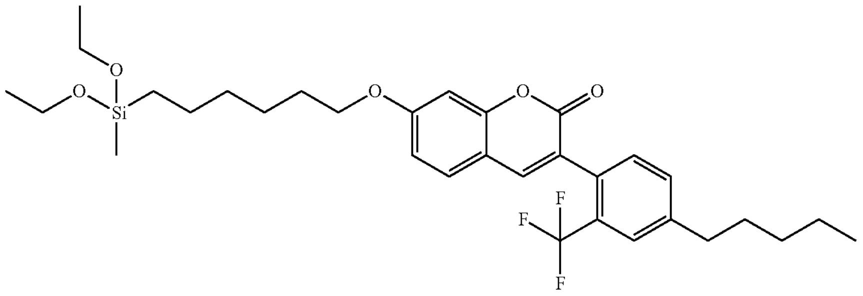 [SMILES: CCCCCc1ccc(-c2cc3ccc(OCCCCCC[Si](C)(OCC)OCC)cc3oc2=O)c(C(F)(F)F)c1] | 27 |

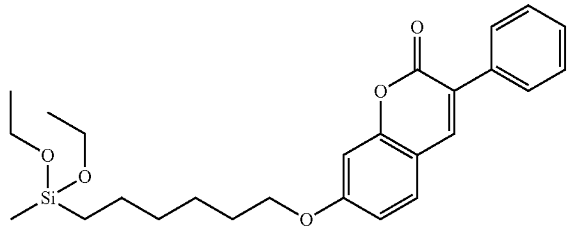 [SMILES: CCO[Si](C)(CCCCCCOc1ccc2cc(-c3ccccc3)c(=O)oc2c1)OCC]

$^1$H NMR (500 MHz, acetone-$d_6$) δ 8.07 (s, 1H), 7.81-7.71 (m, 2H), 7.66 (d, 1H, J=8.5 Hz), 7.48-7.41 (m, 2H), 7.41-7.35 (m, 1H), 7.00-6.91 (m, 2H), 4.16 (t, 2H, J=6.5 Hz), 3.75 (q, 3H, J=7.0 Hz), 1.84 (p, 2H, J=6.6 Hz), 1.54-1.42 (m, 6H), 1.17 (t, 6H, J=7.0 Hz), 0.62 (t, 2H, J=7.9 Hz), 0.06 (s, 3H).

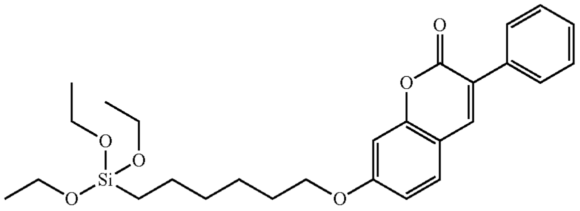 [SMILES: CCO[Si](CCCCCCOc1ccc2cc(-c3ccccc3)c(=O)oc2c1)(OCC)OCC]

$^1$H NMR (500 MHz, acetone-$d_6$) δ δ 8.07 (s, 1H), 7.81-7.70 (m, 2H), 7.66 (d, 1H, J=8.6 Hz), 7.44 (t, 2H, J=7.3 Hz), 7.38 (t, 1H, J=7.3 Hz), 6.96 (dd, 1H, J=8.5 Hz, J=2.4 Hz), 6.93 (d, 2H, J=2.2 Hz), 4.16 (t, 2H, J=6.4 Hz), 3.84-3.75 (m, 6H), 1.83 (dt, 2H, J=8.8 Hz, J=6.4 Hz), 1.54-1.45 (m, 6H), 1.23-1.12 (m, 8H), 0.64-0.61 (m, 2H).

7-((6-(diethoxy(methyl)silyl)hexyl)oxy)-3-(4-pentyl-2-(trifluoromethyl)phenyl)-2H-chromen-2-one 1H NMR (500 MHz, Chloroform-d) δ 7.56 (d, J=5.1 Hz, 2H), 7.39 (dd, J=12.1, 8.9 Hz, 2H), 7.31 (d, J=7.8 Hz, 1H), 6.86 (d, J=7.3 Hz, 2H), 4.03 (t, J=6.5 Hz, 2H), 3.77 (q, J=7.0 Hz, 4H), 2.72-2.67 (m, 2H), 1.82 (p, J=6.6 Hz, 2H), 1.66 (p, J=7.5 Hz, 2H), 1.52-1.45 (m, 2H), 1.45-1.40 (m, 4H), 1.40-1.33 (m, 4H), 1.22 (t, J=7.0 Hz, 6H), 0.96-0.88 (m, 3H), 0.64 (t, J. 7.9 Hz, 2H), 0.12 (s, 3H).

3-(4-pentyl-2-(trifluoromethyl)phenyl)-7-((6-(triethoxysilyl)hexyl)oxy)-2H-chromen-2-one 1H NMR (500 MHz, $CDCl_3$) δ 7.56 (d, J=5.2 Hz, 2H), 7.39 (dd, J=11.9, 8.6 Hz, 2H), 7.31 (d, J=7.8 Hz, 1H), 6.86 (d, J=7.3 Hz, 2H), 4.03 (t, J=6.5 Hz, 2H), 3.82 (q, J=7.0 Hz, 6H), 2.71-2.65 (m, 2H), 1.82 (p, J=6.8 Hz, 2H), 1.66 (p, J=7.5 Hz, 2H), 1.51-1.40 (m, 6H), 1.39-1.31 (m, 4H), 1.23 (t, J=6.9 Hz, 9H), 0.92 (t, J=6.9 Hz, 3H), 0.69-0.62 (m, 2H).

Example 6

General Remarks & General Synthetic Procedures (GSP 6) for the Solvent Polymerization of the Monomers:

To 7-((6-(diethoxy(methyl)silyl)hexyl)oxy)-3-phenyl-2H-chromen-2-one (0.15 g, 0.33 mmol, 1.0 equiv.) concentrated sulfuric aceid (1 μl, cat.) is added. The reaction mixture is stirred for 72 h at 60° C. The product is precipitated in methanol and is finally dried in vacuo at 60° C. for at minimum 5 days.

Examples of polymers within this invention are given in the following table:
| Monomer |
| --- |
| 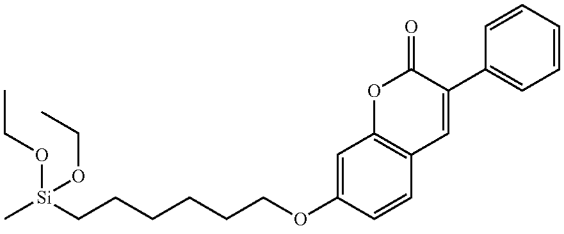<br>(Si-001) |
| 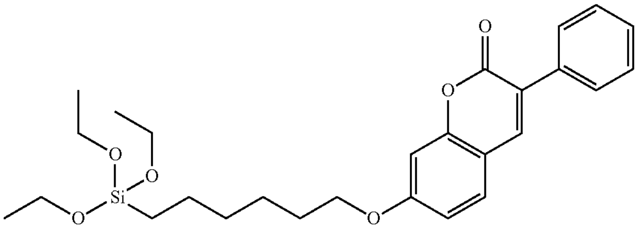<br>(Si-053) |
| 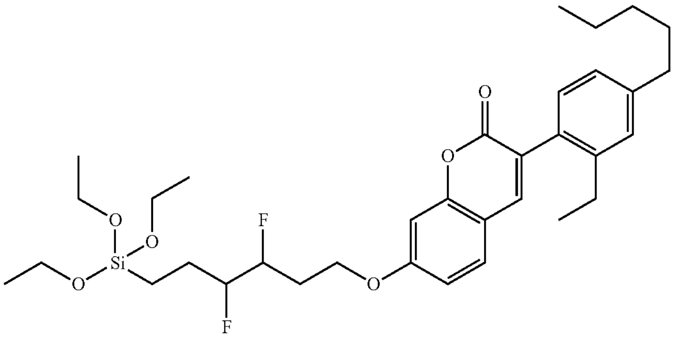<br>(Si-084) |
| 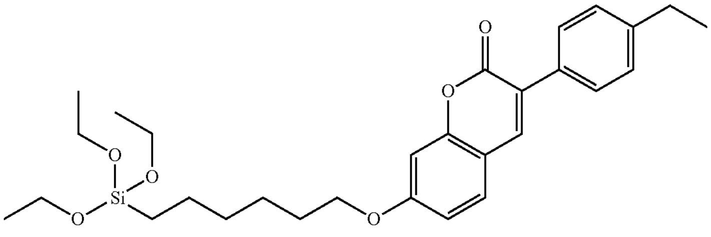<br>(Si-054) |

-continued
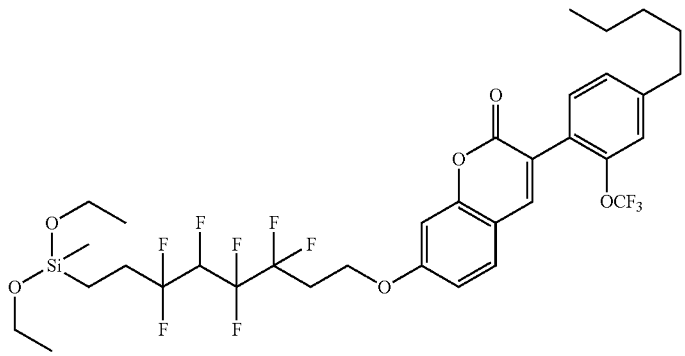
(Si-034)
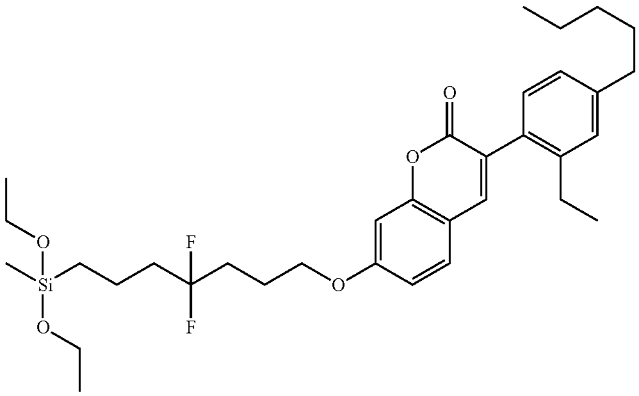
(Si-048)
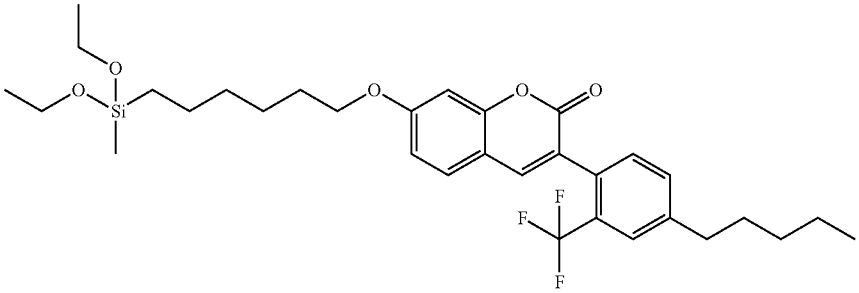
(Si-005)
Polymer
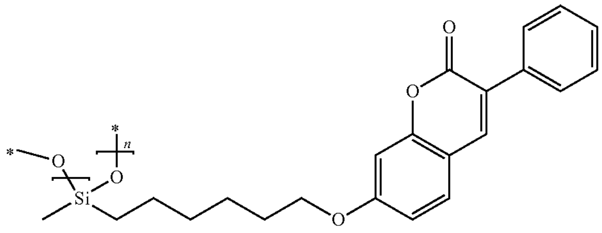
(P-001)

-continued
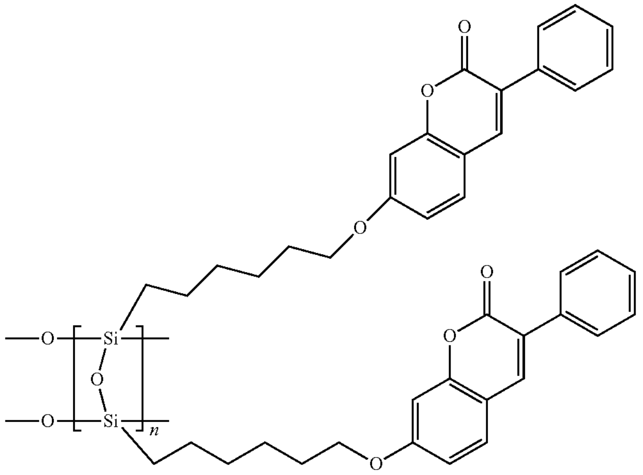
(P-053)
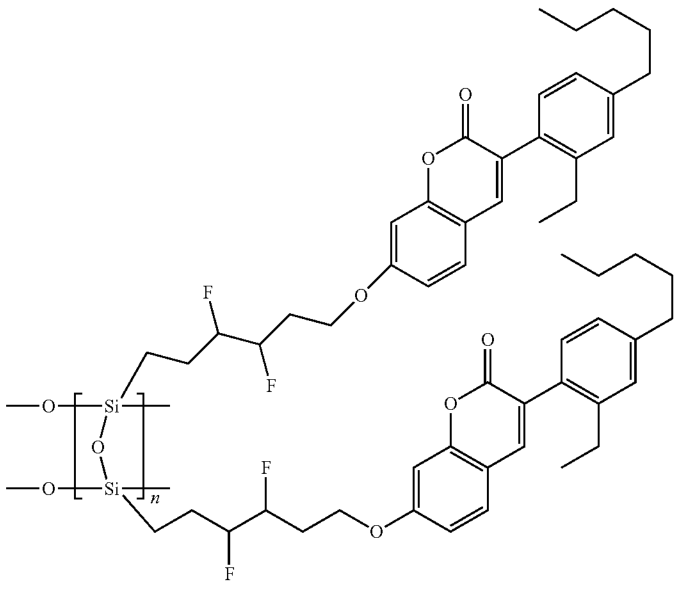
(P-084)

-continued
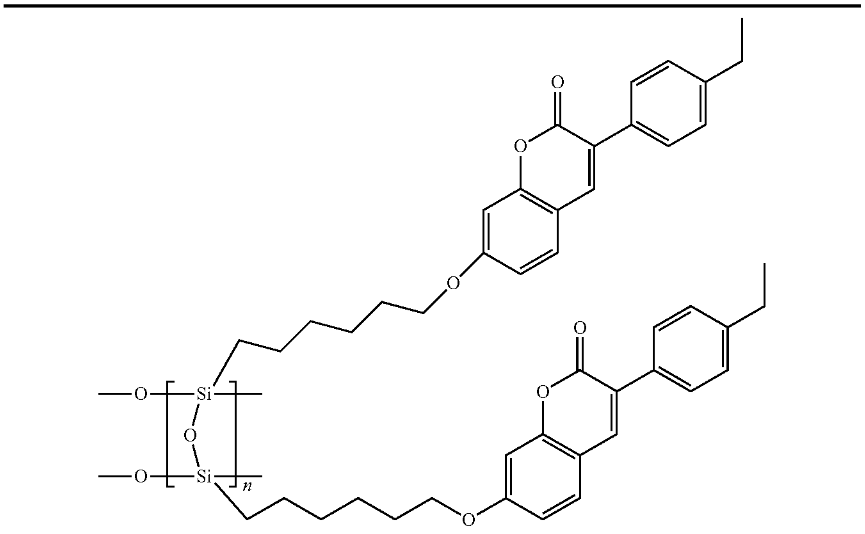
(P-055)
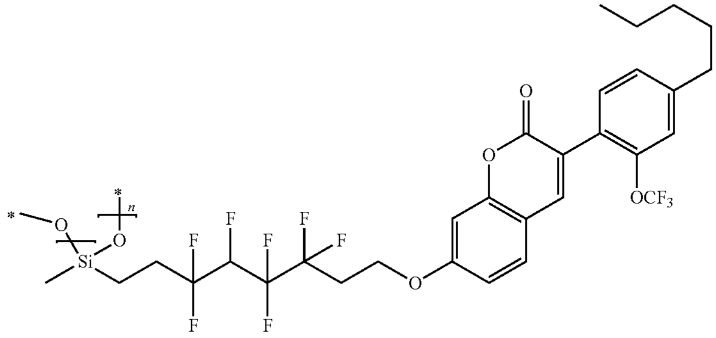
(P-034)
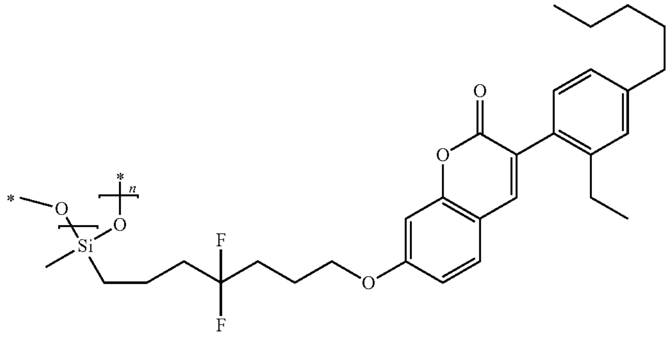
(P-048)
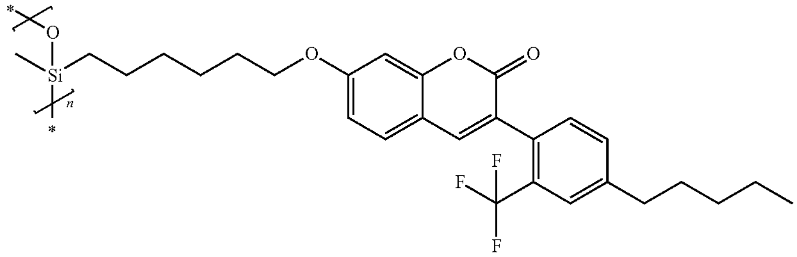
(P-005)

Examples Directed to the Properties of the Compounds

Example 7—Photoinduced Refractive Index Change and Glass Transition Temperature The phase transition temperatures are determined with a TA Instruments Q2000 differential scanning calorimeter during heating in the second heating run with 20 K/min from −100° C. to 200° C. in a hermetic aluminium pans.

Irradiations of the blanks are performed with a Coherent Avia 355-7000 UV-Laser.

Common photoactive polymers that undergo refractive index change upon irradiation with UV-light exhibit glass transition temperatures as low as 34° C.

Polymer films for refractive index measurements are prepared by spin coating or drop casting from 1-8 wt % solutions of the polymers in chloroform onto silicon wafers or quartz plates. For production of bulk polymer blanks, the monomers are melted under vacuum. Appropriate amounts of a radical initiator and cross-linker are mixed in and quickly filled into a heated polymerization chamber. Cross-linked polymer plates are obtained.

Refractive index change is induced by irradiation at 340-365 nm. The refractive indices (n) of the polymer films and blanks at 590 nm are measured on Schmidt+Haensch AR12 before and after irradiation. The following table shows the refractive indices before and after irradiation as well as the change in refractive index (max. Δn).

Expected values for the cited polymers are given in the following table:

| Polymer No | $T_g$ [° C.] | n | Δn |
|---|---|---|---|
| P-001 | 16.1 | 1.603 | 0.028 |
| P-053 | 15.8 | 1.599 | 0.029 |
| P-034 | 26.3 | 1.601 | 0.030 |

Values for the cited polymer P-005 is given in the following table:

| Polymer No | $T_g$ [° C.] | $M_n$ | $M_w$ | D | n | Δn |
|---|---|---|---|---|---|---|
| P-005 | 24.6 | 2731 g/ol | 3236 g/mol | 1.19 | 1.563 | 0.003 |

The invention claimed is:

1. A compound of formula (I)

(I)

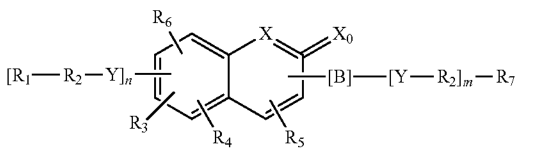

wherein

X is O or S, $X_0$ is O or S,

Y is O, S or a bond, n is 0 or 1, m is 0 or 1, n+m is 1 or 2,

—[B]— is selected from formulae (1) to (4), (1)

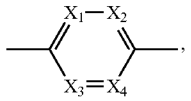

(2)

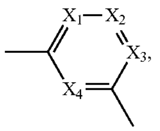

(3)

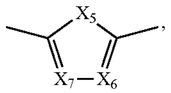

(4)

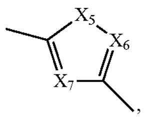

$X_1$, $X_2$, $X_3$, $X_4$ are each independently CR' or N, $X_5$ is O, S, C═O or $NR_0$, $X_6$, $X_7$ are each independently CR' or N, R is at each occurrence independently H, F, a linear or branched alkyl group having 1 to 4 C atoms, or a linear or branched, partially or fully fluorinated alkyl group having 1 to 4 C atoms, R' is at each occurrence independently H, F, a linear or branched, non-halogenated or partially or completely halogenated alkyl group having 1 to 20 C atoms, a linear or branched hydroxyalkyl group having 1 to 20 C atoms, a non-halogenated or partially or completely halogenated cycloalkyl group having 3 to 6 C atoms, a linear or branched, non-halogenated or partially or completely halogenated alkoxy group having 1 to 20 C atoms, or a linear or branched, non-halogenated or partially or completely halogenated thioalkyl group having 1 to 20 C atoms, $R_0$ is at each occurrence independently a linear or branched alkyl group having 1 to 10 C atoms or a cycloalkyl group having 3 to 6 C atoms, $R_1$ is a polymerizable group containing at least one Si atom, $—R_2—$ is $—(C(R)_2)_o—$, $—(C(R)_2)_p—X_8—(C(R)_2)_q—(X_9)_s—(C(R)_2)_r—(X_{10})_t—(C(R)_2)_u—$ or a cycloalkylene group having 5 or 6 C atoms which can be substituted with at least one R which is different from H, o is 1 to 20, $X_8$, $X_9$, $X_{10}$ are at each occurrence independently O, S or $NR_0$, s, t are each independently 0 or 1, p, q are at each occurrence independently 1 to 10, r, u are at each occurrence independently 0 to 10, wherein the overall number of atoms for $—(C(R)_2)_p—X_8—(C(R)_2)_q—(X_9)_s—(C(R)_2)_r—(X_{10})_t—(C(R)_2)_u—$ is up to 20 atoms, $R_3$, $R_4$, $R_5$, $R_6$ are at each occurrence independently H, F, a linear or branched, non-halogenated or partially or completely halogenated alkyl group having 1 to 20 C atoms, a linear or branched hydroxyalkyl group having 1 to 20 C atoms, a non-halogenated or partially or completely halogenated cycloalkyl group having 3 to 6 C atoms, a linear or branched, non-halogenated or partially or completely halogenated alkoxy group having 1 to 20 C atoms, or a linear or branched, non-halogenated or partially or completely halogenated thioalkyl group having 1 to 20 C atoms, $R_7$ is, in case m is 0, H, F, a linear or branched, non-halogenated or partially or completely halogenated alkyl group having 1 to 20 C atoms, a linear or branched hydroxyalkyl group having 1 to 20 C atoms, a non-halogenated or partially or completely halogenated cycloalkyl group having 3 to 6 C atoms, a linear or branched, non-halogenated or partially or completely halogenated alkoxy group having 1 to 20 C atoms, or a linear or branched, non-halogenated or partially or completely halogenated thioalkyl group having 1 to 20 C atoms, and $R_7$ is, in case m is 1, a polymerizable group containing at least one Si atom.

2. The compound according to claim 1, wherein —[B]— corresponds to formula (1) or formula (2).

3. The compound according to claim 1, wherein $X_1$, $X_3$ and $X_4$ in formula (1) or (2) are each CR'.

4. The compound according to claim 1, wherein $X_2$ is CR'.

5. The compound according to claim 1, wherein at least one R' within $X_1$, $X_2$, $X_3$, $X_4$, $X_6$ or $X_7$ in formulae (1) to (4) is not H.

6. The compound according to claim 1, wherein n is 1 and m is 0, and said compounds are of formula (I')

(I')

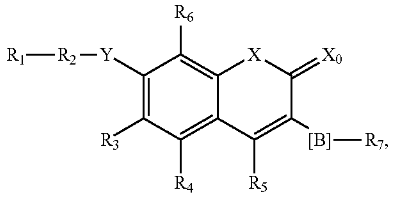

wherein $R_1$, —$R_2$—, Y, $R_3$, $R_4$, $R_5$, $R_6$, X, $X_0$, —[B]— and $R_7$ have the meanings indicated in claim 1.

7. The compound according to claim 1, wherein n is 0 and m is 1, and said compounds are of formula (I'')

(I'')

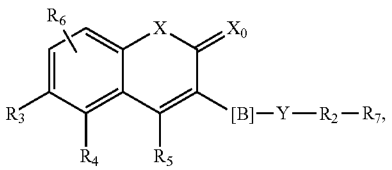

wherein $R_1$, —$R_2$—, Y, $R_3$, $R_4$, $R_5$, $R_6$, X, $X_0$, —[B]— and $R_7$ have the meanings indicated in claim 1.

8. The compound according to claim 1, wherein n is 1 and m is 1, and said compounds are of formula (I''')

(I''')

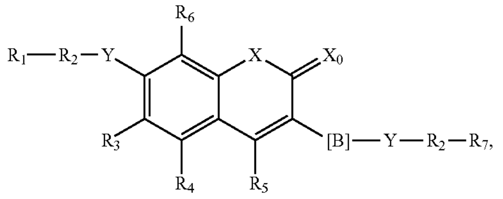

wherein $R_1$, —$R_2$—, Y, $R_3$, $R_4$, $R_5$, $R_6$, X, $X_0$, —[B]— and $R_7$ the meanings indicated in claim 1.

9. The compound according to claim 1, wherein —$R_2$— is at each occurrence independently —$(C(R)_2)_o$—, and R is at each occurrence independently H or F and o has a meaning as indicated in claim 1.

10. The compound according to claim 1, wherein $R_1$ is at each occurrence independently a diethoxymethylsilyl or triethoxysilyl radical.

11. An oligomer or polymer comprising a polymerized compound of formula (I) according to claim 1.

12. A composition comprising at least one compound of formula (I) according to claim 1.

13. An article comprising an oligomer or polymer according to claim 11.

14. The article according to claim 13, wherein said article is a blank which may be transformed into an eye implant.

15. A process of forming an article of claim 13, said process comprising:

providing a composition comprising said oligomer or polymer; and subsequently forming the article of said composition.

16. A process of changing the optical properties of an article according to claim 13, said process comprising:

providing an article according to claim 13, and subsequently exposing said article to irradiation having a wavelength of at least 200 nm and at most 1500 nm.

17. A composition comprising an oligomer or polymer according to claim 11.

18. The article according to claim 13, wherein said article is an ophthalmic device.

19. The article according to claim 18, wherein said ophthalmic device is a lens, a keratoprosthesis, a cornea inlay, or a cornea ring.

20. A process of forming an article, said process comprising:

polymerizing one or more compounds according to claim 1 to form a blank, transforming the blank into the article, wherein said article is an ophthalmic device.

21. A process of forming an article, said process comprising:

polymerizing one or more compounds compound according to claim 1 to form an oligomer or polymer composition, form a blank from the oligomer or polymer composition, and shaping the blank by cutting, optic lathe cutting, optic milling, and/or haptic milling to form the article.

22. A copolymer comprising a polymerized compound of formula (I) according to claim 1 wherein the polymerizable group $R_1$ forms part of a co-polymer backbone.

23. The copolymer according to claim 22, wherein said copolymer comprises one or more constitutional units $M^0$ of formulae (1-p-1), (1-p-2), (1-p-3), (1-p-4), (1-p-5), (1-p-6), (1-p-7), (1-p-8), (1-p-9), (1-p-10) or (1-p-11):

-continued

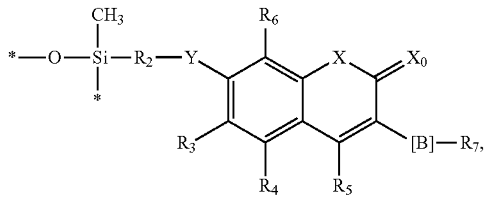
(1-p-1)

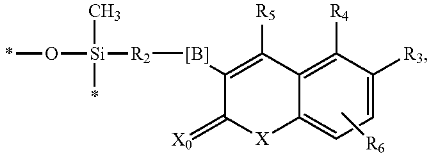
(1-p-2)

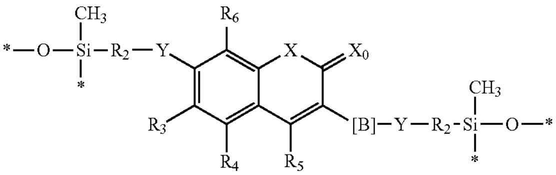
(1-p-3)

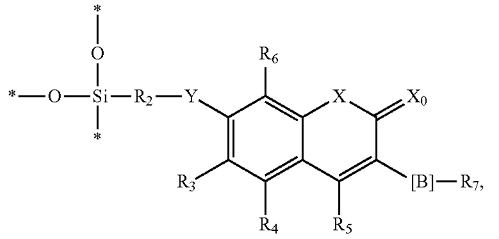
(1-p-4)

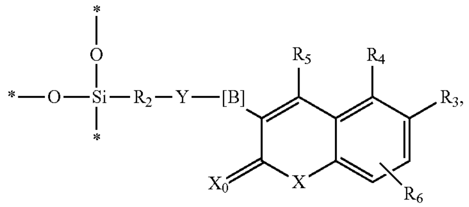
(1-p-5)

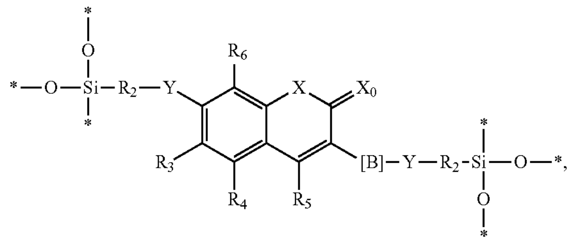
(1-p-6)

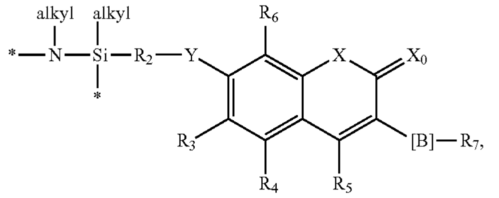
(1-p-7)

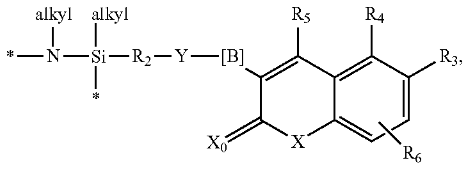
(1-p-8)

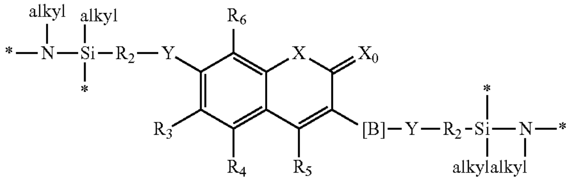
(1-p-9)

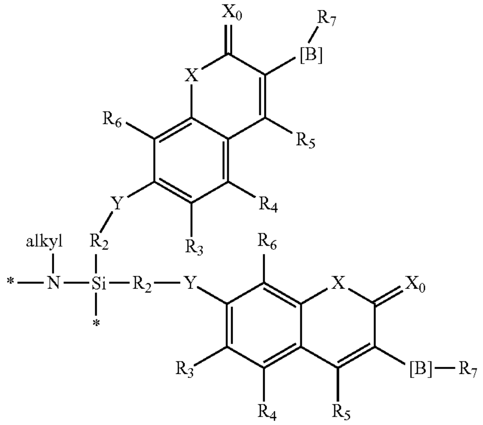
(1-p-10)

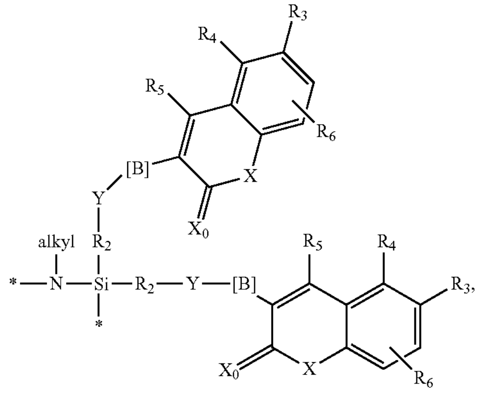
(1-p-11)

wherein —$R_2$—, Y, $R_3$, $R_4$, $R_5$, $R_6$, X, $X_0$, —[B]—, and $R_7$ have the meanings defined in claim 1, and "alkyl" means a linear or branched alkyl group having 1 to 6 C atoms.

24. The copolymer according to claim 23, wherein said copolymer further comprises one or more constitutional units $M^2$ which are chemically different from the units $M^0$.

25. The copolymer according to claim 24, wherein said one or more constitutional units $M^2$ which are derived by polymerization of one or more monomers selected from trialkoxyalkenylsilanes, dialkoxyalkylalkenylsilanes, and silanes of formula (8) or (9), (8)

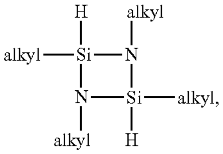

(9)

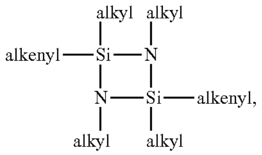

where the alkyl groups are, at each occurrence independently, linear or branched having 1 to 6 C atoms and the alkenyl group is, at each occurrence independently, linear having 2 to 4 C atoms.

26. An article comprising at least one copolymer according to claim 23.

27. An article comprising at least one copolymer according to claim 24.

28. An article comprising at least one copolymer according to claim 25.

29. The article according to claim 26, wherein said copolymer is cross-linked.

30. The article according to claim 27, wherein said copolymer is cross-linked.

31. The article according to claim 28, wherein said copolymer is cross-linked.

32. The copolymer according to claim 24, wherein said copolymer comprises the one or more constitutional units $M^0$ in a molar ratio m1 and the one or more constitutional units $M^2$ in a molar ratio m2, wherein the ratio m1:m2 is at least 0.01 and at most 100.

33. An article comprising at least one copolymer according to claim 32.

34. An article according to claim 18, wherein the ophthalmic device comprises one or more optic components and one or more haptic components, wherein the one or more optic components serve as a lens and the one or more haptic components are attached to the one or more optic components and hold the one or more optic components in place in the eye.

35. An article according to claim 18, wherein the article has a one-piece design.

36. An article according to claim 18, wherein the article has a multi-piece design.

37. An article produced by the process according to claim 16.

38. The compound according to claim 1, wherein m is 0.

* * * * *